US009636387B2

(12) United States Patent
Abdul-Wahid et al.

(10) Patent No.: US 9,636,387 B2
(45) Date of Patent: *May 2, 2017

(54) N-DOMAIN OF CARCINOEMBRYONIC ANTIGEN AND COMPOSITIONS, METHODS AND USES THEREOF

(71) Applicant: Governing Council of the University of Toronto, Toronto (CA)

(72) Inventors: Aws Abdul-Wahid, Montreal (CA); Jean Gariépy, Toronto (CA)

(73) Assignee: Governing Council of the University of Toronto, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/461,585

(22) Filed: Aug. 18, 2014

(65) Prior Publication Data
US 2015/0044218 A1    Feb. 12, 2015

Related U.S. Application Data

(63) Continuation of application No. 13/697,295, filed as application No. PCT/CA2011/000540 on May 11, 2011, now Pat. No. 8,846,050.

(60) Provisional application No. 61/333,587, filed on May 11, 2010.

(51) Int. Cl.
| | |
|---|---|
| *A61K 39/00* | (2006.01) |
| *A61K 39/395* | (2006.01) |
| *C07K 16/18* | (2006.01) |
| *C07K 14/435* | (2006.01) |
| *C07K 16/30* | (2006.01) |
| *A61K 31/711* | (2006.01) |
| *A61K 48/00* | (2006.01) |

(52) U.S. Cl.
CPC ........ *A61K 39/0011* (2013.01); *A61K 31/711* (2013.01); *A61K 39/39558* (2013.01); *C07K 14/435* (2013.01); *C07K 16/18* (2013.01); *C07K 16/3007* (2013.01); *A61K 48/00* (2013.01); *A61K 2039/505* (2013.01); *A61K 2039/53* (2013.01); *A61K 2039/55561* (2013.01); *A61K 2039/575* (2013.01); *C07K 2317/732* (2013.01); *C07K 2317/734* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,595,756 A * | 1/1997 | Bally et al. ................ | 424/450 |
| 5,648,078 A | 7/1997 | Hashino et al. | |
| 5,672,513 A | 9/1997 | Terskikh et al. | |
| 2005/0063952 A1 | 3/2005 | Klysner et al. | |
| 2005/0147614 A1* | 7/2005 | Begent et al. ............. | 424/155.1 |

FOREIGN PATENT DOCUMENTS

| | | |
|---|---|---|
| CN | 1634982 A | 7/2005 |
| WO | 2009002418 A | 12/2008 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Vajdos et al. (J Mol Biol. Jul. 5, 2002;320(2):415-28 at 416).*
Brown et al. (J Immunol. May 1996;156(9):3285-91.*
Sporn et al, "Chemoprevention of Cancer," Carcinogenesis, vol. 21 (2000), 525-530.*
Auerbach et al (Cancer and Metastasis Reviews, 2000, 19: 167-172).*
Gura T (Science, 1997, 278(5340): 1041-1042, encloses 1-5).*
Jain RK (Scientific American, Jul. 1994,58-65).*
Sainz-Pastor et al (Int J Biol Macromol. Aug. 15, 2006;39(1-3):141-50. Epub Mar. 28, 2006).*
Hefta, Laura J.F. et al., Expression of Carcinoembryonic Antigen and Its Predicted Immunoglobulin-like Domains in HeLa Cells for Epitope Analysis, Cancer Research, vol. 52, pp. 5647-5655. Oct. 15, 1992.
Aurisicchio, L. et al. "Patented cancer vaccines: the promising leads." Expert Opin. Ther. Patents (2010) 20(5), pp. 1-14.
Hallermalm, K. "T-cell epitope analogues from carcinoembryonic antigen for vaccination against cancer: WO2009002418". Expert Opin. Ther. Patents (2009) 19(11), pp. 1635-1637.
Abdul-Wahid, Aws and Gariépy, Jean, Overcoming Immunological Anergy Against the Human Carcinoembryonic Antigen Results in Delayed Tumor Growth. Poster and Abstract. CI 2010.org—14th International Congress of Immunology. Aug. 22-27, 2010—Kobe, Japan.
Abdul-Wahid, Aws et al., Overcoming Immunological Anergy Against the Human Carcinoembryonic Antigen (CEA) Results in Delayed Tumor Growth. p. 42, 20th Annual International CEA Symposium, McGill University, Montreal, Quebec, Aug. 8-11, 2010.
Hodge, James W., "Carcinoembryonic antigen as a target for cancer vaccines", Cancer Immunology and Immunotherapy, Springer-Verlag, 1996, vol. 43: pp. 127-134.
Hashino, J. et al., "Production and Characterization of Monoclonal Antibodies to N-Domain and Domain III of Carcinoembryonic Antigen", Biochemical and Biophysical Research Communications, Dec. 15, 1993, vol. 197, No. 2, pp. 886-893.
Blumenthal, R.D. et al., "Inhibition of Adhesion, Invasion, and Metastasis by Antibodies Targeting CEACAM6 (MCA-90) and CEACAM5 (Carcinoembryonic Antigen)", Cancer Research, Oct. 1, 2005, vol. 65, No. 19, pp. 8809-8817.

* cited by examiner

*Primary Examiner* — Brian J Gangle
*Assistant Examiner* — Andrea McCollum
(74) *Attorney, Agent, or Firm* — Bereskin & Parr LLP; Melanie Szweras

(57) ABSTRACT

The present disclosure provides immunogenic compositions comprising the N-domain of carcinoembryonic antigen (CEA). These compositions are useful for inducing or enhancing an immune response, for inhibiting tumor cell growth and for treating cancer.

14 Claims, 29 Drawing Sheets

A.

CEA WT N-domain

KLTIESTPFNVAEGKE<u>VLLLVHNLPQHLF</u>*G*
*YSWYK*GERVDG*NRQII*GYVIGTQQATPGPA
YSGR<u>EIIYPNASLLIQNII</u>*QND*T*GFYTLHVIK
SDL*VNEEATGQFRVY*PELPK*PSISSNNSKPV
EDKDAVAFT

CEA Mutant N-domain

KLTSTSTPFNVAEGKE<u>VLLLVHNLPQHLF</u>*G*
*YSWYK*GERVDG*NRQII*GYVIGTQQATPGPA
YSGR<u>EIIYPNASLLIQNII</u>*QND*TGFYTLHVIK
SDL*VNEEATGQFRVY*PELPK*PSTSSTTSKP
VEDKDAVAFT

B.

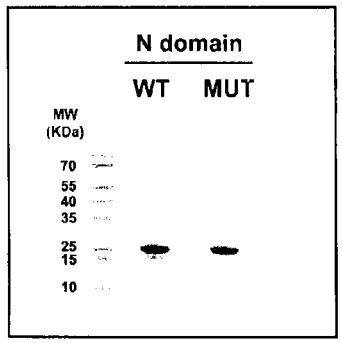

C.

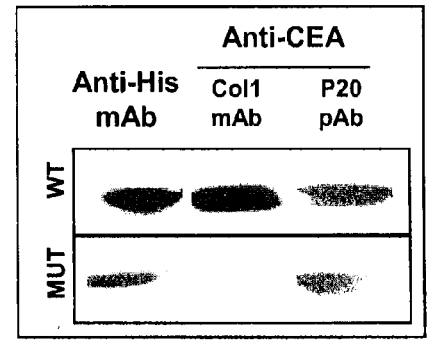

Figure 3

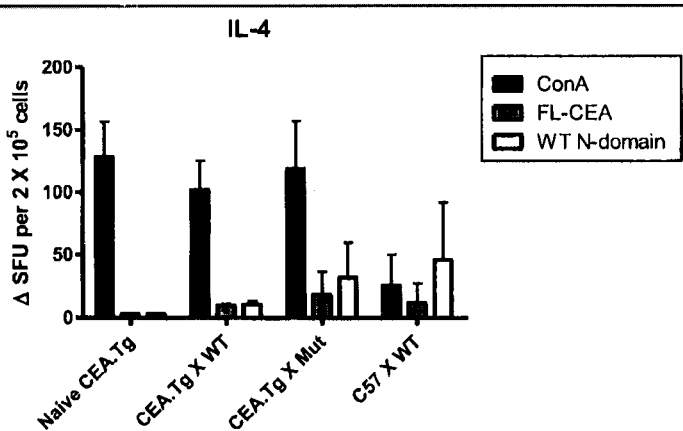
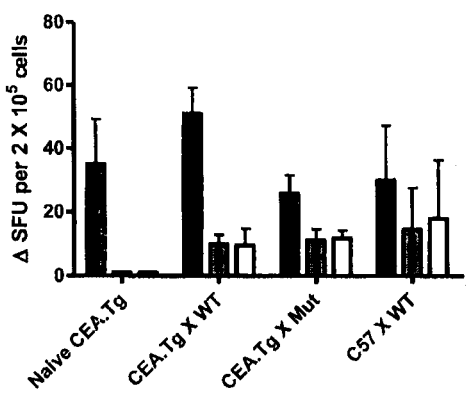
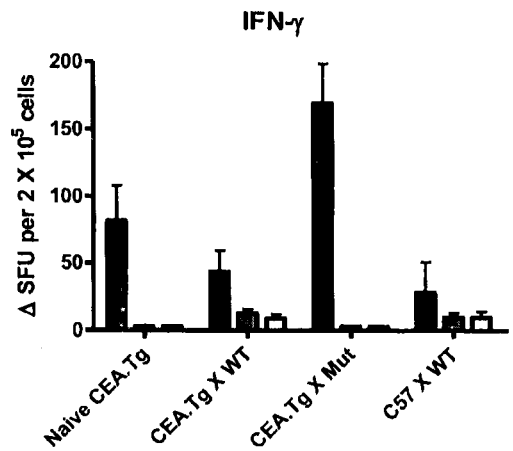
Figure 6

A

B

Figure 10
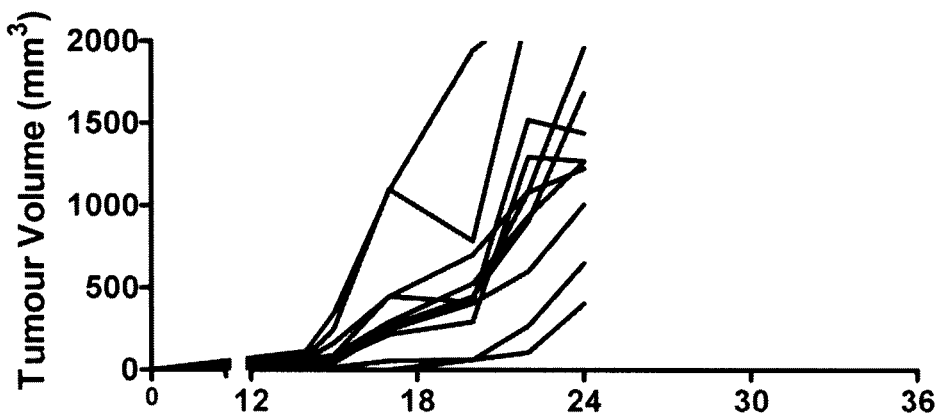
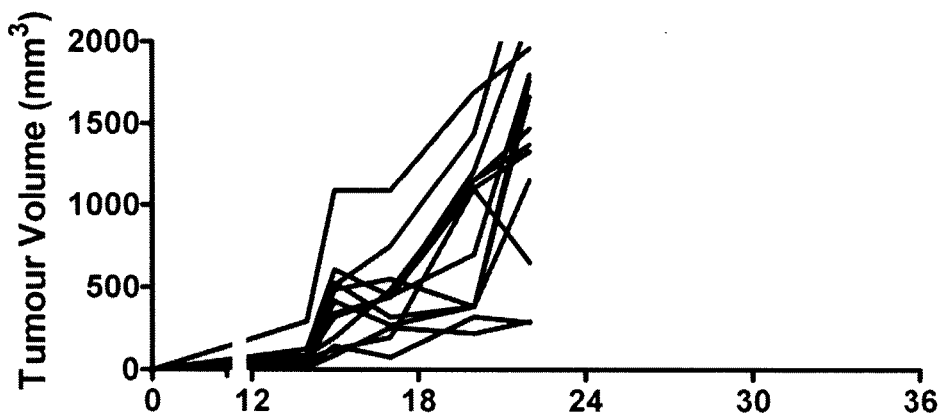
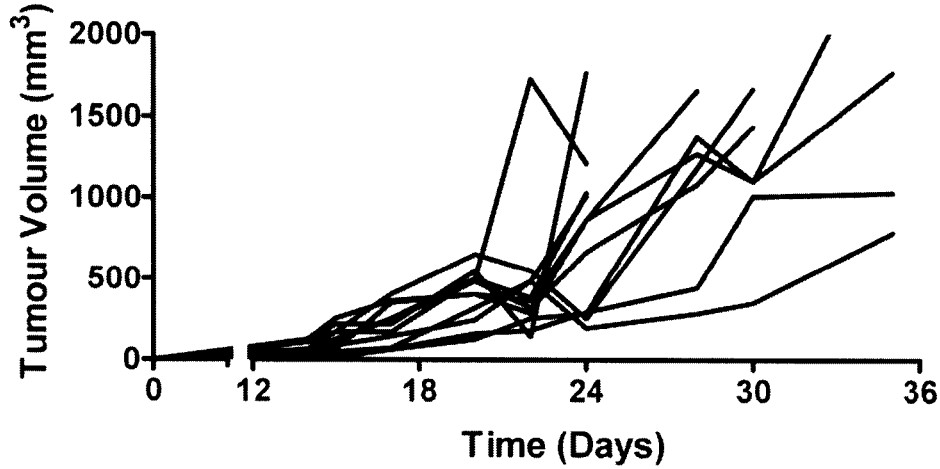

Figure 13
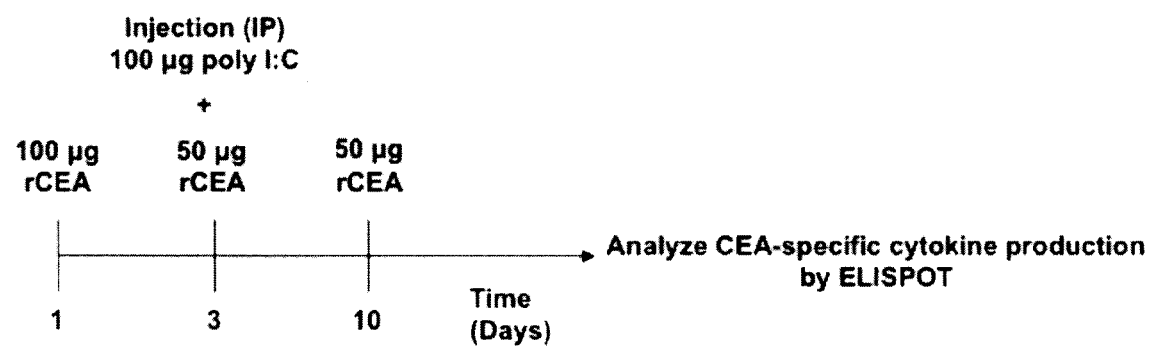
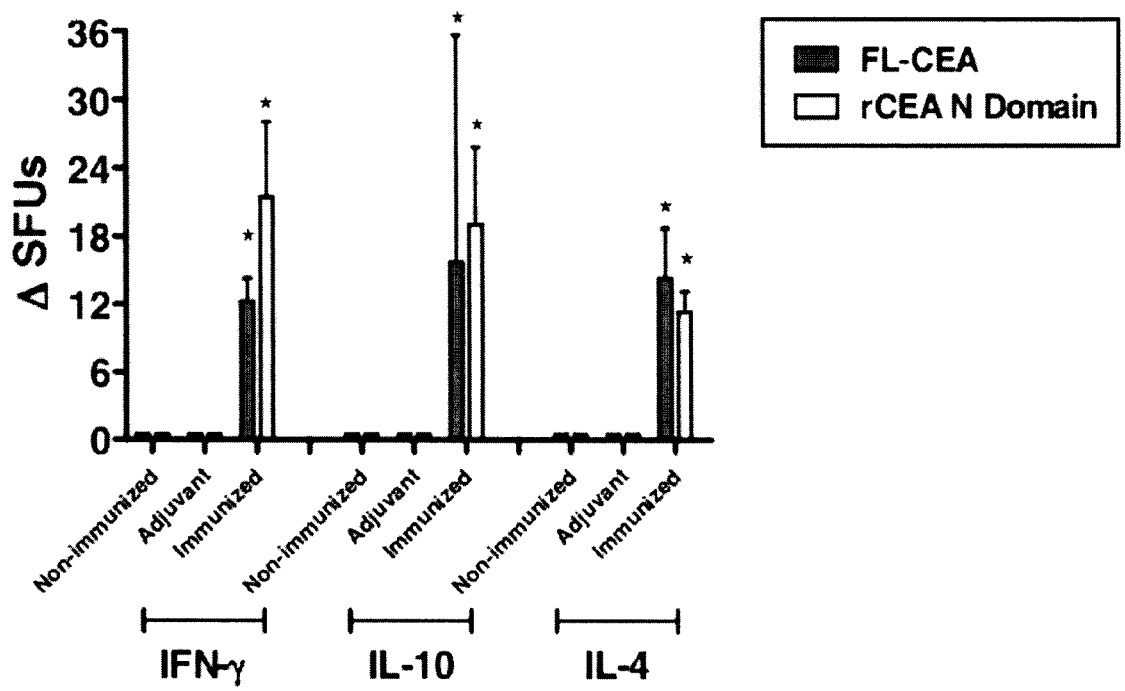

Figure 14
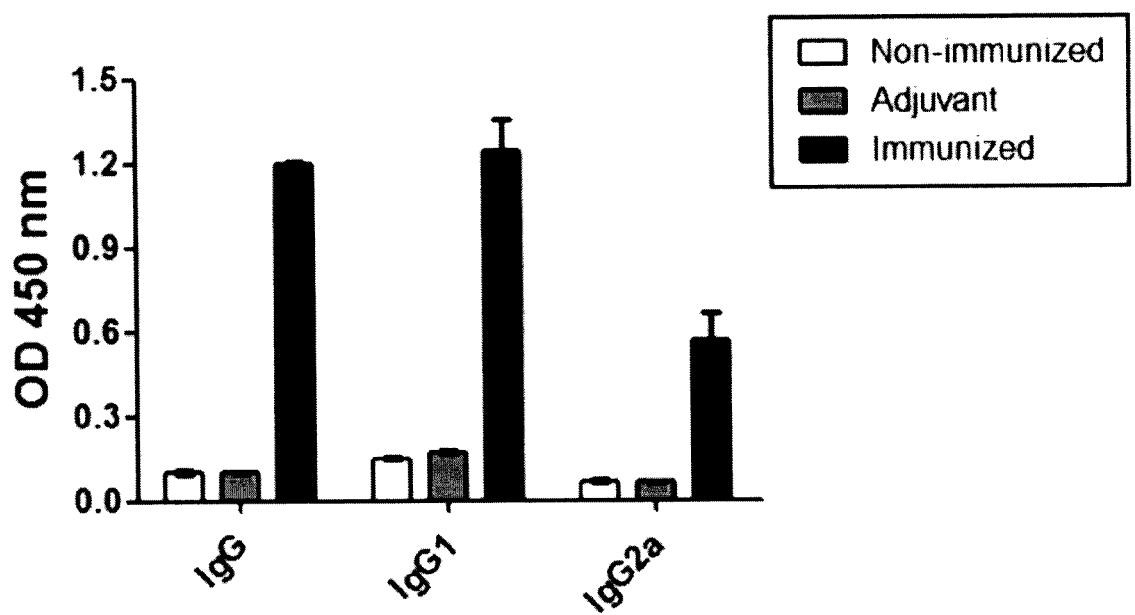
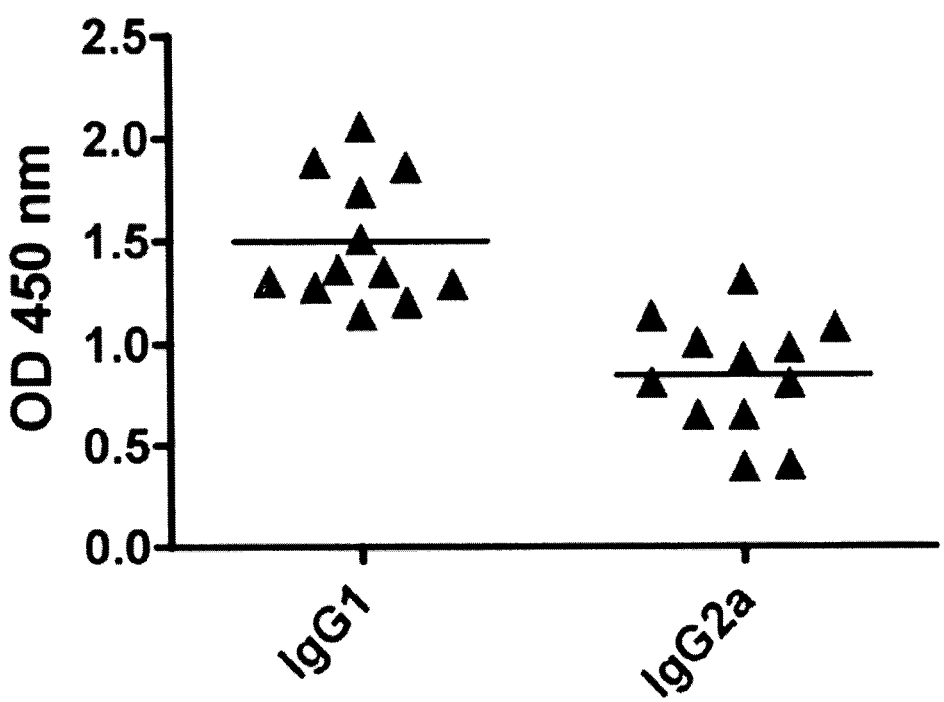

Figure 15
A
ADCC
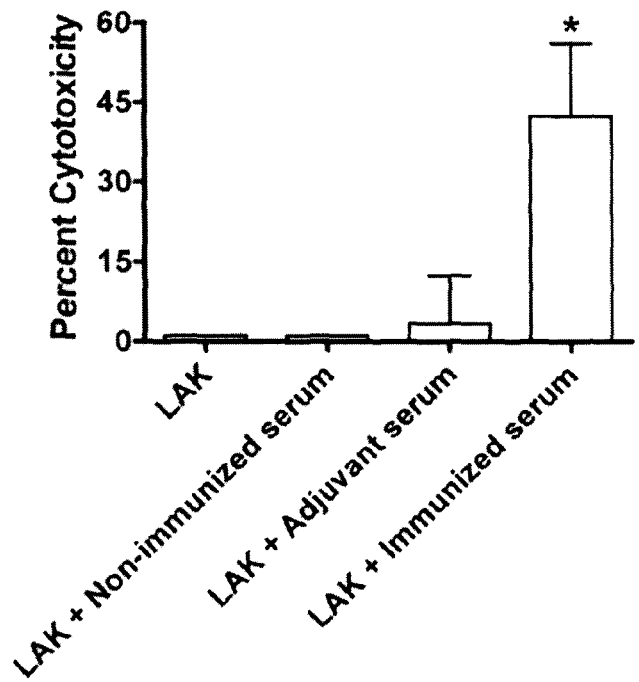
B
CDC
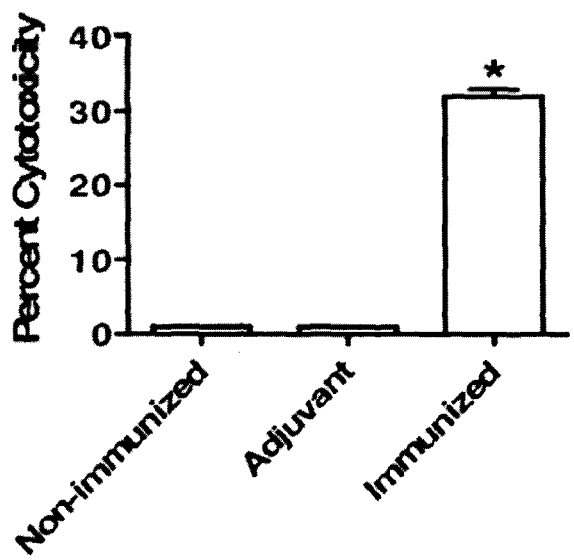

Figure 15
C
Inhibition of CEA-mediated cellular adhesion
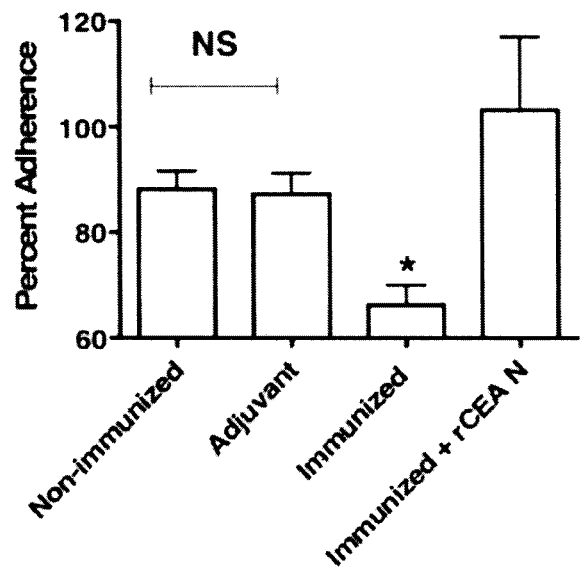
D
Inhibition of CEA-mediated homotypic interaction
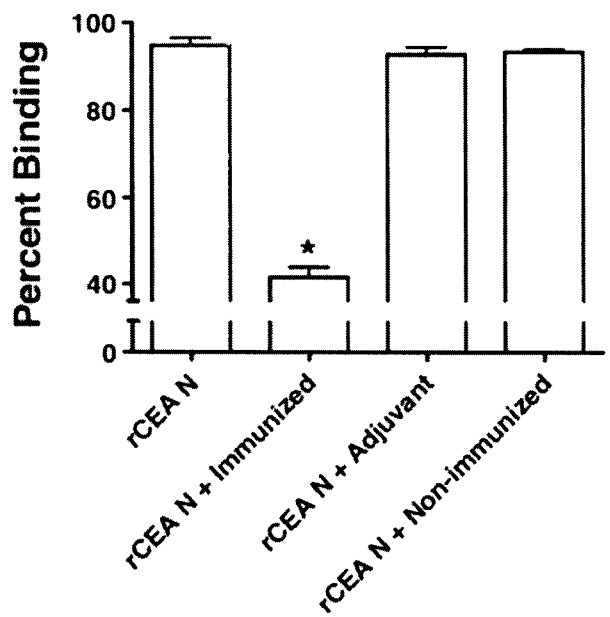

A

Figure 20
A.
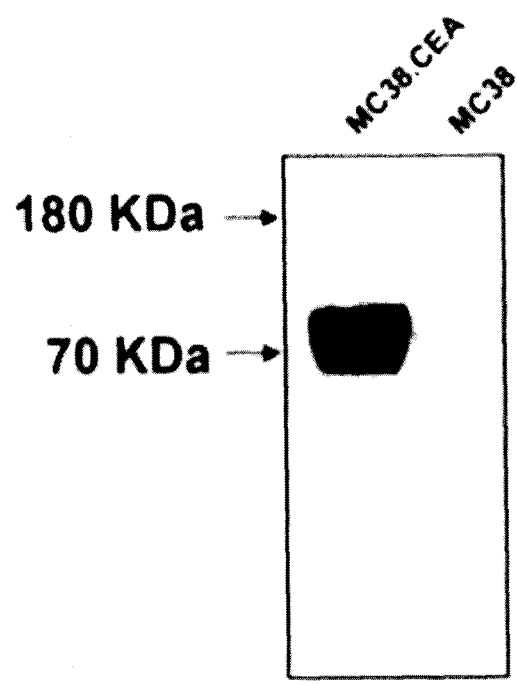
B.
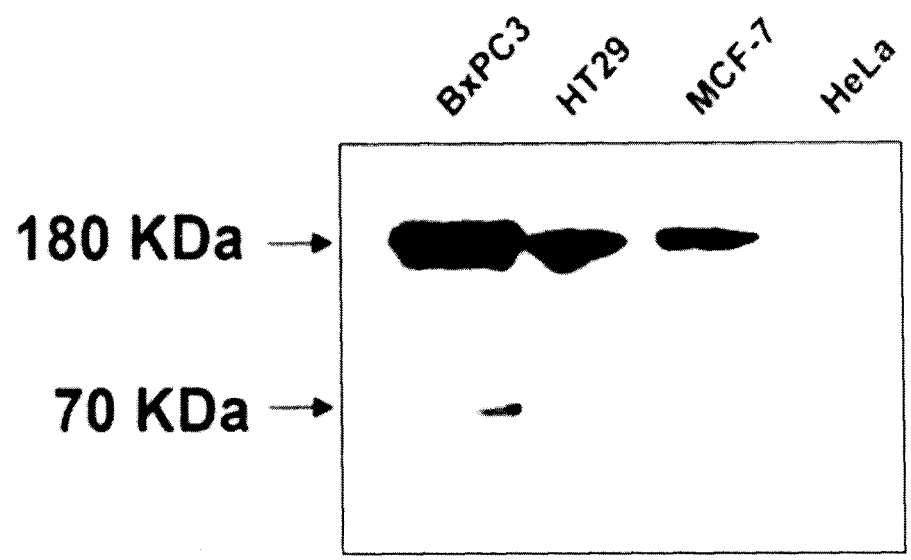

SEQUENCE LISTING

```
<160> NUMBER OF SEQ ID NOS: 14

<210> SEQ ID NO 1
<211> LENGTH: 132
<212> TYPE: PRT
<213> ORGANISM: Homo sapiens

<400> SEQUENCE: 1

Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
        35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
```

```
                    85                  90                  95

Asn Glu Glu Ala Thr Gly Gln Phe Arg Val Tyr Pro Glu Leu Pro Lys
                100                 105                 110

Pro Ser Ile Ser Ser Asn Asn Ser Lys Pro Val Glu Asp Lys Asp Ala
            115                 120                 125

Val Ala Phe Thr
            130

<210> SEQ ID NO 2
<211> LENGTH: 132
<212> TYPE: PRT
<213> ORGANISM: Artificial Sequence
<220> FEATURE:
<223> OTHER INFORMATION: Mutant N Domain amino acid

<400> SEQUENCE: 2

Lys Leu Thr Ser Thr Ser Thr Pro Phe Asn Val Ala Glu Gly Lys Glu
1               5                   10                  15

Val Leu Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
        35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
                100                 105                 110

Pro Ser Thr Ser Ser Thr Thr Ser Lys Pro Val Glu Asp Lys Asp Ala
            115                 120                 125

Val Ala Phe Thr
            130

<210> SEQ ID NO 3
<211> LENGTH: 396
<212> TYPE: DNA
<213> ORGANISM: Homo sapiens

<400> SEQUENCE: 3
aagctcacta ttgaatccac gccgttcaat gtcgcagagg ggaaggaggt gcttctactt      60
gtccacaatc tgccccagca tctttttggc tacagctggt acaaaggtga agagtggat     120 ggcaaccgtc aaattatagg atatgtaata ggaactcaac aagctacccc agggcccgca    180
tacagtggtc gagagataat ataccccaat gcatccctgc tgatccagaa catcatccag    240
aatgacacag gattctacac cctacacgtc ataaagtcag atcttgtgaa tgaagaagca    300
actggccagt tccgggtata cccggagctg cccaagccct ccatctccag caacaactcc    360
aaacccgtgg aggacaagga tgctgtggcc ttcacc                              396

<210> SEQ ID NO 4
<211> LENGTH: 468
<212> TYPE: DNA
<213> ORGANISM: Artificial Sequence
<220> FEATURE:
<223> OTHER INFORMATION: Mutant N Domain nucleic acid

<400> SEQUENCE: 4
```

```
gcgatacata tgcatcatca ccatcaccat gaaaacctct atttccaaaa gctcactagc    60
acttccacgc cgttcaatgt cgcagagggg aaggaggtgc ttctacttgt ccacaatctg   120
ccccagcatc tttttggcta cagctggtac aaaggtgaaa gagtggatgg caaccgtcaa   180
attataggat atgtaatagg aactcaacaa gctaccccag ggcccgcata cagtggtcga   240
gagataatat accccaatgc atccctgctg atccagaaca tcatccagaa tgacacagga   300
ttctacaccc tacacgtcat aaagtcagat cttgtgaatg aagaagcaac tggccagttc   360
cgggtatacc cggagctgcc caagccctcc acctccagca cgacttccaa acccgtggag   420
gacaaggatg ctgtggcctt cacctagctc gagggatcca ctcaggac               468
```

<210> SEQ ID NO 5
<211> LENGTH: 687
<212> TYPE: DNA
<213> ORGANISM: Artificial Sequence
<220> FEATURE:
<223> OTHER INFORMATION: CEA A3B3 nucleic acid

<400> SEQUENCE: 5

```
tatacccata tggccaataa ctcagccagt ggccacagca ggactacagt caagacaatc    60
acagtctctg cggagctgcc caagccctcc atctccagca caactccaa acccgtggag   120 gacaaggatg ctgtggcctt cacctgtgaa cctgaggctc agaacacaac ctacctgtgg   180
tgggtaaatg gtcagagcct cccagtcagt cccaggctgc agctgtccaa tggcaacagg   240
accctcactc tattcaatgt cacaagaaat gacgcaagag cctatgtatg tggaatccag   300
aactcagtga gtgcaaaccg cagtgaccca gtcaccctgg atgtcctcta tgggccggac   360 accccccatca tttcccccccc agactcgtct tacctttcgg gagcgaacct caacctctcc   420
tgccactcgg cctctaaccc atccccgcag tattcttggc gtatcaatgg gataccgcag   480
caacacacac aagttctctt tatcgccaaa atcacgccaa ataataacgg gacctatgcc   540
tgttttgtct ctaacttggc tactggccgc aataattcca tagtcaagag catcacagtc   600
tctgcatctg gaacttctcc tggtctctca gctggggcca ctgtcggcca ccatcaccat   660
caccatcacc attgactcga gatatag                                      687
```

<210> SEQ ID NO 6
<211> LENGTH: 221
<212> TYPE: PRT
<213> ORGANISM: Artificial Sequence
<220> FEATURE:
<223> OTHER INFORMATION: CEA A3B3 amino acid

<400> SEQUENCE: 6

```
Met Ala Asn Asn Ser Ala Ser Gly His Ser Arg Thr Thr Val Lys Thr
1               5                   10                  15

Ile Thr Val Ser Ala Glu Leu Pro Lys Pro Ser Ile Ser Ser Asn Asn
            20                  25                  30

Ser Lys Pro Val Glu Asp Lys Asp Ala Val Ala Phe Thr Cys Glu Pro
        35                  40                  45

Glu Ala Gln Asn Thr Thr Tyr Leu Trp Trp Val Asn Gly Gln Ser Leu
    50                  55                  60

Pro Val Ser Pro Arg Leu Gln Leu Ser Asn Gly Asn Arg Thr Leu Thr
65                  70                  75                  80

Leu Phe Asn Val Thr Arg Asn Asp Ala Arg Ala Tyr Val Cys Gly Ile
                85                  90                  95
```

```
Gln Asn Ser Val Ser Ala Asn Arg Ser Asp Pro Val Thr Leu Asp Val
                100                 105                 110
Leu Tyr Gly Pro Asp Thr Pro Ile Ile Ser Pro Asp Ser Ser Tyr
            115                 120                 125
Leu Ser Gly Ala Asn Leu Asn Leu Ser Cys His Ser Ala Ser Asn Pro
        130                 135                 140
Ser Pro Gln Tyr Ser Trp Arg Ile Asn Gly Ile Pro Gln Gln His Thr
145                 150                 155                 160
Gln Val Leu Phe Ile Ala Lys Ile Thr Pro Asn Asn Asn Gly Thr Tyr
                165                 170                 175
Ala Cys Phe Val Ser Asn Leu Ala Thr Gly Arg Asn Asn Ser Ile Val
            180                 185                 190
Lys Ser Ile Thr Val Ser Ala Ser Gly Thr Ser Pro Gly Leu Ser Ala
        195                 200                 205
Gly Ala Thr Val Gly His His His His His His
    210                 215                 220

<210> SEQ ID NO 7
<211> LENGTH: 147
<212> TYPE: PRT
<213> ORGANISM: Artificial Sequence
<220> FEATURE:
<223> OTHER INFORMATION: Tagged Wt N Domain amino acid

<400> SEQUENCE: 7

Met His His His His His His His Glu Asn Leu Tyr Phe Gln Lys
1               5                   10                  15
Leu Thr Ile Glu Ser Thr Pro Phe Asn Val Ala Glu Gly Lys Glu Val
                20                  25                  30
Leu Leu Leu Val His Asn Leu Pro Gln His Leu Phe Gly Tyr Ser Trp
            35                  40                  45
Tyr Lys Gly Glu Arg Val Asp Gly Asn Arg Gln Ile Ile Gly Tyr Val
        50                  55                  60
Ile Gly Thr Gln Gln Ala Thr Pro Gly Pro Ala Tyr Ser Gly Arg Glu
65                  70                  75                  80
Ile Ile Tyr Pro Asn Ala Ser Leu Leu Ile Gln Asn Ile Ile Gln Asn
                85                  90                  95
Asp Thr Gly Phe Tyr Thr Leu His Val Ile Lys Ser Asp Leu Val Asn
            100                 105                 110
Glu Glu Ala Thr Gly Gln Phe Arg Val Tyr Pro Glu Leu Pro Lys Pro
        115                 120                 125
Ser Ile Ser Ser Asn Asn Ser Lys Pro Val Glu Asp Lys Asp Ala Val
    130                 135                 140
Ala Phe Thr
145

<210> SEQ ID NO 8
<211> LENGTH: 78
<212> TYPE: DNA
<213> ORGANISM: Artificial Sequence
<220> FEATURE:
<223> OTHER INFORMATION: CEA N forward primer

<400> SEQUENCE: 8
gcgatacata tgcatcatca ccatcaccat gaaaacctct atttccaaaa gctcactatt      60
gaatccacgc cgttcaat                                                   78
```

<210> SEQ ID NO 9
<211> LENGTH: 39
<212> TYPE: DNA
<213> ORGANISM: Artificial Sequence
<220> FEATURE:
<223> OTHER INFORMATION: CEA N reverse primer

<400> SEQUENCE: 9
gtcctgagtg gatccctcga gctaggtgaa ggccacagc        39

<210> SEQ ID NO 10
<211> LENGTH: 100
<212> TYPE: DNA
<213> ORGANISM: Artificial Sequence
<220> FEATURE:
<223> OTHER INFORMATION: FLAG N Forward primer

<400> SEQUENCE: 10
cccatatggg cagcagccat catcatcatc atcacagcag cggcgactac aaggacgacg        60
atgacaagaa gctcactatt gaatccacgc cgttcaatgt        100

<210> SEQ ID NO 11
<211> LENGTH: 60
<212> TYPE: DNA
<213> ORGANISM: Artificial Sequence
<220> FEATURE:
<223> OTHER INFORMATION: FLAG N reverse primer

<400> SEQUENCE: 11
gttcagattt tcccctcga gctaagatgt gtttagaggg gaaatggtgg gggcatccgg        60

<210> SEQ ID NO 12
<211> LENGTH: 24
<212> TYPE: DNA
<213> ORGANISM: Artificial Sequence
<220> FEATURE:
<223> OTHER INFORMATION: A3B3 Forward Primer

<400> SEQUENCE: 12
tatacccata tggccaataa ctca        24

<210> SEQ ID NO 13
<211> LENGTH: 66
<212> TYPE: DNA
<213> ORGANISM: Artificial Sequence
<220> FEATURE:
<223> OTHER INFORMATION: A3B3 reverse primer

<400> SEQUENCE: 13
ctatatctcg agtcaatggt gatggtgatg gtgatggtgg ccgacagtgg ccccagctga        60
gagacc        66

<210> SEQ ID NO 14
<211> LENGTH: 438
<212> TYPE: DNA
<213> ORGANISM: Artificial Sequence
<220> FEATURE:
<223> OTHER INFORMATION: Tagged Wt N domain amino acid

<400> SEQUENCE: 14
atgcatcatc accatcacca tgaaaacctc tatttccaaa agctcactat tgaatccacg        60
ccgttcaatg tcgcagaggg gaaggaggtg cttctacttg tccacaatct gccccagcat        120 cttttttggct acagctggta caaaggtgaa agagtggatg gcaaccgtca aattatagga        180

```
                                           -continued tatgtaatag gaactcaaca agctacccca gggcccgcat acagtggtcg agagataata         240
taccccaatg catccctgct gatccagaac atcatccaga atgacacagg attctacacc         300
ctacacgtca taaagtcaga tcttgtgaat gaagaagcaa ctggccagtt ccgggtatac         360
ccggagctgc ccaagccctc catctccagc aacaactcca aacccgtgga ggacaaggat         420
gctgtggcct tcacctag                                                      438
```

N-DOMAIN OF CARCINOEMBRYONIC ANTIGEN AND COMPOSITIONS, METHODS AND USES THEREOF

RELATED APPLICATIONS

This application is a continuation of U.S. patent application Ser. No. 13/697,295 filed on Nov. 9, 2012 (now allowed), which is a national phase entry of PCT/CA2011000540 filed May 11, 2011 (which designated the US), which claims priority from U.S. provisional application No. 61/333,587 filed May 11, 2010. All of the prior applications are incorporated herein in their entirety.

INCORPORATION OF SEQUENCE LISTING

A computer readable form of the Sequence Listing "2223-P37014US02_SequenceListing.txt" (12,288 bytes), submitted via EFS-WEB and created on Aug. 12, 2014, is herein incorporated by reference.
Please replace the Sequence Listing currently of record with the Sequence Listing provided herewith in text format in computer readable form only.

FIELD OF THE DISCLOSURE

The disclosure relates to the N-domain of carcinoembryonic antigen (CEA) and methods and uses thereof. In particular, the disclosure relates to compositions, methods and uses of the N-domain of CEA for treating cancer.

BACKGROUND OF THE DISCLOSURE

The human carcinoembryonic antigen (CEA, CEACAM5, CD66e) is a glycosyl phosphatidyl (GPI)-linked glycoprotein that was originally described as a gastrointestinal oncofetal antigen [Gold and Freedman, 1985]. This cell surface antigen is frequently over-expressed on epithelial carcinomas of the intestinal and respiratory tracts, as well as cancers of the breast, pancreas, stomach, and ovary [Goldenberg at al., 1976; Shively at al., 1985; Thompson et al., 1991; Gold and Goldenberg, 1997; Hammarstrom, 1999]. From a clinical perspective, high preoperative levels of CEA in the blood of cancer patients negatively correlate with disease free survival. Intercellular adhesion events involving CEA have been linked to cancer invasion and metastasis [Jessup and Thomas, 1998; Yoshioka at al., 1998; Thomas at al., 1995]. As such, strategies interfering with CEA-specific functions and CEA-dependent cellular interactions may block or delay the establishment of metastatic tumour foci in vivo.

Structurally, CEA is composed of seven extracellular Ig-like domains (N, $A_1$, $B_1$, $A_2$, $B_2$, $A_3$ and $B_3$) and self-associates (defined as homotypic binding and homophilic cellular interactions) mainly through interactions involving its N and $A_3B_3$ Ig-like modules [Zhou et al., 1993]. Experimentally, the addition of monoclonal antibodies (mAbs) directed at epitopes found in the N domain of CEA [Jessup et al., 1993; Yamanka et al., 1996] as well as cyclic peptides derived from sequences within the N domain of CEA [Taheri et al., 2000] have been shown to inhibit CEA-specific cellular adhesion events in vitro. Similarly, administration of Fab' recognizing epitopes located in the N and adjacent $A_1B_1$ domains of CEA have been shown to increase the survival of nude mice harbouring CEA-expressing lung micrometastases [Blumenthal et al., 2005]. These findings suggest that an immune response specifically focused at blocking interactions involving the N domain of CEA may halt or limit the formation of tumour metastases in patients.

Previous attempts at developing CEA-based anti-tumor vaccines have centered on vaccine formulations based either on dendritic cells preloaded with predicted T-cell epitopes or recombinant viruses delivering the full length molecule [Curigliano et al., 2006; Berinstein, 2002; Zimmer and Thomas, 2001; Crosti et al., 2006; Shen et al., 2004; Kobayashi et al. 2002; Matsuda et al., 2004]. The majority of putative T-cell epitopes have been to short sequences located in the central region of this molecule [Curigliano et al., 2006; Berinstein, 2002; Zimmer and Thomas, 2001; Crosti et al., 2006; Shen et al., 2004; Kobayashi et al. 2002; Matsuda et al., 2004]. In another instance, predicted T cell (CTL) epitopes were altered to include a Val residue as the last residue, as an attempt to improve the peptide binding to HLA-A2 and therefore mount CEA-specific CTL responses [WO2009002418]. Unfortunately, the lack of immunogenicity of these epitopes coupled with the presence of immunosuppressive regulatory T ($T_{reg}$) cells in tumour microenvironments were shown to compromise the efficacy of anti-tumour CEA-based vaccines [Morse et al., 2008; Bos et al., 2008]. Overcoming these limitations has been attempted either through the depletion of immuno-suppressive $T_{reg}$ cells [Morse et al., 2008; Bos et al., 2008] or by co-administering TAA in combination with co-stimulatory molecules [Gulley et al., 2008; Dai et al., 2008].

A therapeutic vaccine aimed at blocking CEA-dependent adhesion events and the establishment of tumour foci may represent a more appropriate and achievable objective. Importantly, the role of CEA in metastasis is linked to its over-expression and associations which correlates with the early inactivation of caspase-9 and activation of the PI3-K/Akt survival pathway as well as the inactivation of caspase-8 [Camacho-Leal and Stanners, 2008] presumably by directly binding tumor necrosis factor-related apoptosis-inducing ligand (TRAIL-R2) (DR5) through its PELPK motif (residues 108-112 of the N domain of CEA) [Samara et al, 2007]. This peptide motif is responsible for mediating the lodging of metastasizing cells to the hepatic parenchyma leading to the development of metastatic foci by promoting intercellular aggregations through homophile cell interactions involving the IgV-like N- and the IgC-like $A_3$ domains [Berinstein, 2002; Benchimol at al., 1989; Taheri at al, 2000; Zimmer and Thomas, 2001].

SUMMARY OF THE DISCLOSURE

The present inventors have demonstrated that administration of both wild type and a deglycosylated mutant form of the N-domain of carcinoembryonic antigen (CEA) with adjuvant was able to overcome immunological tolerance and to raise an immune response capable of significantly interfering with tumor growth in transgenic mice expressing human CEA.

Accordingly, the present disclosure provides an immunogenic composition comprising an N-domain of carcinoembryonic antigen (CEA) or a nucleic acid encoding the N-domain. In one embodiment, the immunogenic composition further comprises an adjuvant, such as poly I:C, and/or a pharmaceutically acceptable carrier.

In one embodiment, the N-domain of CEA comprises the amino acid sequence as shown in SEQ ID NO:1, 2 or 7. In another embodiment, the N-domain of CEA consists of the amino acid sequence as shown in SEQ ID NO:1, 2 or 7. In yet another embodiment, the nucleic acid molecule comprises the nucleic acid sequence as shown in SEQ ID NO:3, 4 or 14.

In another embodiment, the immunogenic composition further comprises a second CEA domain. In one embodiment, the second CEA domain is an $A_3B_3$ domain. In a further embodiment, the immunogenic composition further comprises an adjuvant. In one embodiment, the adjuvant is poly I:C.

Also provided herein is a method of inducing or enhancing an immune response against carcinoembryonic antigen (CEA) comprising administering an effective amount of an N-domain of CEA or a nucleic acid molecule encoding the N-domain to an animal or cell in need thereof. Also provided herein is a method of inducing or enhancing an immune response against CEA comprising administering an effective amount of CEA N-domain specific sera or CEA N-domain specific antibodies to an animal or cell in need thereof.

Further provided is a method of inhibiting the growth of a carcinoembryonic antigen (CEA)-expressing tumour cell comprising administering an effective amount of an N-domain of CEA or a nucleic acid molecule encoding the N-domain to an animal or cell in need thereof. Also provided herein is a method of inhibiting growth of a CEA-expressing tumour cell comprising administering an effective amount of CEA N-domain specific sera or CEA N-domain specific antibodies to an animal or cell in need thereof.

Even further provided is a method of treating a subject with carcinoembryonic antigen (CEA)-associated cancer or an increased risk of said cancer comprising administering an effective amount of an N-domain of CEA or a nucleic acid molecule encoding the N-domain. Also provided herein is a method of treating a subject with CEA-associated cancer or an increased risk of said cancer comprising administering an effective amount of CEA N-domain specific sera or CEA N-domain specific antibodies to an animal or cell in need thereof. In one embodiment, the cancer is an epithelial cancer, such as cancer of the gastrointestinal tract, breast, lung or pancreas.

In another embodiment, the methods of the disclosure further comprise administration of a second CEA domain. In one embodiment, the second CEA domain is an $A_3B_3$ domain. In a further embodiment, the methods of the disclosure further comprise an adjuvant. In one embodiment, the adjuvant is poly I:C.

Also provided herein is an in vitro screening assay for identifying inhibitors of CEA-mediated homophilic interactions comprising incubating MC38.CEA$^{LUC}$ cells with a monolayer of non-luminescent MC38.CEA cells in the presence of a test compound; and assessing cell adherence by quantifying bioluminescence signal emitted by adhered MC38.CEA$^{LUC}$ cells, wherein a decrease in bioluminescence compared to a control indicates that the test compound is an inhibitor of CEA-mediated homophilic interactions.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 3 shows engineering and immunoreactivity of WT and mutant rCEA N domains. A. Primary sequence of the CEA N-domain (WT: SEQ ID NO:1 and mutant: SEQ ID NO:2), known immuno-dominant epitopes (underlined), the sequences responsible for adhesion and metastasis (italicized), and engineered O-glycosylation sites (bolded). B. Purity and immunoreactivity of expressed rCEA N domain modules. Coomassie-stained SDS-PAGE depicting the purity and molecular weights of the purified WT and mutant rCEA constructs. C. Western blot analysis of the immunoreactivity of the expressed rCEA wild type (WT) and mutant (MUT) N domains with a panel of antibodies specific to either the affinity tag (PentaHis mAb; Qiagen), the wild type CEA N domain (Col1 mAb; Invitrogen) or a polyclonal specific to various CEA epitopes (pan CEA P20; Santa-Cruz Biotechnology).

FIG. 6 shows stimulation of cytokine production following vaccination. Enumeration of CEA-specific IL-4 (A), IL-10 (B) and IFN-γ spot forming units (SFUs) in the spleens of CEA-immunized and control mice. Spleen leukocytes were collected 4 days following the last immunization and stimulated in vitro using either Concanavalin A (Con A; 2.5 ug per mL; Sigma-Aldrich), the full-length tumor glycoform of human CEA (FL-CEA; 1 ug per mL; Sigma-Aldrich) or the rCEA WT N-domain (WT N-domain; 1 ug per mL). The number of Ag-specific cytokine secreting SFUs was counted using an automated ELISPOT™ plate counter (Cellular Technologies Inc). Data is presented as the difference between the number of spots observed in Ag-/ConA-stimulated wells and that of unstimulated wells. The data represents the mean ΔSFU from individual animals±SD.

FIG. 13 shows CEA-specific $T_H$ cytokine expression profiles for vaccinated; adjuvant-treated and non-vaccinated CEA.Tg mice, A. Experimental design and immunization schedule. B. Enumeration of rCEA-specific IFN-γ, IL-10 and IL-4 spot forming units (ΔSFUs) from immunized and control mice as measured by ELISPOT™ assays. Histogram bars represent averaged ΔSFU values measured from two independent immunization trials. (n=3 per group). The number of Ag-specific cytokine secreting lymphocytes (ΔSFUs) was calculated by subtracting background values (from weds containing unstimulated cells) from measured values in treated groups. Asterisk denotes statistical significance (P≤0.05; Student-t-test) when compared to the frequency of CEA-specific cytokine secreting cells derived from non-immunized CEA.Tg mice.

FIG. 14 shows vaccination of CEA.Tg mice with the rCEA N domain and poly I:C results in the production of N domain-specific serum IgGs. A. Sera of non-immunized, adjuvant treated or immunized CEA.Tg mice were analyzed by ELISA for the presence of circulating N domain-specific IgG, IgG1 and IgG2a antibody titers. The results represent the mean observed optical density (±SEM) at 450 nm of pooled serum samples (n=12; at a 1:1000 dilution). B. Comparison of individual mice CEA N domain-specific IgG1 and IgG2a titers as determined by ELISA at a serum dilution of 1:1000.

FIG. 15 shows serum from CEA.Tg mice vaccinated with the rCEA N domain display antibody-dependent cellular cytotoxicity (ADCC) and complement dependent cytotoxicity (CDC) cytotoxicity functions towards CEA-expressing cells as well as CEA-specific anti-adhesive properties. Only serum (1:250 dilution) derived from vaccinated CEA.Tg mice can kill CEA-expressing MC38. CEA tumor cells by A. ADCC and B. CDC C. Addition of anti-CEA anti-serum (1:250 dilution) from immunized CEA.Tg mice inhibits CEA-dependent adhesion of MC38.CEA$^{LUC}$ cells to a MC38.CEA monolayer. The pre-incubation of 1 µM of rCEA N domain with the serum of immunized mice reverses the inhibition of CEA-specific cell adhesion of MC38.CEA cells by serum antibodies. NS: not statistically significant when compared to untreated cells. D. Specific inhibition of homotypic binding between recombinant pure rCEA N and $A_3B_3$ domains by the addition of serum (1:1000 dilution) derived from mice immunized with the rCEA N domain. Asterisk denotes statistical significance (P≤0.001) when compared to samples, treated with sera from non-immunized CEA.Tg mice, Student-t-test, Experiments were conducted using pooled serum samples (n=8).

FIG. 20 shows expression of human CEA by adenocarcinoma cell lines used. Immunoblot analyses of the relative CEA-expression profile by (A) murine colonic carcinoma MC38 cell lines (70 kDa band) or (B) human adenocarconma cell lines BxPC3, HT29, MCF-7 and HeLa. Cell lysates from $6 \times 10^4$ cells were resolved on a 7.5% discontinuous Laemmli SDS-PAGE gel and transferred onto nitrocellulose membranes. The presence of CEA was confirmed by Western blot using the CEA N domain-specific mAb Col1 (1:1,000 dilution) followed by an HRP-coupled anti-mouse secondary antibody conjugate (1:1,000 dilution).

DETAILED DESCRIPTION OF THE DISCLOSURE

Figure 1:
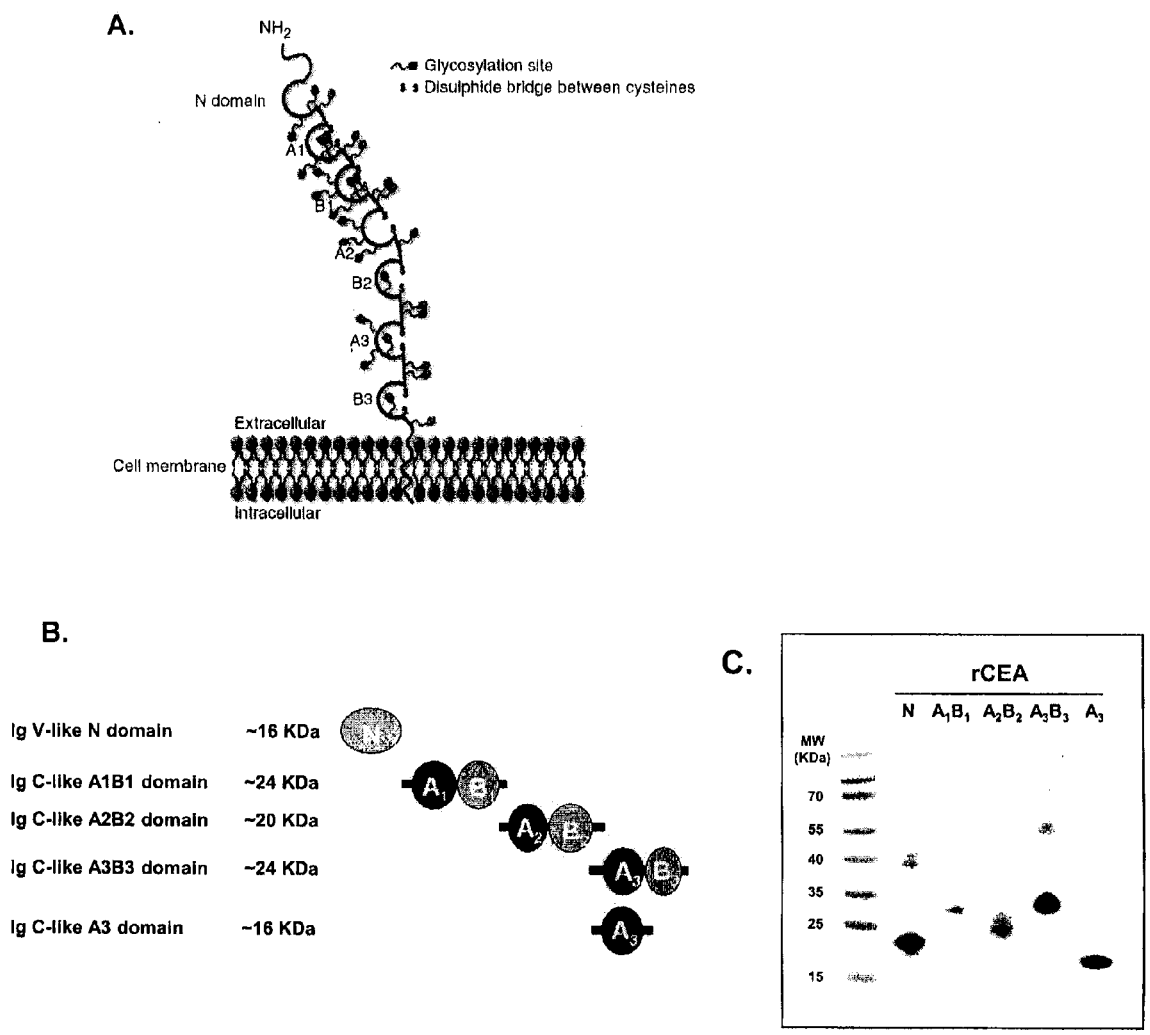
FIG. 1 shows a schematic representation of human carcinoembryonic antigen (CEA) and its expressed recombinant modules. A. Schematic representation of the domain structure of human CEA [Modified from Conaghan et al. 2008]. B. Schematic depiction of the generated rCEA domains as well as their expected molecular weights in kiloDaltons (KDa). C. Coomassie stained SDS-PAGE depicting the purity and molecular weights of the purified rCEA constructs.

The present inventors have shown that intraperitoneal administration of the N-domain of carcinoembryonic antigen (CEA) with adjuvant leads to the production of CEA-specific IFN-γ and IL-4 responses as well as high levels of circulating IgG1 and IgG2a antibodies capable of mediating antibody-dependent tumor lysis. The present inventors further demonstrated that tumor growth was retarded in CEA transgenic (CEA.Tg) mice harboring hCEA-expressing murine tumors leading to improved survival times for these animals. The present inventors also demonstrated that sera and B lymphocytes collected from mice immunized with the N-domain of CEA protected against tumour implantation.

Compositions

Accordingly, the present disclosure provides an immunogenic composition comprising an N-domain of carcinoembryonic antigen (CEA) or a nucleic acid encoding the N-domain and optionally, a pharmaceutically acceptable carrier.

The term "immunogenic composition" as used herein refers to a composition that is able to elicit an immune response, including without limitation, production of antibodies or cell mediated immune responses, against an antigen present in the composition.

In one embodiment, the immunogenic composition further comprises an adjuvant. The term "adjuvant" as used herein refers to a substance that is able to enhance the immunostimulatory effects of the N-domains described herein but does not have any specific antigenic effect itself. Typical adjuvants include, without limitation, Freund's adjuvant, aluminium salts, squalene, poly I:C, poly I:C LC (also known as HILTONOL™ from Oncovir), archaeosomes, virosomes, microsomes, bacterial outer membrane or membrane proteins preparations (OMP), TITERMAX™ adjuvant formulation, Immunostimulatory complexes (ISCOMs), granulocyte-macrophage colony-stimulating factor (GM-CSF), SB-AS2. RIBI™ adjuvant system, Gerbu adjuvant, CpG and monophosphoryl Lipid A. In one embodiment, the adjuvant is poly I:C. In another embodiment, the adjuvant is poly I:C LC.

In one embodiment, the immunogenic composition is a vaccine. The term "vaccine" as used herein refers to an immunogenic composition that is capable of eliciting a prophylactic and/or therapeutic response that prevents, cures or ameliorates disease.

The term "carcinoembryonic antigen" or "CEA" as used herein refers to CEA from any species or source and refers to the 180-kD GPI anchored immunoglobulin (Ig) like glycoprotein. CEA is also known as CEACAM5 or CD66e. The human CEA consists of 651 amino acids and seven distinct Ig domains: the variable N-domain and six constant-domain-like IgC regions (A1, B1, A2, B2, A3 and B3). In one embodiment, the CEA is human CEA. Human CEA has the Genbank accession number NM_004363.2.

The term "N-domain" as used herein refers to an isolated protein that has the immunoglobulin variable-like N-terminal region of the mature CEA protein (i.e. lacking the signal peptide), structurally comprising the IgV-like globular module and, optionally, a spacer sequence that separates the N and A1 IgC-like domains of CEA and minimally containing the immunodominant epitopes of the N-domain and the sequences responsible for adhesion and metastasis, for example, as shown in FIG. 3 and has a sugar structure different from the wild type CEA protein. In one embodiment, the N domain is non-glycosylated. In another embodiment, the N domain has altered glycosylation. In one embodiment, the N-domain comprises the wild type sequence as shown in SEQ ID NO:1 or a tagged wild type sequence as shown in SEQ ID NO:7 or a homolog or analog thereof, or is encoded by the nucleotide sequence as shown in SEQ ID NO:3 or 14 or a homolog or analog thereof. In another embodiment, the N-domain consists of the amino acid sequence of SEQ ID NO:1 or 7. In yet another embodiment, the N-domain comprises a deglycosylated mutant sequence as shown in SEQ ID NO:2 or a homolog or analog thereof, or is encoded by the nucleotide sequence as shown in SEQ ID NO:4 or a homolog or analog thereof. In a further embodiment, the N-domain consists of the amino acid sequence as shown in SEQ ID NO:2. (See Table 1).

The term "homolog" means those amino acid or nucleic acid sequences which have slight or inconsequential sequence variations from the sequences in SEQ ID NOs:1-4, 7 or 14, i.e., the sequences function in substantially the same manner. The variations may be attributable to local mutations or structural modifications. Sequences having substantial homology include nucleic acid sequences having at least 65%, at least 85%, or 90-95% identity with the sequences as shown in SEQ ID NOs:1-4, 7 or 14. Sequence identity can be calculated according to methods known in the art. For example, nucleic acid sequence identity is readily assessed by the algorithm of BLAST version 2.1 advanced search. BLAST is a series of programs that are available online (see world wide web at ncbi.nlm.nih.gov/BLAST). The advanced blast search (see world wide web at ncbi.nlm.nih.gov/blast/blast.cgi?form=1) is set to default parameters. (ie Matrix BLOSUM62; Gap existence cost 11; Per residue gap cost 1; Lambda ratio 0.85 default). References to BLAST searches are: Altschul. S. F., Gish, W., Miller, W., Myers, E. W. & Lipman, D. J. (1990) "Basic local alignment search tool." J. Mol. Biol. 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_141; Altschul, S. F., Madden, T. L., Schäffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656. In addition, homologs of the N-domain of CEA include, without limitation, all CEACAMs that have homologous N-domains in terms of their sequence. Such CEACAMs are typically involved in bacterial infections (adhesion) and bacterial colonization.

The term "analog" means an amino acid or nucleic acid sequence which has been modified as compared to the sequence of SEQ ID NOs:1-4, 7 or 14 wherein the modification does not alter the utility of the sequence (e.g. as an immune activator) as described herein. The modified sequence or analog may have improved properties over the sequences shown in SEQ ID NOs:1-4, 7 or 14. One example of a nucleic acid modification to prepare an analog is to replace one of the naturally occurring bases (i.e. adenine, guanine, cytosine or thymidine) of the sequence with a modified base such as xanthine, hypoxanthine, 2-aminoadenine, 6-methyl, 2-propyl and other alkyl adenines, 5-halo uracil, 5-halo cytosine, 6-aza uracil, G-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecules shown in SEQ ID NO:3, 4 or 14. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

The disclosure also includes sequences that hybridize to the sequences shown in SEQ ID NO:3, 4 or 14 or a fragment thereof and maintain the property of encoding a protein that activates the immune response. The term "sequence that hybridizes" means a nucleic acid sequence that can hybridize to a sequence of SEQ ID NO:3, 4 or 14 under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. The term "stringent hybridization conditions" as used herein means that conditions are selected which promote selective hybridization between two complementary nucleic acid molecules in solution. Hybridization may occur to all or a portion of a nucleic acid sequence molecule. The hybridizing portion is at least 50% the length with respect to one of the polynucleotide sequences encoding a polypeptide. In this regard, the stability of a nucleic acid duplex, or hybrids, is determined by the Tm, which in sodium containing buffers is a function of the sodium ion concentration, G/C content of labeled nucleic acid, length of nucleic acid probe (I), and temperature (Tm=81.5° C.−16.6 (Log 10 [Na+])+0.41 (% (G+C)−600/l). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a greater than 95% identity, the final wash will be reduced by 5° C. Based on these considerations stringent hybridization conditions shall be defined as: hybridization at 5× sodium chloride/sodium citrate (SSC)/5×Denhardt's solution/1.0% SDS at Tm (based on the above equation)-5° C., followed by a wash of 0.2×SSC/0.1% SDS at 60° C.

The N-domains described herein may be modified to contain amino acid substitutions, insertions and/or deletions that do not alter the property of activating the immune response. Conserved amino acid substitutions involve replacing one or more amino acids of the protein with amino acids of similar charge, size, and/or hydrophobicity characteristics. When only conserved substitutions are made the resulting analog should be functionally equivalent to the protein. Non-conserved substitutions involve replacing one or more amino acids of the protein with one or more amino acids which possess dissimilar charge, size, and/or hydrophobicity characteristics.

The N-domains described herein may be modified to make it more therapeutically effective or suitable. For example, the protein may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and toluenesulphonic acids.

The disclosure also includes expression vectors comprising a nucleic acid sequence disclosed herein. Possible expression vectors include but are not limited to cosmids, plasmids, artificial chromosomes, viral vectors or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the disclosure and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The disclosure therefore contemplates a composition comprising a recombinant expression vector of the disclosure containing a nucleic acid molecule of the disclosure, or a fragment thereof, and the necessary regulatory sequences for the transcription and translation of the inserted protein-sequence.

Suitable regulatory sequences may be derived from a variety of sources, including plant, algal, bacterial, fungal, viral, mammalian, or insect genes (for example, see the regulatory sequences described in Goeddel, Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the CEA sequences and/or their flanking regions.

The recombinant expression vectors of the disclosure may also contain a selectable marker gene which facilitates the selection of host cells transformed or transfected with a recombinant molecule of the disclosure. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin optionally IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the disclosure and in particular to determine the effect of a mutation on expression and phenotype. It will be appreciated that selectable markers can be introduced on a separate vector from the nucleic acid of interest.

The recombinant expression vectors may also contain genes which encode a moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The term "transformed host cell" is intended to include cells that are capable of being transformed or transfected with a recombinant expression vector of the disclosure. The terms "transduced", "transformed with", "transfected with", "transformation" and "transfection" are intended to encompass introduction of nucleic acid (e.g. a vector or naked RNA or DNA) into a cell by one of many possible techniques known in the art. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation, microinjection, RNA transfer, DNA transfer, artificial chromosomes, viral vectors and any emerging gene transfer technologies. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

The N domain of CEA may be generated using a variety of systems to yield a non-glycosylated polypeptide. These would include: chemical synthesis of the entire polypeptide; expression of the CEA N domain in mutant Chinese hamster ovary (CHO) cells which are deficient in N-linked glycosylation; expression using cell free expression systems (both prokaryotic and eukaryotic); or expressing the protein in any eukaryotic expression system followed by deglycosylation in vitro.

Suitable host cells include a wide variety of eukaryotic host cells and prokaryotic cells. For example, the proteins of the disclosure may be expressed in algal cells, yeast cells, insect cells, transgenic plant cells, eukaryotic or prokaryotic cell-free expression systems, or mammalian cells. Other suitable host cells can be found in Goeddel, Gene Expression Technology: Methods in Enzymology 185, Academic Press, San Diego, Calif. (1991). In addition, the proteins of the disclosure may be expressed in prokaryotic cells, such as *Escherichia coli* (Zhang et al., Science 303(5656): 371-3 (2004)) or in prokaryotic expression platforms such as Gram positive and lactic acid bacteria, including without limitation, *Streptococcus gordonii, Lactococcus lactis* and *Lactobacillus* spp.

Mammalian cells suitable for carrying out the present disclosure include, among others: 293T cells, COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells.

The mammalian cells can also be derived from a human or animal and include stem cells (including hematopoietic stem cells), somatic cells, progenitor cells (including endothelial progenitor cells), fibroblasts, lymphocytes, and mesenchymal stem cells (MSCs) that have been genetically engineered to express the proteins described herein.

Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)), pMT2PC (Kaufman et al., EMBO J. 6:187-195 (1987)) and pCMV (Clontech, California, U.S.A.). pcDNA and vectors derived thereof (Gateway series; Invitrogen) may also be used.

In another embodiment, the immunogenic compositions described herein further comprise a second CEA domain. In one embodiment, the immunogenic compositions described herein further comprise an $A_3B_3$ IgC-like domain or truncations thereof. The term "$A_3B_3$ IgC-like domain" as used herein refers to the $3^{rd}$ tandem immunoglobulin constant-like region of the human CEA molecule, or homologues thereof. In one embodiment, the $A_3B_3$ IgC-like domain is human and comprises the amino acid sequence of SEQ ID NO:5 or is encoded by the nucleic acid sequence of SEQ ID NO:6. (see Table 2).

Methods and Uses

The present disclosure also provides methods and uses of the immunogenic compositions described herein for inducing or enhancing an immune response, for inhibiting the growth of a CEA-expressing tumour cell, and/or for treating cancer.

Accordingly, the present disclosure provides a method of inducing or an enhancing an immune response against carcinoembryonic antigen (CEA) comprising administering an effective amount of an N-domain of CEA or a nucleic acid molecule encoding the N-domain to an animal or cell in need thereof. The present disclosure also provides a use of an effective amount of an N-domain of CEA or a nucleic acid molecule encoding the N-domain for inducing or enhancing an immune response against CEA in an animal or cell in need thereof. Also provided is a use of an effective amount of an N-domain of CEA or a nucleic acid molecule encoding the N-domain in the preparation of a medicament for inducing or enhancing an immune response against CEA in an animal or cell in need thereof. Further provided is an effective amount of an N-domain of CEA or a nucleic acid molecule encoding the N-domain for use in inducing or enhancing an immune response against CEA in an animal or cell in need thereof.

The present disclosure also provides a method of inducing or enhancing an immune response against CEA comprising administering an effective amount of CEA N-domain specific sera or CEA N-domain specific antibodies to an animal or cell in need thereof. The present disclosure further provides a use of an effective amount of CEA N-domain specific sera or CEA N-domain specific antibodies for inducing or enhancing an immune response against CEA in an animal or cell in need thereof. Also provided is a use of an effective amount of CEA N-domain specific sera or CEA N-domain specific antibodies in the preparation of a medicament for inducing or enhancing an immune response against CEA in an animal or cell in need thereof. Further provided is an effective amount of CEA N-domain specific sera or CEA N-domain specific antibodies for use in inducing or enhancing an immune response against CEA in an animal or cell in need thereof.

The term "inducing an immune response" as used herein refers to activating the immune response. The term "enhancing an immune response" as used herein refers to augmenting an existing immune response.

In one embodiment, the immune response comprises a $T_H2$ response, such as the production of IL-4 and IL-10. In another embodiment, the immune response comprises production of circulating IgG1 and/or IgG2a antibodies.

The term "CEA N-domain specific sera" as used herein refers to sera containing polyclonal antibodies isolated from animals previously immunized with an immunogenic composition disclosed herein.

The term "CEA N-domain specific antibodies" as used herein refers to antibodies or fragments thereof isolated from animals previously immunized with an immunogenic composition disclosed herein.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', F(ab')2, scFv, dsFv, ds-scFv, dimers, minibodies, diabodies, and multimers thereof, multispecific antibody fragments and domain antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Conventional methods can be used to prepare antibodies. For example, by using a N-domain of CEA, polyclonal antisera or monoclonal antibodies can be made using standard methods. A mammal, (e.g., a mouse, hamster, or rabbit) can be immunized with the N-domain which elicits an antibody response in the mammal. Techniques for conferring immunogenicity include conjugation to carriers or other techniques well known in the art. For example, the N-domain can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256:495-497, 1975) as well as other techniques such as the human B-cell hybridoma technique (Kozbor and Roder, Immunology Today 4:3, 72-79, 1983), the Epstein-Barr virus (EBV)-hybridoma technique to produce human monoclonal antibodies (Cole et al., "The EBV-Hybridoma Technique and its Application to Human Lung Cancer" in "Monoclonal Antibodies in Cancer Therapy", Allen R. Bliss, Inc. (1985), pages 77-96) and screening of combinatorial antibody libraries (Huse et al. Science 246:4935, 1275-1282, 1989). Hybridoma cells can be screened immunochemically for production of antibodies specifically reactive with the N-domain and the monoclonal antibodies can be isolated. Therefore, the disclosure also contemplates hybridoma cells secreting monoclonal antibodies with specificity for N-domain.

Chimeric antibody derivatives, i.e., antibody molecules that combine a non-human animal variable region and a human constant region are also contemplated. Chimeric antibody molecules can include, for example, the antigen binding domain from an antibody of a mouse, rat, or other species, with human constant regions. Conventional methods may be used to make chimeric antibodies containing the immunoglobulin variable region which recognizes the N-domain (See, for example, Morrison et al. (PNAS 81:21, 6851-6855, 1984), and Takeda et al. (Nature 314:452-454), and the patents of Cabilly et al., U.S. Pat. No. 4,816,567; Boss et al., U.S. Pat. No. 4,816,397; Tanaguchi et al., European Patent Publication No. EP171496; European Patent Publication No. 0173494, United Kingdom patent GB 2177096B).

Monoclonal or chimeric antibodies specifically reactive with an N-domain of CEA as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al. (1983) Proc. Natl. Acad. Sci. 80:12, 7308-7312), Kozbor and Roder (1983) Immunology Today 4:3, 72-79; Olsson et al. (1982) Methods in Enzymol. 92, 3-16, PCT Patent Application Publication No. WO92/06193 and EP Patent Application Publication No. 0 239 400). Humanized antibodies can also be commercially produced (Scotgen Limited, 2 Holly Road, Twickenham, Middlesex, Great Britain.)

Specific antibodies, or antibody fragments, reactive against an N-domain of CEA may also be generated by screening expression libraries encoding immunoglobulin genes, or portions thereof, expressed in bacteria with peptides produced from the nucleic acid molecules encoding an N-domain of CEA. For example, complete Fab fragments, VH regions and FV regions can be expressed in bacteria using phage expression libraries (See for example Ward et al. (1989) Nature 348:544-546, Huse et al. (1989) Science 246:4935, 1275-1282, and McCafferty et al. (1989) Nature 348, 552-555).

Antibodies may also be prepared using DNA immunization. For example, an expression vector containing a nucleic acid encoding an N-domain of CEA may be injected into a suitable animal such as mouse. The protein will therefore be expressed in vivo and antibodies will be induced. The antibodies can be isolated and prepared as described above for protein immunization.

The present disclosure also provides a method of inhibiting the growth of a carcinoembryonic antigen (CEA)-expressing tumour cell comprising administering an effective amount of an N-domain of CEA or a nucleic acid molecule encoding the N-domain to an animal or cell in need thereof. Also provided is a use of an effective amount of an N-domain of CEA or a nucleic acid molecule encoding the N-domain for inhibiting the growth of a CEA-expressing tumour cell in an animal or cell in need thereof. Further provided is a use of an effective amount of an N-domain of CEA or a nucleic acid molecule encoding the N-domain in the preparation of a medicament for inhibiting the growth of a CEA-expressing tumour cell in an animal or cell in need thereof. Even further provided is an effective amount of an N-domain of CEA or a nucleic acid molecule encoding the N-domain for use in inhibiting the growth of a CEA-expressing tumour cell in an animal or cell in need thereof.

Also provided herein is a method of inhibiting growth of a CEA-expressing tumour cell comprising administering an effective amount of CEA N-domain specific sera or CEA N-domain specific antibodies to an animal or cell in need thereof. Also provided is a use of an effective amount of CEA N-domain specific sera or CEA N-domain specific antibodies for inhibiting the growth of a CEA-expressing tumour cell in an animal or cell in need thereof. Further provided is a use of an effective amount of CEA N-domain specific sera or CEA N-domain specific antibodies in the preparation of a medicament for inhibiting the growth of a CEA-expressing tumour cell in an animal or cell in need thereof. Even further provided is an effective amount of CEA N-domain specific sera or CEA N-domain specific antibodies for use in inhibiting the growth of a CEA-expressing tumour cell in an animal or cell in need thereof.

The phrase "inhibiting the growth of a CEA-expressing tumour" as used herein refers to slowing down the growth of the tumour cells and/or killing the tumour cell. In one embodiment, the tumor cells are killed by complement-mediated lysis or by antibody-depedent cytotoxicity (ADCC).

Also provided herein is a method of treating a subject with carcinoembryonic antigen (CEA)-associated cancer or an increased risk of said cancer comprising administering an effective amount of an N-domain of CEA or a nucleic acid molecule encoding the N-domain. The disclosure further provides a use of an effective amount of an N-domain of CEA or a nucleic acid molecule encoding the N-domain for treating a subject with carcinoembryonic antigen (CEA)-associated cancer or an increased risk of said cancer. Also provided is a use of an effective amount of an N-domain of CEA or a nucleic acid molecule encoding the N-domain in the preparation of a medicament for treating a subject with carcinoembryonic antigen (CEA)-associated cancer or an increased risk of said cancer. Further provided is an effective amount of an N-domain of CEA or a nucleic acid molecule encoding the N-domain for use in treating a subject with carcinoembryonic antigen (CEA)-associated cancer or an increased risk of said cancer.

Also provided herein is a method of treating a subject with CEA-associated cancer or an increased risk of said cancer comprising administering an effective amount of CEA N-domain specific sera or CEA N-domain specific antibodies to an animal or cell in need thereof. The disclosure further provides a use of an effective amount of CEA N-domain specific sera or CEA N-domain specific antibodies for treating a subject with carcinoembryonic antigen (CEA)-associated cancer or an increased risk of said cancer. Also provided is a use of an effective amount of CEA N-domain specific sera or CEA N-domain specific antibodies in the preparation of a medicament for treating a subject with carcinoembryonic antigen (CEA)-associated cancer or an increased risk of said cancer. Further provided is an effective amount of CEA N-domain specific sera or CEA N-domain specific antibodies for use in treating a subject with carcinoembryonic antigen (CEA)-associated cancer or an increased risk of said cancer.

The term "administering an N-domain" includes both the administration of the protein as well as the administration of a nucleic acid sequence encoding the protein to an animal or to a cell in vitro or in vivo. The term "administering" also includes the administration of a cell that expresses the protein.

The N-domains described herein may be administered in vivo or ex vivo to a cell which is then administered. For example, cells may be transformed or transduced with the nucleic acid encoding the protein described herein and then the cells are administered in vivo.

The term "treating" or "treatment" as used herein means administering to a subject a therapeutically effective amount of the compositions of the present disclosure and may consist of a single administration, or alternatively comprise a series of applications.

As used herein, and as well understood in the art, "treatment" or "treating" is also an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. Further any of the treatment methods or uses described herein can be formulated alone or for contemporaneous administration with other agents or therapies. "Treatment" or "treating" can also include preventing the onset of disease.

The term "subject" or "animal" as used herein includes all members of the animal kingdom including mammals, suitably humans including patients.

The term "increased risk of cancer" as used herein means a subject that has a higher risk of developing a particular cancer than the average risk of the population. A subject may have a higher risk due to previously having had said particular cancer and or having a genetic risk factor for said particular cancer.

In another embodiment, the CEA-associated cancer is a cancer caused by CEA-expressing tumor cells. In an embodiment, the cancer is of the gastrointestinal tract, breast, lung, colorectal, pancreas, female reproductive tract, such as cervical, ovarian or uterine, neuroblastoma, Hodgkin's disease, non-Hodgkin's lymphoma, sarcoma, cutaneous malignancies or medullary thyroid carcinoma.

In another embodiment, the methods and uses described herein further comprise coadministration of a second CEA domain. In one embodiment, the methods and uses described herein further comprise coadministration or use of the $A_3B_3$ IgC-like domain or truncations thereof. In one embodiment, the $A_3B_3$ IgC-like domain is human and comprises the amino acid sequence of SEQ ID NO:5 or is encoded by the nucleic acid sequence of SEQ ID NO:6. (see Table 2).

In yet another embodiment, the methods and uses described herein further comprise using or administering an adjuvant. As described herein, typical adjuvants include, without limitation, Freund's adjuvant, aluminium salts, squalene, poly I:C, poly I:C LC, archaeosomes, virosomes, microsomes, OMP preparations, TITERMAX™ adjuvant formulation, ISCOMs, GM-CSF, SB-AS2, RIBI™ adjuvant system, Gerbu adjuvant, CpG and monophosphoryl Lipid A. In one embodiment, the adjuvant is poly I:C. In another embodiment the adjuvant is poly I:C LC.

In all of the above therapeutic applications, the protein can be administered as a protein or as a nucleic acid molecule encoding the protein. In one embodiment, as noted above, expression of the protein occurs as a result of the administration of nucleic acid encoding the protein to an organism. Thus, the protein will be produced endogenously in the organism, rather than administered in a protein form. The therapy may be done at an embryonic stage of the organism, such that the germ cells of the organism contain the protein nucleic acid, resulting in a transgenic organism, or at a later stage of development to specific somatic cells, such that only a particular tissue or portion of a tissue contains the protein nucleic acid. Techniques for nucleic acid therapy are well known in the art, as are the techniques for the creation of transgenic organisms (Carl A. Pinkert. Transgenic Animal Technology: A Laboratory Handbook. Academic Press; 1st edition (1994)).

It is to be understood that the administration of the protein nucleic acid in gene therapy may take several forms, all of which are included in the scope of the present disclosure. The nucleic acid encoding the protein may be administered in such a manner as to add the protein nucleic acid to the genome of the cell or the organism. For example, administering a nucleic acid encoding the protein, under the control of a promoter which results in an increase in expression of the protein, results in the incorporation of the nucleic acid into the genome of the cell or the organism, such that increased levels of the protein are made.

Construction of appropriate expression vehicles and vectors for therapeutic applications will depend on the organism to be treated and the purpose of the gene therapy. The selection of appropriate promoters and other regulatory DNA will proceed according to known principles, based on a variety of known gene therapy techniques. For example, retroviral mediated gene transfer is a very effective method for therapy, as systems utilizing packaging defective viruses allow the production of recombinants which are infectious only once, thus avoiding the introduction of wild-type virus into an organism. Alternative methodologies for therapy include non-viral transfer methods, such as calcium phosphate co-precipitation, mechanical techniques, for example microinjection, membrane fusion-mediated transfer via liposomes, as well as direct DNA uptake and receptor-mediated DNA transfer.

Assays

The present inventors have utilized a modified MC38.CEA cell line that expresses firefly Luciferase and GFP previously described in Tiscornia et al. 2006 to measure CEA homophilic interactions. Accordingly, the present disclosure further provides an in vitro screening assay for identifying inhibitors of CEA-mediated homophilic interactions comprising incubating MC38.CEA$^{LUC}$ cells with a monolayer of non-luminescent M38.CEA cells in the presence of a test compound; and assessing cell adherence by quantifying bioluminescence signal emitted by adhered MC38.CEA$^{LUC}$ cells, wherein a decrease in bioluminescence compared to a control indicates that the test compound is an inhibitor of CEA-mediated homophilic interactions.

The term "control" as used herein refers to cells in the absence of test compound. The control can also be a predetermined standard or reference range of values.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Generation of Folded rCEA Modules

FIG. 1 panel B and C shows the different rCEA constructs expressed and purified to date from *E. coli*. By optimizing the expression and purification protocols, high yields of purified proteins were achieved, typically 10 mg of soluble recombinant protein per 100 ml culture from a single poly-histidine affinity chromatography step using Ni-NTA agarose beads.

Figure 2:
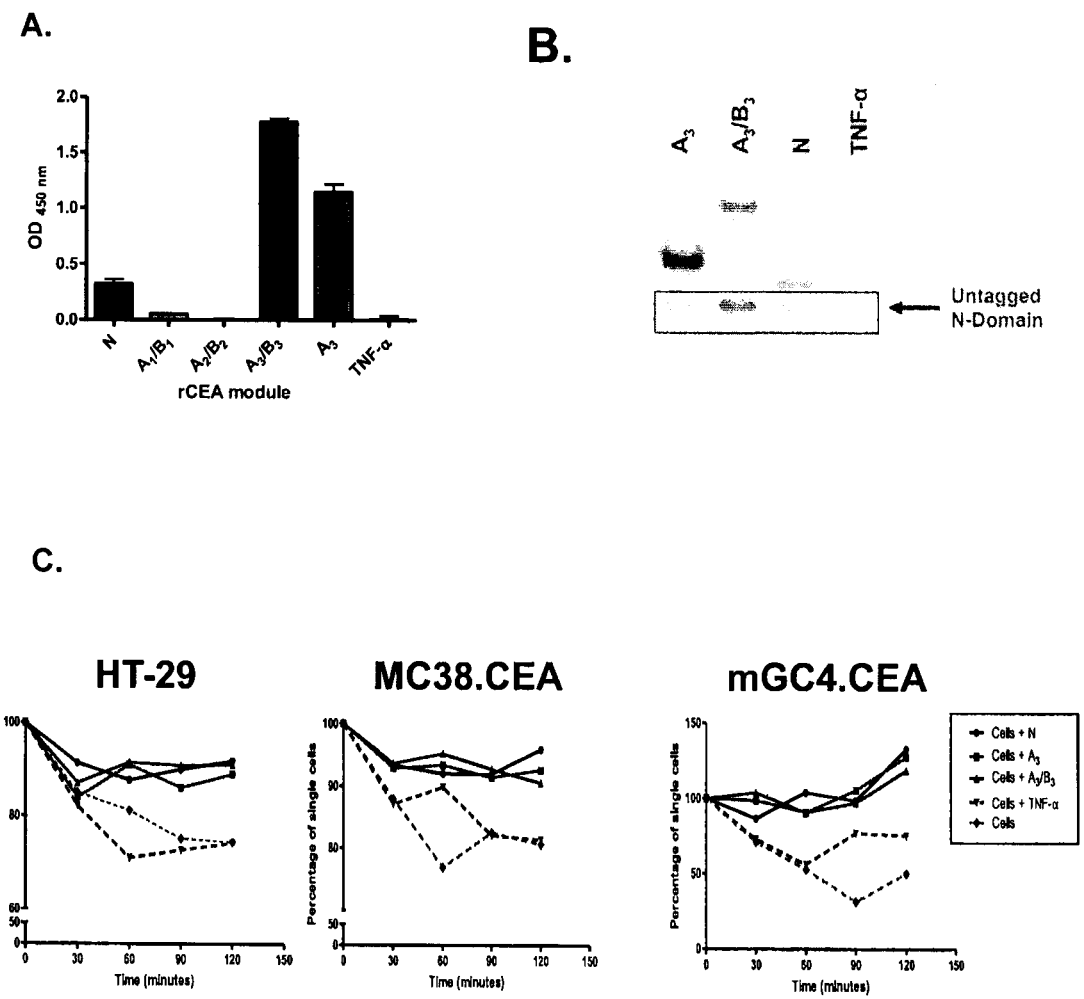
FIG. 2 shows purified human recombinant CEA retain their cell adhesive properties. A. Demonstration of homotypic rCEA interactions using an ELISA-based protein binding assay. Ninety six wells polystyrene plates were coated with untagged rCEA N-domain (1 mg per well) and incubated with either His-tagged rCEA modules or non-specific proteins (bovine serum albumin (BSA) and tumor necrosis factor (TNF)-α). The presence of bound His-tagged protein was determined using HRPO-coupled anti-His mAb (His1; 1:5000 dilution). B. Pull-down using magnetic Ni-NTA beads showing the specific interaction of untagged wild-type (WT) rCEA N domain with His-tagged rCEA modules. TNF-α was used as a control protein which did not pull down untagged rCEA N domain. C. Reversal of CEA-mediated cell aggregation kinetics. CEA expressing cells human colorectal adenocarcinoma-(HT-29) as well as CEA-expressing murine colorectal and gastric adenocarcinoma cell lines (MC38.CEA and mGC4.CEA, respectively) were detached from their substratum and incubated in suspension with either the rCEA modules (N, $A_3/B_3$ or $A_3$) or an irrelevant protein (TNF-α) at a ratio of 1 mg protein per $10^6$ cells per mL.

CEA domains were purified to homogeneity under denaturing conditions. Interactions between the N domain to itself and to the A$_3$B$_3$ domain were initially tested to confirm proper folding. The remaining CEA modules (FIG. 1 panels B and C) were also expressed and their lack of binding to the N domain was confirmed using an ELISA-based binding assay. FIG. 2 A shows the specific binding of the N domain either to itself, to A$_3$B$_3$ or the A$_3$ domain, but not to other CEA domains or TNF-α (irrelevant protein control). The observed domain interactions were confirmed by pull-down assay, whereby the untagged N domain is released with 8 M urea from magnetic Ni-NTA beads coated with either His-tagged rCEA N, A$_3$ or A$_3$B$_3$ modules; but not from beads coated with His-tagged TNF-α (FIG. 2 B).

Lastly, CEA-mediated intercellular aggregation assay was used [Benchimol et al. 1989, Zhou et al. 1993] and it was tested if soluble rCEA domains could disaggregate HT-29 human colorectal adenocarcinoma cells in suspension. FIG. 2C shows the inhibition of CEA-mediated interactions following the addition of the N, A$_3$B$_3$ or the A$_3$ domains but not by TNF-α.

Together, these observations validated that the generated rCEA N module was properly folded and capable of mediating CEA-CEA homotypic interactions.

Culture of CEA-Expressing Tumor Xenografts:

Two CEA expressing murine cell lines (as well as their CEA null background cells that are compatible with the CEA.Tg mouse strain) were acquired. The murine gastric cancer cell line mGC4.CEA, as well as its, CEA negative cell line (mGC8) was acquired from Dr. Wolfgang Zimmerman (Tumor Immunology Laboratory, LIFE-Center, Klinikum Grosshadern, Ludwig-Maximilians-University; Germany). The MC38.CEA and its CEA null background (MC38) was acquired from Dr. Jeffrey Schlom (Laboratory of Tumor Immunology and Biology, National Cancer Institute, NIH; Bethesda, Md.). Analysis of CEA expression profile showed that the mGC4.CEA was a low expresser, whereas MC38.CEA was a high expresser. Moreover, both cell lines were found to be susceptible to inhibition of CEA-mediated intercellular aggregation following the addition of the N, A$_3$, and A$_3$B$_3$ modules in a manner similar to HT-29 cells (FIG. 2C).

Establishment of a CEA.Tg Mouse Colony:

CEA.Tg mice were acquired from Dr. Wolfgang Zimmerman (Tumor Immunology Laboratory, LIFE-Center, Klinikum Grosshadern, Ludwig-Maximilians-University; Germany). Generation of CEA positive litters was done by backcrossing CEA positive animals with C57BL/6 mice. However, challenges were experienced in generating ample numbers of this mouse strain caused as a result of a lower reproductive rate and the paucity of CEA positive offsprings. Nevertheless, a stable breeding program was successfully maintained, where 25-33% of the progeny being CEA positive litters, with litter sizes ranging from 4-6 pups (compared to 1-3).

Engineering a Mutant rCEA N Domain to Test as a Candidate Vaccinogen:

Originally, injecting rCEA modules O-glycosylated with GalNAc was considered. For that purpose, a mutant rCEA N-domain (FIG. 3) was engineered that retained all the putative immuno-dominant epitopes as well as the sequences responsible for mediating its homotypic adhesive properties.

Following extensive testing, it was found that human CEA incorporated 1 (±2) GalNAc groups. Nonetheless, the usefulness of the mutant CEA N domain, lacking GalNAc groups, was tested in surmounting immunological anergy towards CEA in CEA.Tg mice.

Testing the Therapeutic Potential of rCEA:

Having satisfied the two main priorities (i.e. generating folded rCEA modules and setting up a CEA.Tg mouse model), an immunization trial was conducted to determine the feasibility of surmounting immunological tolerance to CEA in CEA.Tg mice. Furthermore, it was needed to determine whether immunization with the N domain can interfere with the growth of implanted MC38.CEA tumor xenografts.

To that end, twenty four 12 weeks-old CEA.Tg mice were subdivided between three groups of eight animals each. One group was left as an untreated control group, one group of animals received the WT CEA N domain whereas the last group received the mutant CEA N domain. Half a million ($5\times10^5$) MC38.CEA cells were subcutaneously implanted into each animal. On days six and thirteen following xenograft implantation, the mice received an intraperitoneal injection of 100 µg of rCEA N domain admixed with 100 µg poly I:C. Poly I:C was used as adjuvant because of its capacity to stimulate both B cell activation [Scher et al. 1973] as well as type 1 responses through TLR-3/7 signaling [Barchet 2008], a combination of immune responses that have been shown to positively influence the development of protective anti-tumor immune responses in mice and in clinical trials [Barchet 2008]. The inherent antigenicity of purified human CEA has not been reported in the past. Thus the intraperitoneal route of injection was used, since the immunogenicity of a given antigen is traditionally determined following its administration via intraperitoneal injections [Garvey et al. 1983].

Figure 4:
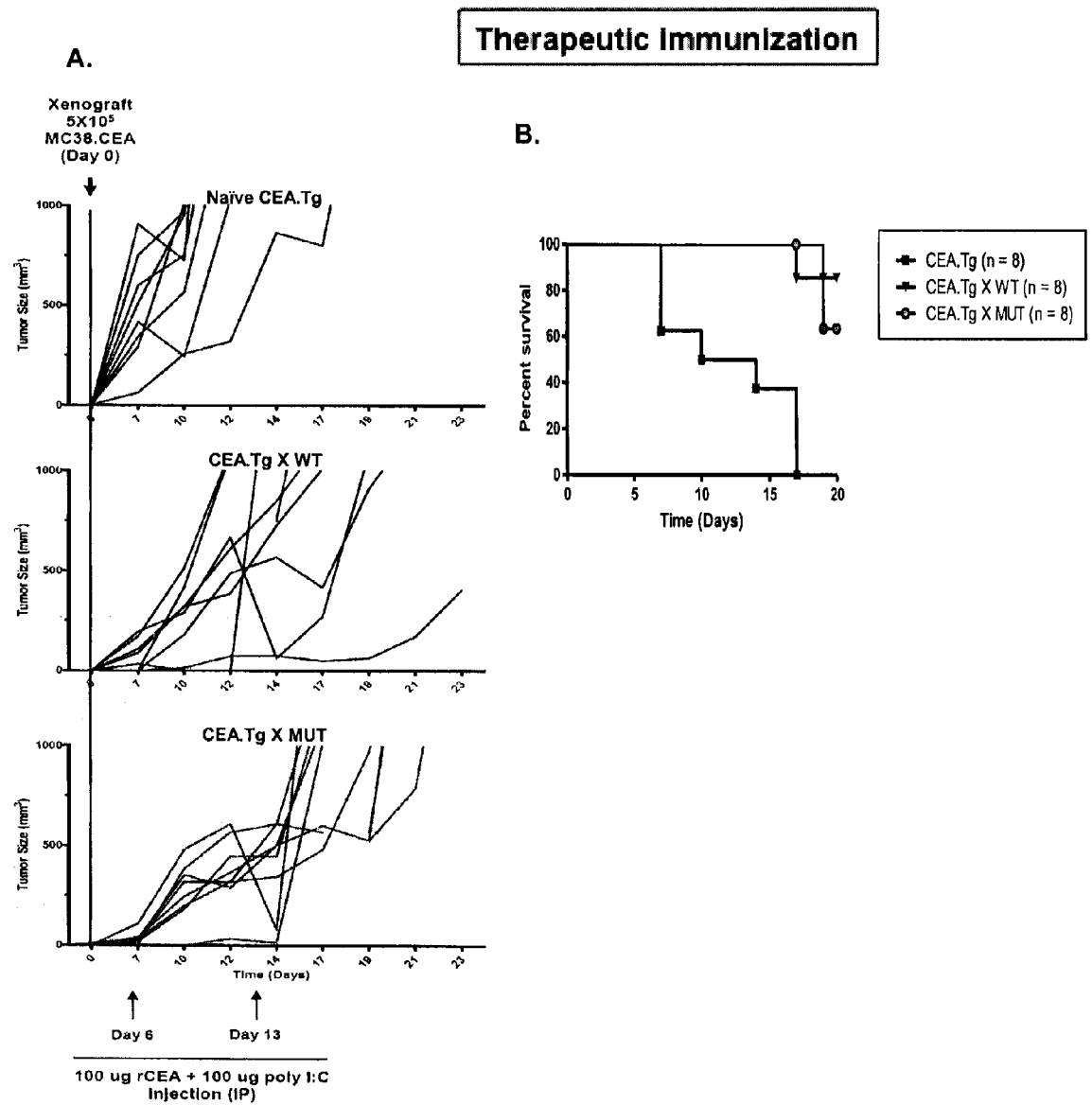
FIG. 4 shows control of the growth of an aggressive tumor following the administration of endotoxin-free rCEA WT or mutant N domains as therapeutic vaccines. A. Tumor growth in CEA.Tg mice (8 per group) following the administration of rCEA N domain. Each ascending line represents a single mouse. Eight to twelve weeks-old CEA.Tg mice were subcutaneously implanted with $5\times10^5$ MC38.CEA cells in the right hind leg. Treated mice received an IP injection of 100 mg rCEA admixed with 100 mg poly I:C (Sigma-Aldrich) at day 6 post xenograft implantation. Animals were boosted a week later with 100 mg rCEA admixed with 100 mg poly I:C at day 13. B. Kaplan-Meier curve depicting the survival rates of CEA.Tg mice from different groups. Despite the aggressive growth of the MC38.CEA tumor xenografts, it did not kill the animals. However, animals displaying ulceration at the site of tumor growth and/or reaching a tumor diameter ≥15 mm were euthanized as per institutional animal care ethics guidelines.

FIG. 4 A shows the progression of tumor volume in immunized and control CEA.Tg mice. The development of tumor volumes that are $\geq 750$ mm$^3$ occurred within 7 to 14 days in 100% of control mice implanted with $5\times10^5$ MC38.CEA cells. Nonetheless, significant retardation of tumor growth was observed following the intraperitoneal injection of endotoxin-free WT and mutant rCEA N domains (FIG. 4 A). The effects of this vaccine formulation (N domain+poly I:C) were pronounced in 25% of animals receiving either Ag, in that significant drops in tumor volumes were observed following injections (FIG. 4 A). Furthermore, injection of this formulation did not exert overt signs of toxicity/pathology. Finally, the intraperitoneal administration of rCEA N domain significantly improved survival rate (FIG. 4B). It is important to outline that despite the aggressive growth of the MC38.CEA tumor xenografts, implantation of this cell line did not kill the animals. However, animals displaying ulceration at the site of tumor growth and/or a tumor diameter $\geq 15$ mm were euthanized as per institutional animal care ethics guidelines.

Taken together, these findings suggest that the intraperitoneal injection of endotoxin-free WT or mutant rCEA N modules with poly I:C overcame immunological tolerance to CEA and was efficient in significantly reducing tumor growth.

Figure 5:
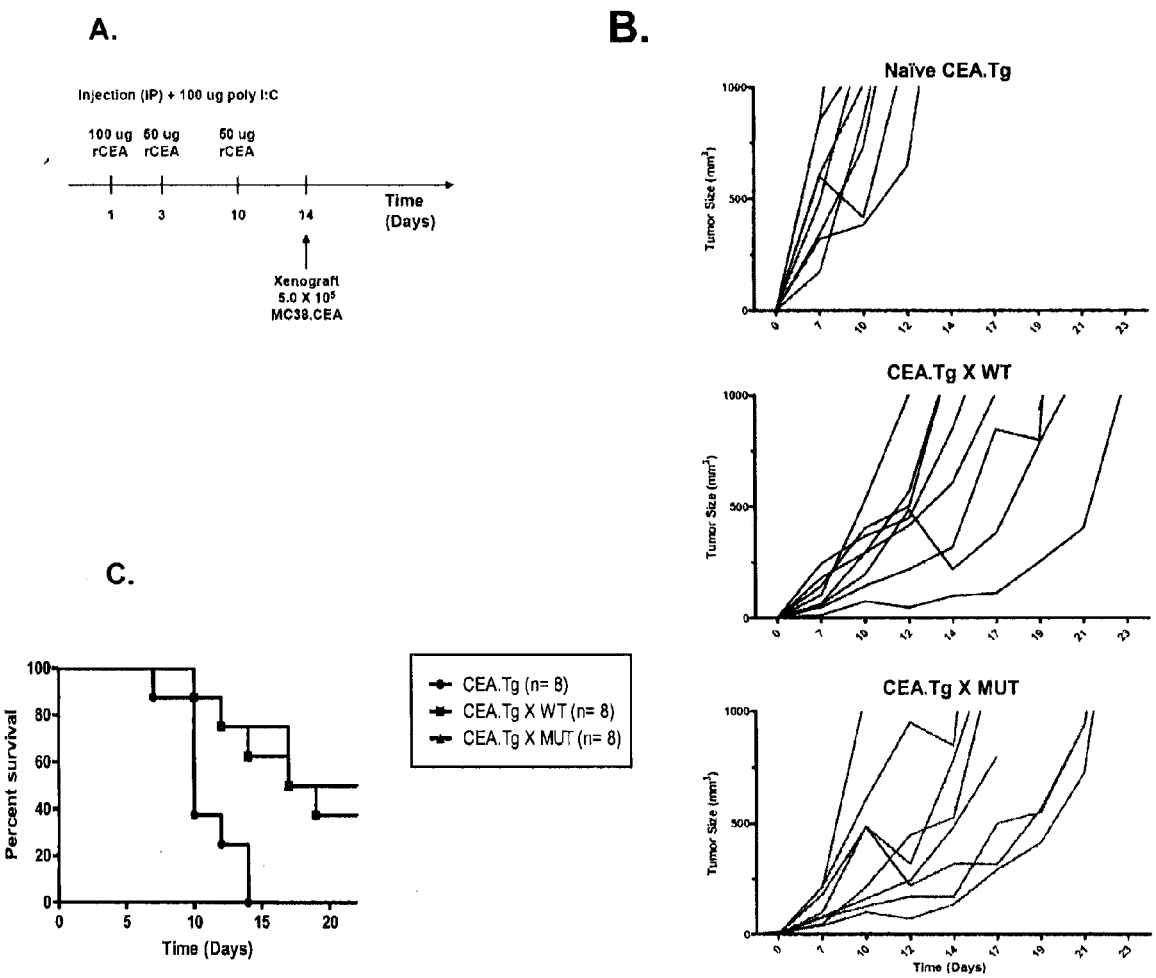
FIG. 5 shows prophylactic administration of endotoxin-free rCEA WT or Mut N domains results in the retardation of tumor growth in immunized CEA.Tg mice. A. Outline of experimental schedule. Eight to twelve weeks-old CEA.Tg mice were primed by intraperitoneal injection of 100 mg rCEA admixed with 100 mg poly I:C (Sigma-Aldrich) and boosted IP on days 3 and 10 with 50 mg rCEA admixed with 100 mg poly I:C. Four days following the last immunization, the mice were challenged with $5\times10^5$ MC38.CEA subcutaneously implanted as a xenograft in the right hind leg. B. Tumor growth in CEA.Tg mice (8 per group) following the prophylactic administration of endotoxin-free rCEA N domain. Each ascending line represents a single mouse. C. Kaplan-Meier curve depicting the survival rates of CEA.Tg mice from different groups. Despite the aggressive growth of the MC38.CEA tumor xenografts, it did not kill the animals. However, animals displaying ulceration at the site of tumor growth and/or reaching a tumor size ≥15 mm were euthanized as per institutional animal care ethics guidelines.

Testing the Prophylactic Potential of rCEA:

CEA-based vaccines are best discussed in the context of interfering with the process of tumor metastasis. Having observed the effect of CEA-based immunization on retarding tumor growth, it was also of interest in determining if the vaccine carried the prophylactic potential of preventing the establishment of CEA-expressing tumor cells. As such, 24 twelve weeks old CEA.Tg mice were subdivided into three groups, each containing eight mice. Two groups received endotoxin-free rCEA WT or mutant N domains, or were left as untreated controls (FIG. 5). Four days following the last immunization step, $5\times10^5$ MC38.CEA cells were subcutaneously implanted as xenografts and the growth of tumors were measured with calipers. Although the immunization did not prevent the implanted tumor xenografts from establishing, it did nonetheless significantly retard their growth (FIG. 5 B) and significantly prolong survival (FIG. 5 C) in a manner reminiscent of that observed with the therapeutic administration of the CEA vaccine formulation (FIG. 4).

Characterization of the Engendered CEA-Specific Immune Responses:

In light of the observed tumor retardation, the underlying immunological mechanisms were analyzed. To that effect, twelve weeks old mice were subdivided into four groups: two groups of four CEA.Tg mice immunized with either endotoxin-free WT or mutant rCEA N domain using the schedule outlined in FIG. 5A; one group of two C57BL/6 mice injected with the WT rCEA N domain using the schedule outlined in FIG. 5A, and lastly an unimmunized control group containing four CEA.Tg mice.

Four days following the last immunization, the animals were sacrificed and their blood and spleens collected to analyze correlates of immune responses.

Cellular Responses:

Spleen leukocytes from immunized and control mice were collected, suspended to a final density of $10^6$ cells per mL and stimulated ex vivo with either concanavalin A (ConA; 5 µg per mL; Sigma-Aldrich), the full length tumor glycoform of human CEA (1 µg per mL; Sigma-Aldrich), rCEA WT N domain (1 µg per mL) or left as unstimulated controls. Cell viability following harvest was $\geq 95\%$.

Cytokine ELISPOT™ was performed using the splenocytes from immunized and control mice to monitor the frequency of CEA-specific IFN-γ, IL-10 and IL-4 spot-forming units (SFU) in order to determine the vaccine induced $T_H$ polarity. Cells derived from unimmunized CEA.Tg mice (referred to as naive) did not produce any of the above cytokines in response to antigenic stimulation with CEA, but did so following mitogenic stimulation with ConA (FIG. 6). Conversely, CEA-immunized C57BL/6 mice produced all three cytokines in response to antigenic stimulation (FIG. 6), albeit at lower levels, which comes in agreement with the observations of Woo et al. [Woo et al. 2008]. CEA.Tg mice immunized with the WT rCEA N domain produced equal levels of IL-4, IL-10 and IFN-γ SFUs following stimulation with either rCEA N domain or FL-CEA (FIG. 6), whereas CEA.Tg mice immunized with the mutant rCEA N domain produced IL-4 and IL-10, but not IFN-7 (FIG. 6). This disparity in Ag-specific cytokine production was observed in all animals comprising these experimental cohorts and with both forms of CEA (recombinant and tumor glycoform). Consistent with these observations, little or no proliferation of splenocytes derived from immunized and control mice was seen in response to antigenic stimulation thereby suggesting a minor stimulation of T cells by this immunization strategy.

Figure 7:
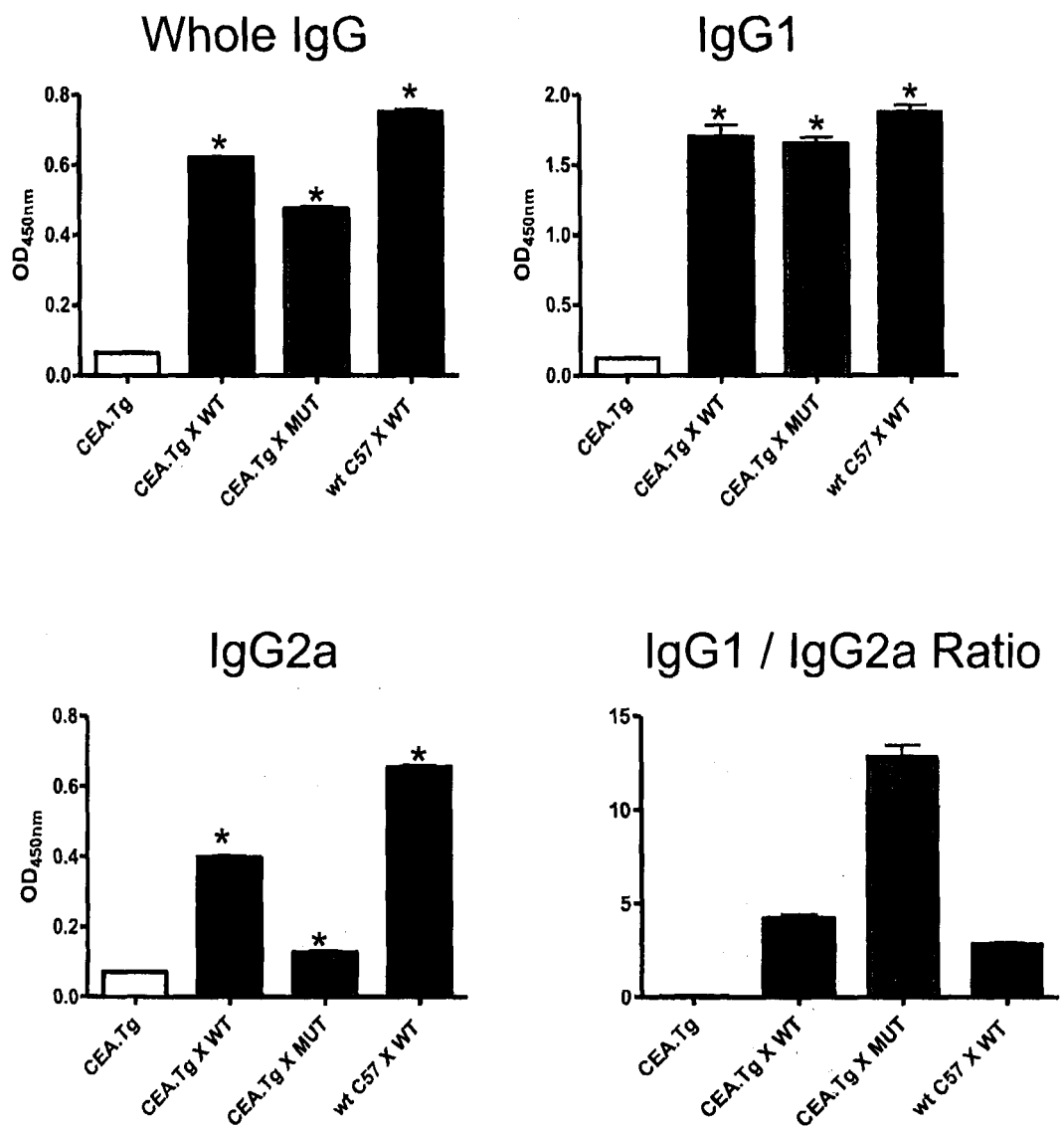
FIG. 7 shows stimulation of IgG1 and IgG2a production following the intraperitoneal administration of rCEA N domain. Serum was collected from CEA-immunized and control mice 4 days following the last immunization and tested for the presence of CEA N domain-specific IgG, IgG1 and IgG2a antibodies by indirect ELISA. The results represent the observed optical density of anti-CEA WT N domain pooled serum samples at a 1:1000 dilution. Significant when compared to non-immunized, *P≤0.01; Student-t-test.

Humoral Responses:

Since the observed CEA-specific cytokine expression profile was reminiscent of $T_H2$ immune responses, the serum of immunized and control animals was analyzed for the presence of CEA-specific antibodies. Using the WT rCEA N domain as capture antigen in an indirect ELISA, high levels of rCEA-specific IgG serum antibodies were detected (FIG. 7). Analysis of the CEA-specific IgG subclass revealed the presence of high levels of CEA-specific IgG1 antibodies and some IgG2a (FIG. 7). Interestingly, the relatively higher levels of CEA-specific IgG2a produced in CEA.Tg and C57BL/6 mice immunized with WT N domain (FIG. 7) correlated with production of IFN-γ by these animals (FIG. 6).

Finally, the stimulation of CEA-specific IgG1 antibodies led the present inventors to ask the question if they could interfere with CEA-mediated intercellular adhesion events or mediate the killing of tumor cells by either complement-mediated lysis or by antibody-dependent cytotoxicity (ADCC). Incubation of MC38.CEA cells with sera from vaccinated mice did not result in a significant reduction of CEA-mediated intercellular aggregations; rather it further augmented aggregate formation. This outcome was not unexpected since co-incubation of polyclonal antibodies with their cognate antigen (presented as particulate Ag) results in an Ag-Ab lattice formation.

Figure 8:
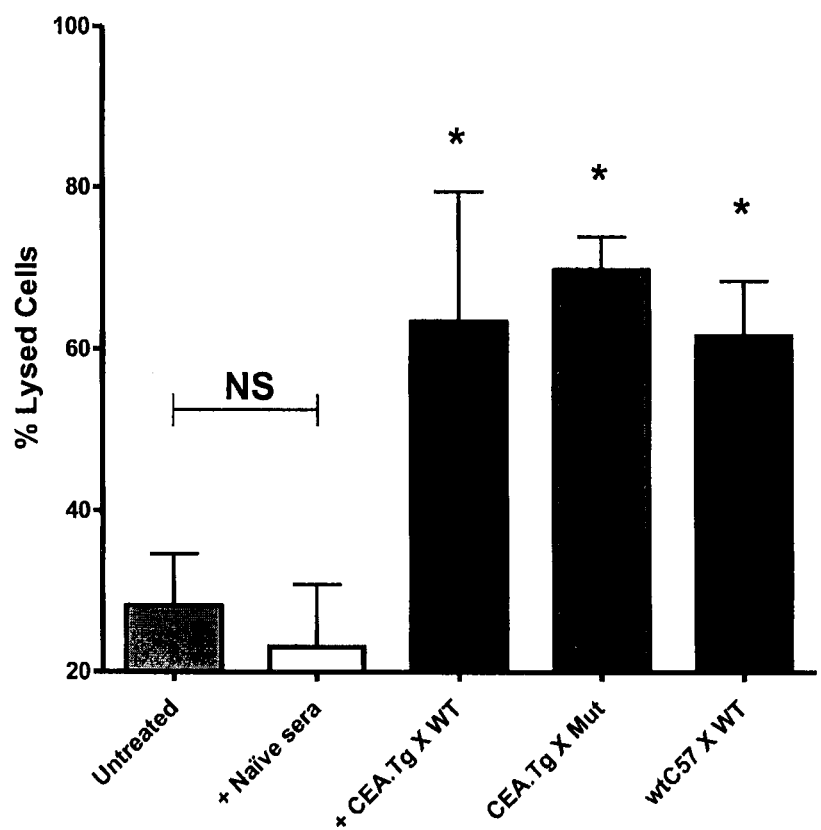
FIG. 8 shows complement-dependent lysis of tumor cells. MC38.CEA cells were suspended at a density of $1\times10^5$ cells per mL in either PBS alone or PBS supplemented with rabbit complement (1:100 final dilution; Cedarlane labs) and treated with sera from immunized or control mice (1:100 final dilution). Cell suspensions were incubated for one hour at 37° C. and the percentage of lysed cells was assessed by Trypan blue dye exclusion. NS; statistically insignificant when compared to untreated cells. Significant when compared to cells treated with complement and sera from naïve CEA.Tg mice, *P≤0.01; Student-t-test.

In order to investigate the efficacy of the vaccine-stimulated antibodies in mediating complement-dependent lysis, MC38.CEA cells were incubated with rabbit complement (1:100 dilution) and serum from either immunized or control animals (1:100 dilution). Significant lysis was observed when cells were co-incubated with complement and serum from immunized CEA.Tg or C57BL/6 mice (FIG. 8). On the other hand, incubation of MC38.CEA cells with complement and serum from non-immunized (naïve) mice did not result in cell lysis (FIG. 8).

In summary, the protein expression and purification protocol that was developed allowed generation of properly folded CEA domains capable of mediating homotypic interactions as well as interfering with CEA-mediated intercellular adhesions. Second, the vaccine formulation and route of injection were sufficient in overcoming immunological tolerance against CEA in CEA.Tg mice. Although the engendered immune response appeared to be mainly a humoral response ($T_H2$), it did nonetheless result in curbing the growth of a very aggressive tumor xenograft.

Example 2

Materials and Methods

Cloning, Expression, and Purification of rCEA Modules

The human CEA cDNA open reading frame was purchased from Genecopoeia Inc (GermanTown, Md.) and was used as a cloning template. The CEA N domain (amino acids 1-132) that included an N-terminal His-tag and TEV cleavage site was amplified using the CEA-N forward primer (5'-GCGATA CAT ATG CAT CAT CAC CAT CAC CAT GAA AAC CTC TAT TTC CM MG CTC ACT ATT GM TCC ACG CCG TTC MT-3') (SEQ ID NO:8) and the CEA-N reverse primer (5"-GTC CTG AGT GGA TCC CTC GAG CTA GGT GM GG CCA CAGC-3") (SEQ IS NO:9). FLAG-tagged rCEA N was generated by fusing a FLAG epitope to the His-tag/TEV cleavage site of a recombinant CEA domain composed of residues 1-214 using the FLAG-N forward primer (5'-CCCAT ATG GGC AGC AGC CAT CAT CAT CAT CAT CAC AGC AGC GGC GAC TAC MG GAC GAC GAT GAC MG MG CTC ACT ATT GM TCC ACG CCG TTC MT GT-3') (SEQ ID NO:10) and the FLAG N reverse primer (5"-GTT CAG ATT TTC CCC CTC GAG CTA AGA TGT GTT TAG AGG GGA MT GGT GGG GGC ATC CGG-3") (SEQ ID NO:11). The inclusion of additional CEA residues at the C-terminus was found to improve the stability of the construct and increase its yield. The CEA $A_3B_3$ domain (residues 445-656) included a C-terminal His-tag and was generated using the $A_3B_3$ forward primer (5'-TATACC CATATG GCC MT MC TCA-3') (SEQ ID NO:12) and the $A_3B_3$ reverse primer (5"-CTA TAT CTC GAG TCA ATG GTG ATG GTG ATG GTG ATG GTG GCC GAC AGT GGC CCC AGC TGA GAG ACC-3") (SEQ ID NO:13). PCR Amplicons were subcloned into pET30b (Novagen; Gibbstown, N.J.) between the NdeI and XhoI restriction sites and the constructs were transformed into the E. coli strain BL21 DE3 Star (Invitrogen; Ontario, Canada).

Expression of rCEA modules was achieved by growing transformed cells in Lauria Bertani (LB) broth supplemented with kanamycin (75 μg/mL) at 37° C. to an optical density ($OD_{600\ nm}$) of 0.5, followed by the induction of protein expression with 1 mM IPTG over a period of 24 hours at 37° C. Cell pellets were collected by centrifugation (8,000 g, 15 minutes, 4° C.), then resuspended and lysed in TRITON™ X-100, 25 mM Tris (pH 8), 150 mM NaCl containing lysozyme (100 U per mL; Sigma-Aldrich; Ontario, Canada) and BENZONASE™ nuclease (1 U per mL; Novagen). Inclusion bodies containing the expressed rCEA domains were sedimented by centrifugation (25,000 g; 4° C.; 20 minutes) and the resulting pellets resuspended in 8 M urea, 25 mM Tris (pH 8), 250 mM NaCl, and 10 mM β-mercaptoethanol. The suspensions were then re-sedimented and the supernatants containing the solubilised His-tagged rCEA proteins collected and loaded directly onto a Ni-NTA agarose column (Sigma-Aldrich). The rCEA modules were purified under denaturing conditions where contaminating proteins were washed away using a buffer containing 8M urea, 25 mM Tris, pH 8, 250 mM NaCl, 10 mM β-mercaptoethanol and 5 mM imidazole. The bound recombinant CEA modules were specifically eluted with 8 M urea, 25 mM Tris, pH 8, 250 mM NaCl, 10 mM β-mercaptoethanol and 50 mM imidazole.

Fractions containing purified rCEA protein modules were concentrated by ultrafiltration against a buffer containing 50 mM Tris, pH 8.0, 150 mM NaCl and 10 mM β-mercaptoethanol. The removal of the His-tag affinity arm from the purified CEA modules was performed by incubating 15 mg of purified rCEA N domain in 50 mM Tris (pH 8), 150 mM NaCl, 1 mM DTT and 1 mM EDTA supplemented with 250 μg of recombinant Tobacco etch virus (rTEV) protease for 20 hours at room temperature. Separation of the cleaved rCEA N domain (residues 1-132) from the released affinity tag, rTEV and uncleaved His-tagged proteins was achieved by passing the cleaved protein solution through a Ni-NTA agarose column. The extent of cleavage and the purity of the final recombinant products were monitored by SDS PAGE.

For vaccination purposes, endotoxin contamination was removed from rCEA N domain preparations by passing solutions of the purified protein through DETOXI-GEL™ columns (Pierce, Thermo Scientific, Ontario, Canada). The final products were stored at 4° C. until further use.

Immunoprecipitation Assay

Co-immunoprecipitations of rCEA N and $A_3B_3$ complexes were performed by mixing magnetic protein A beads (New England Biolabs; Pickering, Ontario, Canada) coated with 1 μg of either mAb Col1 (mouse IgG1 mAb specific to the CEA N domain; Invitrogen) or an isotype control antibody. The coated beads were then mixed with a 1 mL solution containing 1 μM of each module. The bound complexes were resolved by SDS-PAGE and visualized by Coomassie staining.

Measurement of CEA Homotypic Interactions by ELISA

The binding of a FLAG-tagged rCEA N to rCEA N, rCEA $A_3B_3$ or the full length tumour glycoform of CEA was assessed using an enzyme-linked immunosorbent assay (ELISA) [Madrid et al., 2004]. Briefly, 96-well flat-bottomed FALCON™ microtiter plates (Becton-Dickinson Biosciences; Franklin Lakes, N.J.) were coated with 2 μg of purified CEA modules or full length CEA per well. After blocking with PBS containing TWEEN™ (0.05% v/v) and bovine serum albumin (1% w/v), the plates were then incubated for one hour at room temperature with increasing concentrations of the FLAG-tagged rCEA N diluted in PBS-TWEEN™ (0.05%; 100 μL). The presence of bound FLAG-tagged rCEA was detected by incubating the plates for 1 hour at room temperature with horseradish peroxidase (HRP) coupled anti-FLAG monoclonal antibody M2 (1:5,000 dilution; Sigma-Aldrich). The chromogenic HRP substrate 3,3',5,5'-tetramethylbenzidine (TMB; Sigma) was used to measure at 450 nm the amount of bound FLAG-tagged N domain.

Cell Lines and Growth Conditions

CEA-expressing human cancer cell lines BxPC-3 (ATCC No. CRL-1687, human pancreatic adenocarcinoma), HT-29 (ATCC No. HTB-38; human colorectal adenocarcinoma) and MCF-7 (ATCC No. HTB22; human breast adenocarcinoma) were used to monitor their sensitivity to complement-dependent cytotoxicity (CDC) in the presence of serum derived from vaccinated mice. The murine colonic carcinoma MC38.CEA and MC38 cells were kindly provided by Dr. Jeffrey Schlom (National Cancer Institute; Bethesda, Md.). The human cervical adenocarcinoma cell line HeLa (ATCC No. CCL-2) provided CEA$^-$ cells in the CDC studies. All cells were cultured at 37° C., 5.0% $CO_2$ in Dulbecco's modified Eagle's medium supplemented with 10% fetal bovine serum, penicillin (100 U/mL), and dihydrostreptomycin (100 μg/mL).

A bi-cistronic lentiviral vector co-expressing the firefly Luciferase and green fluorescent protein was used to generate stably transfected, luciferase producing MC38.CEA (MC38.CEA$^{LUC}$) cells as previously described [Tiscornia et al., 2006]. Briefly, HEK-283T cells were used to produce LUC/GFP encoding (luc$^+$ gfp$^+$) lentiviruses by co-transfecting them with plasmid pHR2 coding for packaging and envelope pCMV and plasmid VSV-G. Supernatants from producer cells were used to transduce MC38.CEA cells in the presence of polybrene (10 μg/mL; Sigma) and protamine sulfate (10 μg/mL; Sigma). Following transfection, the cells were sorted twice for high GFP expression. Surviving colonies were amplified and screened for both bioluminescence using a XENOGEN™ IVIS spectrum (Caliper Life Sciences; Hopkinton, Mass.) as well as CEA expression by immunoblotting.

Animals

Breeder pairs of mice expressing human CEA as a transgene (CEA.Tg) were a gift from Dr. Wolfgang Zimmerman (Tumour Immunology Laboratory, LIFE-Center, Klinikum Grosshadern, Ludwig-Maximilians-University; Germany). CEA-positive litters were generated by backcrossing CEA-positive animals with parental C57BL/6 mice [Nöckel et al., 2006]. The genotype of CEA.Tg mice was confirmed by PCR [Nöckel et al., 2006]. Transgenic animals as well as C57BL/6 mice were bred and kept under standard pathogen-free conditions at the Ontario Cancer Institute animal facility. All experiments were performed under the approval of the local animal welfare committee and in accordance with the rules and regulations of the Canadian Council for Animal Care.

Immunizations and Tumour Challenge

For immunizations following tumour implantation, 12-16 weeks-old CEA.Tg mice received $2.0 \times 10^5$ MC38.CEA cells subcutaneously (s.c.) in their hind leg. All animals were then randomly subdivided into three groups. One group of CEA.Tg mice was left untreated (non-immunized group), whereas the second group received an intraperitoneal dose (i.p.) of 100 μg poly I:C alone (referred to thereafter as adjuvant). The last group of animals was given i.p. 100 μg of endotoxin-free rCEA N domain mixed with 100 μg poly I:C (referred to thereafter as immunized). Animals were primed on day 13 and boosted on days 20 and 28 post tumour implantation.

For immunizations preceding tumour implantation, CEA.Tg mice were primed on day 1 by i.p. injection with 100 μg of endotoxin-free rCEA N domain mixed with 100 μg poly I:C followed by two i.p. boosts composed of 50 μg endotoxin-free rCEA N domain and 100 μg poly I:C on days 3 and 10 post-injection. The sera from CEA.Tg mice were screened for anti-CEA IgG antibodies and only responders (80-90% of immunized mice) were included in subsequent tumour challenge experiments. MC38.CEA$^{LUC}$ tumour cells were implanted i.p. on day 28 for peritoneal invasion studies or were injected i.v. (tail vein) for lung colonization studies.

Monitoring of Tumour Growth and Tumour Burden

The length and width of s.c. implanted tumours were measured with calipers. Tumour volumes were calculated using the following formula: Volume in $mm^3 = ((x^2 \times y)/2)$. To enumerate pulmonary tumour nodules, formalin-fixed lung specimens were embedded in paraffin, sectioned at three different depths, and 4 μm sections were stained with hematoxylin and eosin (H&E). Images of stained slides were recorded and analyzed for tumour foci using an Aperio slides scanner and ImageScope software (Aperio Technologies Inc; Vista, Calif.). The growth and expansion of MC38.CEA$^{LUC}$ tumour cells implanted in the peritoneal cavity was monitored by injecting luciferin (100 μL; 100 mM) i.p. and recording the luminescence signal emitted from the peritoneal region of CEA.Tg mice using a XENOGEN™ IVIS spectrum (Caliper Life Sciences; Hopkinton, Mass.) on days 1, 3 and 8. At day 35 post-tumour implantation, the animals were euthanized, dissected and their tumour burden assessed by measuring the number and size of established tumour nodules.

Preparation and Cultivation of Leukocytes

Spleens were aseptically removed from vaccinated CEA.Tg mice following euthanasia. Splenic leukocytes were then collected by gently forcing the organs through a 100 μm cell strainer (FALCON™). The resulting cell suspensions were subsequently washed three times with cold RPMI supplemented with penicillin (100 U/mL), streptomycin (100 μg/mL) and 1% FBS. Cell viability following harvest was typically ≥95%, as determined using a Trypan blue dye exclusion assay. These leukocytes were suspended at a density of $1 \times 10^6$ cells per mL in RPMI-1640 supplemented with penicillin (100 U/mL), streptomycin (100 μg/mL), 2 mM l-glutamine, 1 mM HEPES, 0.05 mM β-mercaptoethanol and 10% FBS and maintained at 37° C. in a humidified 5.0% $CO_2$ atmosphere.

Analysis of CEA-Specific Cellular Immunity

Splenocytes from immunized and control mice were stimulated ex vivo with either concanavalin A (ConA; 5 μg per mL; Sigma-Aldrich), the full length tumour glycoform of human CEA (1 μg per mL; Sigma-Aldrich), rCEA WT N domain (1 μg per mL) or left as unstimulated controls. Quantification of CEA-specific cytokine secreting cells was performed using IFN-γ, IL-10 and IL-4 ELISPOT™ assay kits (R&D Systems; Minneapolis, Minn., USA). The spots were enumerated using an automated ELISPOT™ plate counter (Cellular Technologies Inc; Shaker Heights, Ohio). Frequencies of CEA-specific cytokine secreting cells were calculated by subtracting background values (calculated from wells containing unstimulated cells) from measured values derived from tested conditions as previously described [Abdul-Wahid and Faubert, 2007].

Detection of CEA-Specific Antibodies by ELISA

Antibody responses raised in CEA.Tg mice and directed at the N domain of CEA were analyzed by ELISA as previously described [Abdul-Wahid and Faubert, 2007]. Briefly, 96-well microtiter ELISA plates (FALCON™) were coated with 1 μg per well of rCEA N domain. Sera derived from immunized or control mice were serially diluted in 1% BSA-PBS-EDTA (25 mM) and incubated at room temperature with gentle shaking for 1 hour. After washing the plates with PBS-TWEEN™ (0.05%), wells were exposed to solutions of either HRP-coupled anti-mouse IgG, IgG1 or IgG2a secondary antibodies (diluted in 0.5% BSA-PBS-EDTA; 1:5,000; Bethyl Laboratories; Montgomery, Tex.) for 1 hour at room temperature. The plates were then washed and developed using TMB as a substrate. The chromogenic reactions were stopped using half volume of 0.5 M $H_2SO_4$ and absorbance readings measured at 450 nm.

Generation of Lymphokine-Activated Killer (LAK) Cells

Lymphokine-activated killer (LAK) cells were generated as previously described [Nishimura et al., 2008], by stimulating splenic leukocytes derived from CEA.Tg mice with recombinant murine IFN-γ (1000 U per mL; Pepprotech Inc; Rocky Hill, N.J.) and IL-2 (250 U per mL; Pepprotech Inc) for 48 hours followed by IL-2 treatment every 3 days until day 10 when the cells were harvested for ADCC assays.

Analysis of Antibody-Dependent Cytotoxicity

Analyses of antibody-mediated killing of tumour cells by either complement-dependent cytotoxicity (CDC) or Ab-dependent cellular cytotoxicity (ADCC) were performed by incubating MC38.CEA$^{LUC}$ cells with sera obtained from either immunized, adjuvant-treated or non-immunized mice (1:250 dilution) in the presence of either LAK cells (3:1 effector to target ratio) or exogenous complement (1:250 dilution; Cedarlane laboratories; Burlington, Ontario, Canada). Following a three-hour incubation period at 37° C., cell viability was assessed by adding luciferin to MC38.CEA$^{LUC}$ target cells and recording the relative luminescence signal using a XENOGEN™ IVIS imaging system (Caliper Life Sciences Inc.; Hopkinton, Mass.).

Inhibition of CEA-Mediated Cell Adhesion

MC38.CEA$^{LUC}$ cells were mixed with sera (1:250 dilution) from either immunized or control CEA.Tg mice for 15 minutes at 37° C. The cell suspensions were then added to multi-well plates seeded with confluent MC38.CEA monolayers and incubated for 2 hours at 37° C. Unbound cells were washed away and the presence of bound MC38.CEA$^{LUC}$ cells was determined by measuring their luminescence using a XENOGEN™ IVIS spectrum imaging system (Caliper Life Sciences; Hopkinton, Mass.) as previously described. The specificity of the homophilic intercellular interaction for the CEA N domain was determined by mixing the sera from immunized CEA.Tg mice with 1 μM rCEA N domain prior to treating MC38.CEA$^{LUC}$ cells with serum and performing the cell adhesion assay.

Adoptive Transfer of Lymphocytes

To assign the role of lymphocytes in protecting mice from developing tumour nodules in the peritoneal cavity, total spleen lymphocytes or purified B cells derived from immunized CEA.Tg mice were injected into the tail vein of immunologically naive recipient CEA.Tg mice. B lymphocytes were purified by negative selection (EASYSEP™ mouse B cell enrichment kit; StemCell Technologies, British Colombia. Canada) from single cell suspensions of total spleen leukocytes collected from immunized CEA.Tg mice (n=6). Specifically, B cells were separated from cells of other hematopoietic origin defined by the surface antigens CD4, CD8, CD11b, CD43, CD49b, Ly-6G (GR-1) and TER119. Recipient naïve mice received $2\times10^6$ B cells per mouse (corresponding to a mouse equivalent) or $4.1\times10^5$ spleen lymphocytes. Three days later, $2.0\times10^5$ MC38.CEA$^{LUC}$ cells were implanted in the peritoneal cavity of treated mice. The proliferation of MC38.CEA$^{LUC}$ cells and the development of tumour nodules were monitored as described previously for the first 21 days post-tumour implantation.

Passive Immunization with Hyper-Immune Sera

Sera from immunized CEA.Tg mice (n=6) were collected one day following the last booster injection (day 11 post immunization), pooled and diluted with PBS (1:10), filter sterilized and stored at −20° C. until use. The presence of CEA N domain-specific serum antibodies was verified by ELISA as previously described. Serum samples (200 μL) were injected i.p. into immunologically naïve CEA.Tg mice (n=5) on days −5 to 3 and days 10 to 17. On day 0, $2.0\times10^5$ MC38.CEA$^{LUC}$ cells were implanted in the peritoneal cavity and the development of tumours was monitored as described above.

Statistics and Data Analysis

Collected data sets were analyzed for significance by ANOVA and individual groups were compared using Student-t-test. All statistical analyses and graphs were done using PRISM (version 5.01; Graph Pad Software for Science, San Diego, Calif.). P values≤0.05 were considered significant.

Results

Expression of Recombinant CEA Domains Involved in Homotypic Association

Figure 18:
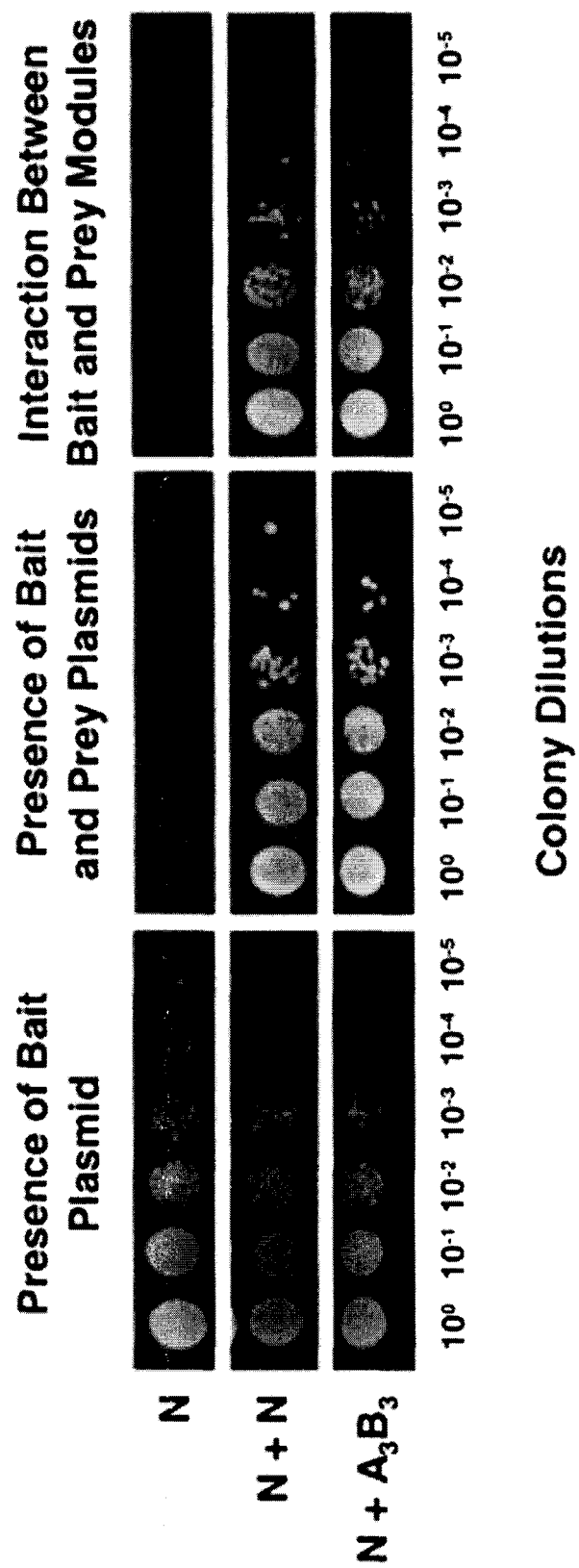
FIG. 18 shows yeast-2-hybrid experiments confirming the binding of rCEA N domain to itself and to the $A_3B_3$ domain. A plasmid vector expressing the IgV-like N domain of CEA as a C-terminal fusion to the GAL4 DNA-binding domain (Bait vector), was co-transformed in the yeast strain AH109 with a vector expressing either the CEA IgV-like N- or the IgC-like $A_3B_3$ domains fused to the C terminus of the GAL4 activation domain (Prey vectors) [McCluskey et al., 2008]. The resulting yeast colonies were grown overnight and spotted (5 µl) as tenfold serial dilutions onto either SD medium lacking Trp to select for the presence of the Bait plasmid in yeast cells; SD medium lacking both Trp and Leu to select for the presence of both Bait and Prey plasmids in yeast cells or by spotting onto SD lacking Trp, Leu, and His to select for Bait and Prey plasmids expressing the N-Gal and $A_3B_3$-Gal fusion proteins that interact with each other leading to colony growth. The yeast growth results (last panel to the right) suggests that the CEA N domain Bait fusion protein interacts with its CEA N domain Prey fusion counterpart or with the CEA $A_3B_3$ domain Prey fusion construct.

Generating an immune response able to block the cell adhesion properties of CEA required production of individual Ig-like domains of CEA involved in such interactions. The N and $A_3B_3$ domains of CEA have been shown in the past to interact with each other resulting in the homotypic association of CEA molecules [Zhou et al., 1993]. In the present example, these domains were separately expressed in E. coli, purified and their folded state confirmed in three distinct assays measuring their homotypic association. Specifically, individual N and $A_3B_3$ domains were expressed as fusion constructs with Gal promoter complementary domains in a yeast 2-hybrid assay with their interaction resulting in yeast survival (FIG. 18) [McCluskey et al., 2008]. Secondly, protein A magnetic beads coated with the mAb Col1 (specific for the CEA N domain) were used to specifically pull-down the rCEA N domain either alone or with rCEA $A_3B_3$ thereby confirming that both domains did form complexes in solution (FIG. 9A). Finally, the rCEA N domain was shown by ELISA [Madrid et al., 2004] to form comparably tight complexes with either the rCEA $A_3B_3$ fragment or the wild type full length CEA derived from tumour cells (FIG. 9B). A weaker interacting pair involving the N domain binding to itself was also observed by ELISA (FIG. 9B).

In theory, both the IgV-like N- and the IgC-like $A_3B_3$ fragments would represent proper immunogens in a vaccination strategy aimed at countering CEA-mediated cell aggregation events. However, the N domain of CEA offers two additional advantages over all other IgC-like domains within CEA. It incorporates the PELPK motif (residues 108-112) [Samara et al., 2007] shown to mediate the lodging of CEA-positive tumour cells into the liver. An immune response engendered to this domain may block the presentation of this motif and thus its role in tumour implantation at distal organs. Secondly, the IgV-like N domain lacks cysteine residues and its protein fold does not require the presence of a disulfide bridge as in the case of all other IgC-like domains of CEA, a useful feature in designing a stable, properly folded immunogen.

A key challenge in producing a useful immune response to the carcinoembryonic antigen is the fact that CEA is a self antigen and as such, host immune responses to this antigen are typically dampened through central and peripheral tolerance mechanisms [Morse et al., 2008; Bos et al., 2008]. CEA (as is the case with other related CEACAM molecules) is heavily N-glycosylated when presented on cancer cells. It was postulated that by expressing a single domain of CEA (residues 1-132) in bacteria [rCEA N], this resulting N domain would lack N-glycans and present a non-natural C-terminus leading to the display of a distinct set of determinants/epitopes in relation to the full length antigen. These unique structural features of the rCEA N domain would skew the host immune system into perceiving this immunogen as an altered form of a self-antigen.

Therapeutic Immunization with the CEA N Domain Retards the Growth of Subcutaneously Implanted CEA-Expressing Murine Tumours in a CEA Transgenic Mouse Model.

A vaccination protocol using the recombinant CEA N domain as an immunogen was evaluated to assess if an immune response to CEA in CEA.Tg mice could interfere with the growth of implanted murine colonic MC38.CEA tumour cells. Specifically, $2\times10^5$ MC38.CEA cells were implanted into the hind leg of CEA.Tg mice. The animals were subsequently subdivided into three groups. The first group was not vaccinated with a formulation of endotoxin-free rCEA N mixed with the adjuvant poly I:C (non-immunized) and served as a control group for tumour growth. The second group of animals received only the adjuvant administered directly into their intraperitoneal cavity (i.p) (poly I:C; group referred to thereafter as the adjuvant group). The final group received endotoxin-free rCEA N mixed with poly I:C given in a similar i.p. route (immunized group).

As presented in FIG. 10A, the subcutaneous implantation of $2\times10^5$ MC38.CEA cells resulted in the formation of palpable tumor nodules in the majority of mice within twelve days post implantation. On day 13 post tumor implantation, the mice were vaccinated by injecting (i.p.) 100 μg endotoxin-free rCEA N domain mixed with 100 μg poly I:C and boosted on days 20 and 28. Poly I:C was chosen as the adjuvant in view of its capacity to stimulate both B cell activation [Scher et al., 1973] as well as $T_H1$ responses through TLR-3/7 signalling [Barchet 2008], a combination of immune responses that have been shown to positively influence the development of protective anti-tumor immune responses in mice and in clinical trials [Barchet 2008]. The inherent immunogenicity of purified human CEA has not been reported in the past. It was thus decided to use an intraperitoneal route of administration, since the immunogenicity of an antigen is traditionally evaluated using this immunization route [Garvey et al., 1983]. As highlighted in FIGS. 10B and 10C, vaccination with the rCEA N domain delayed the rapid growth of established hind leg tumours in relation to tumour cells implanted in non-immunized and adjuvant only-treated CEA.Tg mice.

Colonization and Formation of Pulmonary Tumour Nodules in CEA Transgenic Mice are Blocked by Pre-Vaccination with the rCEA N Domain.

A rapidly expending localized tumour mass, as in the case of the s.c. implantation of murine MC38.CEA in the hind leg, represents a tumour burden that is typically treated by local surgery and radiation therapy [Berinstein, 2002; von Mehren, 2005]. An appropriate use of CEA-based anticancer vaccines would preferably be in the context of adjuvant therapies targeting metastasizing cells rather than eradicating primary tumours as the deregulated overexpression of CEA appears to be directly linked to the process of tumour metastasis [Samara et al., 2007; Zimmer and Thomas, 2001; Bast et al., 2001; Molina et al., 2005; Duffy, 2006].

Tumour metastases in distal organs were not observed following the subcutaneous implantation of MC38.CEA cells in the hind leg. To address this limitation of the hind leg implantation model, mice were first vaccinated i.p. with endotoxin-free rCEA N domain and poly I:C and subsequently challenged with $2\times10^5$ MC38.CEA tumour cells administered intravenously as outlined in FIG. 11A. Sixty days post tumour injection, the animals were euthanized and dissected to determine the distribution of tumour nodules in organs.

Figure 11:
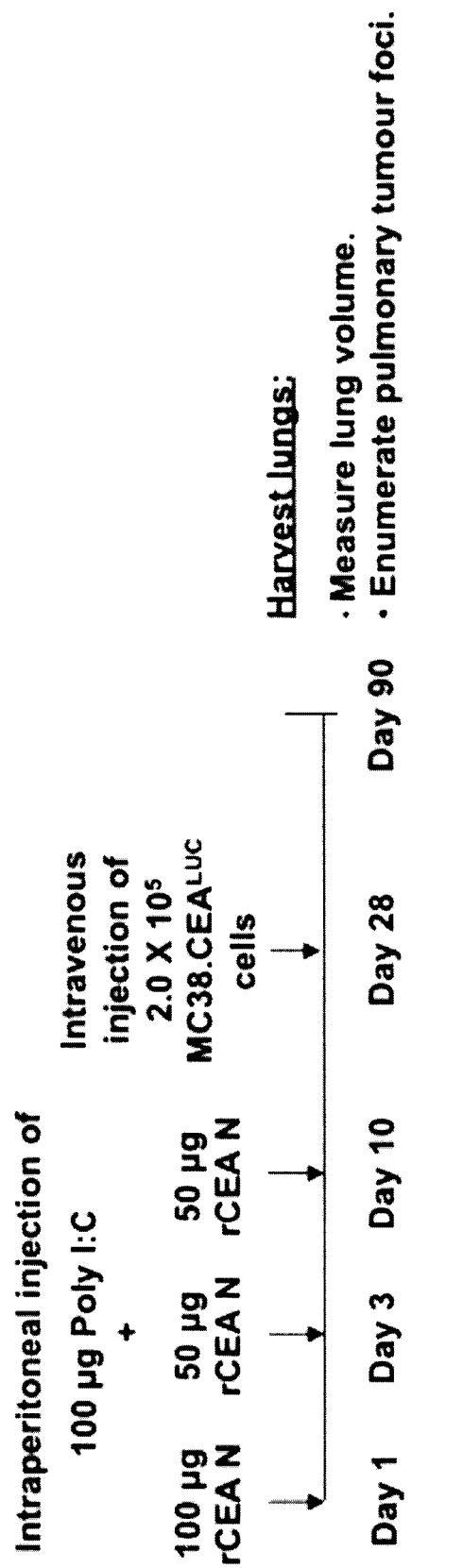
FIG. 11 shows vaccination of CEA.Tg mice (i.p.) with the rCEA N domain as an immunogen prevents the development of pulmonary tumor nodules. A. Experimental design and immunization schedule. B. CEA-expressing murine colonic carcinoma MC38. CEA cells were injected i.v. (tail vein) into CEA.Tg mice at day 28 post-vaccination. Photographs highlight tumour masses (black arrows) present in lung tissues isolated from immunized and control CEA.Tg mice at day 60 post tumor injection. C. Haematoxylin and eosin (H&E) stained sections of whole mouse lungs displaying large tumour nodes in the case of non-vaccinated or adjuvant alone-treated animals (dark stained areas). The histological features of lung tissues from immunized mice were similar to that of a normal mouse lung. D. Enumeration of tumor foci in H&E stained lung specimens (n=6, whole lungs from each treatment group). E. Total volume of lung tissues (including tumour masses; n=12) at day 60 post tumour implantation. Statistical significance was determined using Student-t-test.
Figure 11:
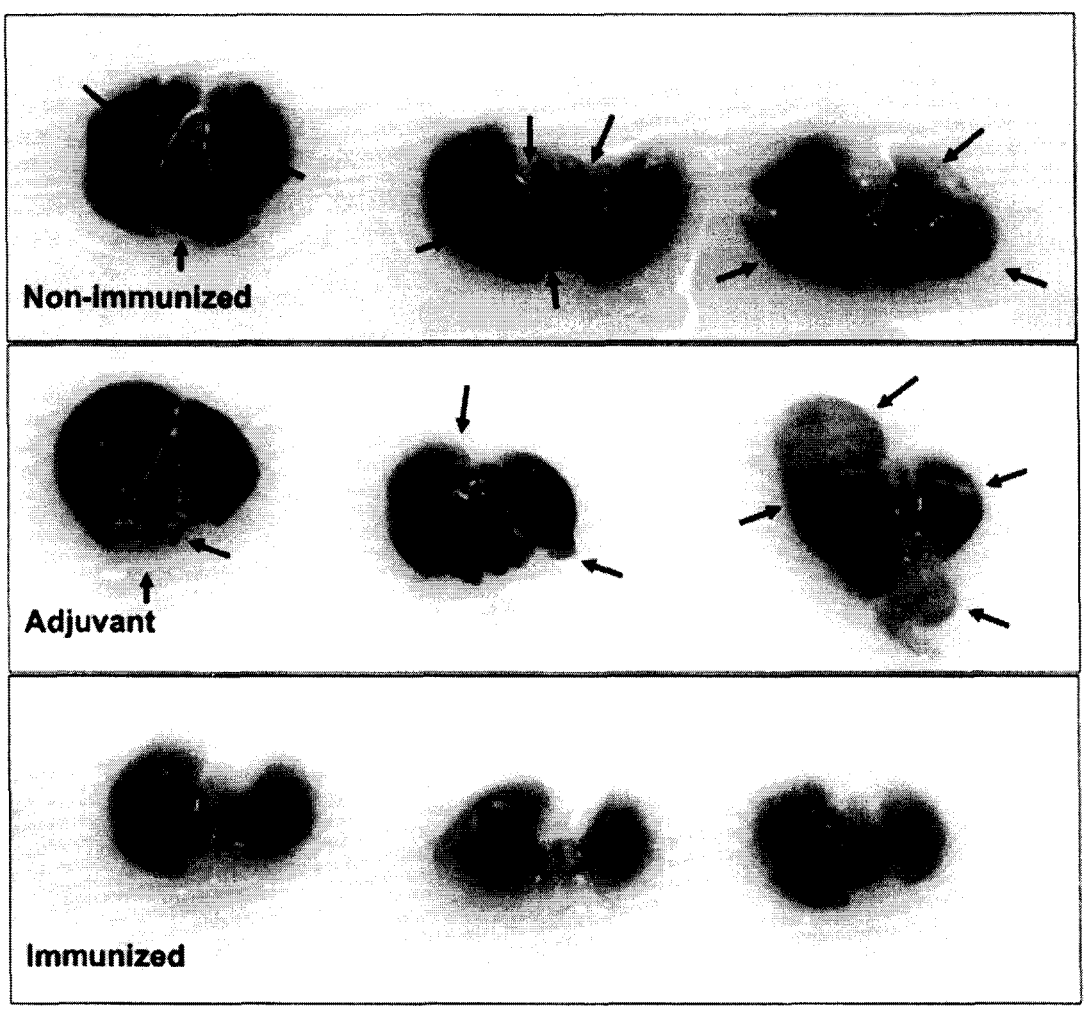
Figure 11:
Figure 11:
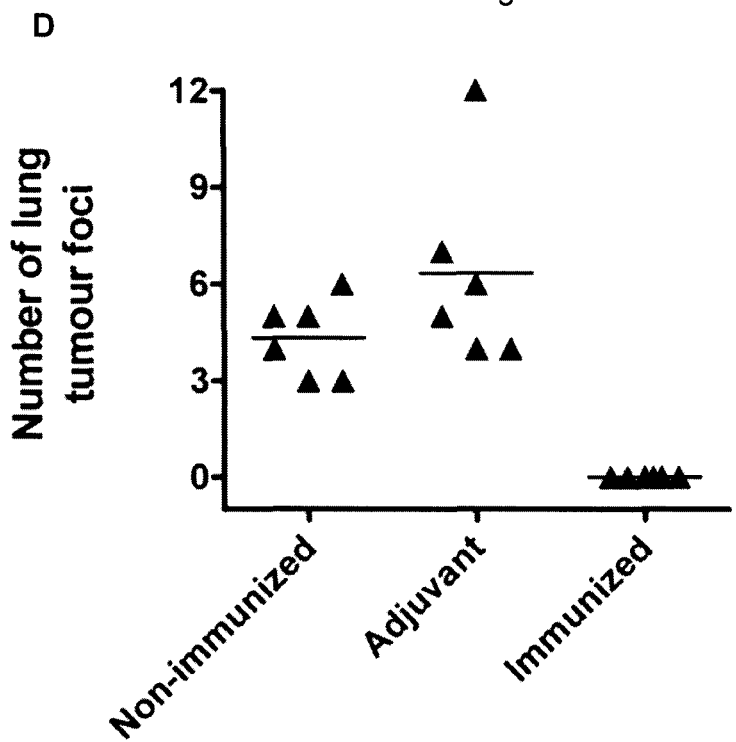
Figure 11:
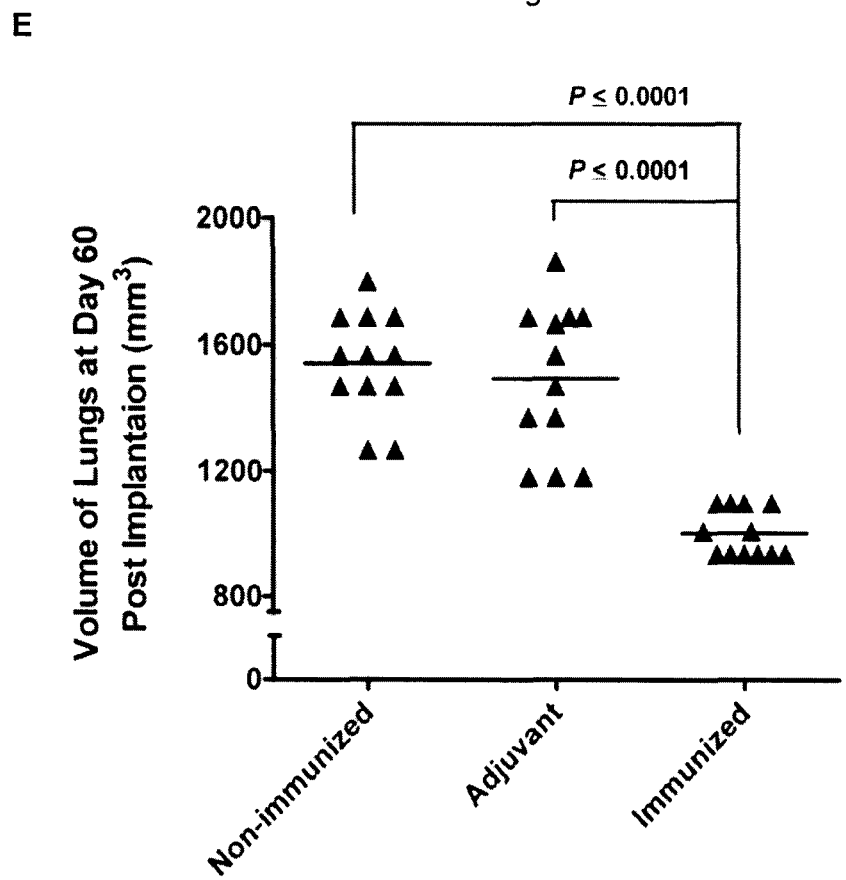

A visual inspection of dissected organs indicated that the majority of animals having received MC.38.CEA cells intravenously developed large tumour masses in the lungs within 60 days (FIGS. 11B and 11C). Tumour nodules were also observed in the liver in a limited subset of animals (less than 5 percent of untreated mice). Histological examination of lung tissues (H&E stained lung sections; n=18; 6 randomly chosen lungs from each group) derived from control animals (non-immunized and adjuvant treated groups) confirmed that lungs were significantly enlarged as a consequence of the number and size of tumour foci in contrast to lungs taken from either normal age-matched or immunized animals (FIG. 11, panels B to E). These results suggest that the administration of the rCEA N domain as an immunogen was effective in preventing the development of pulmonary tumour nodules.

Pre-Vaccination with the rCEA N Domain Prevents Tumour Colonization and the Formation of Tumour Nodules in the Peritoneal Cavity.

CEA-expressing adenocarcinomas, particularly in the case of patients with gastric cancer, have been reported to metastasize to the abdominal cavity [Asao et al., 1989]. Pre-vaccinating CEA.Tg mice with the rCEA N domain could prevent the establishment of tumour foci within the peritoneal cavity. Briefly, animals were pre-vaccinated i.p. as described previously (FIG. 12A), 18 days prior to the intraperitoneal implantation of $2\times10^5$ MC38.CEA$^{LUC}$ cells. The MC38.CEA$^{LUC}$ cell line was created to allow for the visualization and expansion of these cells in vivo post-implantation (as a measure of luciferase production). As indicated in FIG. 12B, pre-vaccination of CEA.Tg mice resulted in the loss of luminescence signal in their peritoneal cavities of these animals. By day 8 post-implantation, no luminescence could be detected (FIG. 12B) in immunized mice, while significant luminescence signals were recorded in the abdominal cavity of non-immunized and adjuvant only-treated animals (FIG. 12B). At day 35 post-tumour implantation, the animals were euthanized, their organs dissected and examined for the presence of tumour nodules. No tumour masses were detected outside of the peritoneal cavity (site of implantation). Non-immunized and adjuvant only-treated animals had developed large tumour nodules while vaccinated animals displaying an immune response to CEA remained tumour-free (FIGS. 12C and 12D).

The Intraperitoneal Administration of rCEA N Domain with Poly I:C Produces a Strong CEA-Specific Humoral Response The vaccination protocol used in this example led to positive outcomes in the context of three distinct in vivo tumour implantation models. To define the immunological mechanisms responsible for protection, age-matched CEA.Tg mice were subdivided into three groups (FIG. 5A); either non-immunized, treated (i.p.) with poly I:C alone or with the rCEA N domain mixed with poly I:C. Four days following the last immunization step, the animals were sacrificed and their blood and spleens collected to analyze correlates of immune responses.

Figure 19:
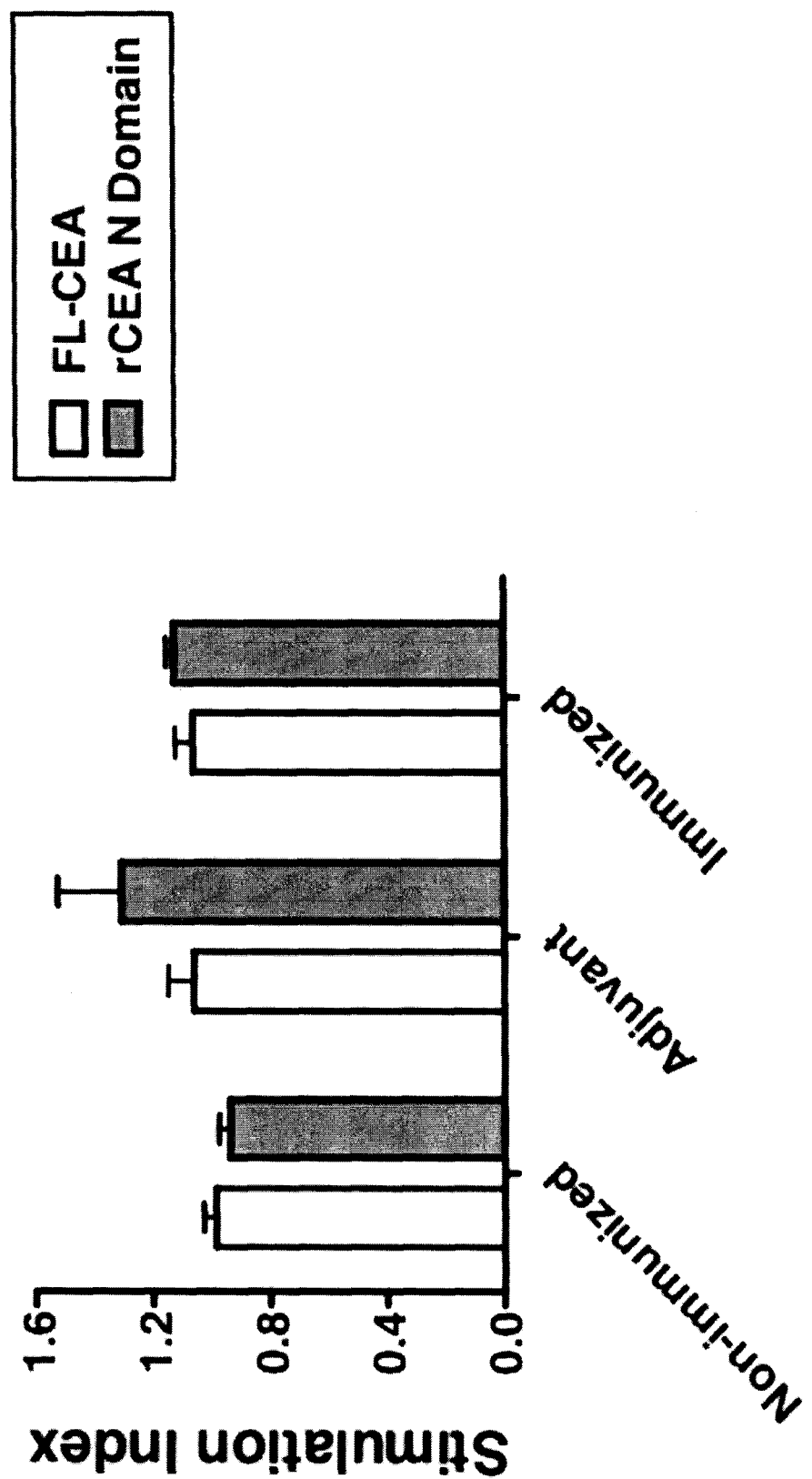
FIG. 19 shows lack of lymphoproliferation in response to stimulation with the rCEA N domain or full length CEA. Cells were isolated from the spleens of immunized or control mice (n=4 mice per group) and cultured for 72 h in the presence of either full length glycosylated CEA (FL-CEA) or the rCEA N domain. Splenocytes from immunized and control mice were stimulated in vitro with either concanavalin A (ConA; 5 µg per mL), the full length tumour glycoform of human CEA (1 µg per mL), rCEA WT N domain (1 µg per mL) or left as unstimulated controls. Cells were then grown for 48 hours (37° C., 5% $CO_2$) followed by pulsing with $^3$H-thymidine for 24 hours. The amount of incorporated thymidine was measured in harvested cells using a scintillation counter. Results of lymphoproliferation are represented as a stimulation index (cpm of Ag stimulated cells/cpm of unstimulated cells). A stimulation index greater than 1.5 is considered an indicator of significant Ag-specific lymphoproliferation. Stimulation of lymphocytes (from any of the test groups) with ConA yielded a stimulation index greater than 10 (data not shown). No statistically significant proliferations were observed from splenocytes from immunized or control mice when stimulated with CEA constructs. Data sets were analyzed by ANOVA.

The presence of CEA-specific cellular responses was first analysed following the isolation of spleen leukocytes derived from CEA.Tg mice from all three groups. The leukocytes were stimulated in vitro with either rCEA N domain or the full length tumour glycoform of CEA (FL-CEA). Irrespective of the antigen used for stimulation, little or no proliferation of leukocytes was observed (FIG. 19). This observation suggested that the immunization protocol yielded a modest level of T cell stimulation. The development of CEA-specific, $T_H$-cell responses was subsequently assessed by measuring the number of antigen-specific cytokine (IL-4, IL-10 and IFN-γ) secreting cells by ELISPOT™ assays [Berinstein, 2002; Hodge et al., 2009; Woo et al., 2008]. Non-immunized CEA.Tg mice as well as mice given the adjuvant alone did not stimulate the production of CEA-specific cellular immune responses, since leukocytes derived from these animals did not secrete cytokines in response to antigenic stimulation with either rCEA N domain or the full length tumour glycoform of CEA (FIG. 13B). In contrast, stimulation of lymphocytes (derived from immunized CEA.Tg animals) with either the rCEA N domain or the full length CEA tumour glycoform yielded a balanced cytokine production profile, as suggested by the equal numbers of recorded antigen-specific IL-4, IL-10 and IFN-γ secreting cells (as spot forming units from ELISPOT™ assays; FIG. 13B).

The presence of circulating anti-CEA antibodies was subsequently analyzed by ELISA. High titres of circulating anti-CEA IgG antibodies were observed only in sera derived from immunized CEA.Tg mice (FIG. 14A). Isotype analysis revealed high titres of CEA-specific IgG1 and IgG2a (FIG. 14A). These high IgG1 and IgG2a titres were consistently observed in ≥90% of individual vaccinated animals derived from independent immunization trials (FIG. 14B) and correlated with the observed balanced CEA-specific cytokine response (FIG. 13B). Moreover, the vaccination protocol yielded anti-CEA antibodies that specifically reacted with MC38.CEA cell lysates, implying that the presence of N-linked sugars had no consequence on the recognition of epitopes by rCEA N-domain-specific serum antibodies. Together, these observations suggest that the immunization strategy yielded a strong humoral immune response supported by a modest $T_H$ cell response.

N Domain-Specific Antibodies can Mediate Ab-Dependent Killing of Tumour Cells as Well as Block CEA-Dependent Intercellular Adhesion Events The ability of N domain-specific serum antibodies in mediating antibody-dependent cell killing was first assessed in ADCC or complement-dependent cell killing assays (FIG. 15). Specifically, MC38.CEA$^{LUC}$ cells were incubated with sera collected from either vaccinated, adjuvant-treated and untreated CEA.Tg mice (1:250 dilution) in the presence of either LAK cells (3:1 effector to target ratio) or exogenous complement (1:250 dilution). Following a three-hour incubation period at 37° C., cell viability was assessed by quantifying the bioluminescence signal emitted by surviving MC38.CEA$^{LUC}$ cells. Under these conditions, significant killing of MC38.CEA$^{LUC}$ cells only occurred when incubated in the presence of sera derived from CEA-immunized mice (FIGS. 15A,B).

The capacity of CEA-specific serum antibodies in interfering with CEA-mediated homophilic interactions was assessed using two methods. First, the ability of the vaccine-elicited immune sera in interfering with homophilic cellular interactions was investigated. MC38.CEA$^{LUC}$ cells were pre-mixed with serum from immunized or control mice (1:250 dilution) and the resulting suspensions were incubated with a monolayer of non-luminescent MC38.CEA cells. Residual cell adherence was calculated from the measurement of relative luminescence signal emitted by MC38.CEA$^{LUC}$ cells still bound to the cell monolayer in the presence of interfering antibodies. Pre-treating the MC38.CEA$^{LUC}$ cell suspension with sera from immunized mice significantly reduced CEA-mediated cell adhesion, but not the sera derived from non-vaccinated or adjuvant only-treated mice (FIG. 15C). The loss of CEA-mediated cell adhesion due to serum antibodies from vaccinated animals was completely reversed by adding 1 μM soluble rCEA N-domain to the serum dilution prior to performing the cell adhesion assay (FIG. 15C).

The ability of the CEA-specific antibodies in inhibiting CEA homotypic interactions at the protein level was investigated following the results observed with CEA-expressing cell lines. Specifically, an ELISA-based protein binding assay was used to compare the inhibition of interaction between soluble FLAG-tagged rCEA N domain and immobilized rCEA $A_3B_3$ due to the addition of sera from immunized or control mice (FIG. 15D). Using the ELISA signal recorded for the rCEA N domain interacting with the rCEA $A_3B_3$ domain as a positive control signal for maximal binding, it was found that the addition of sera from control mice had no effect on blocking the homotypic binding between the N and $A_3B_3$ domain (FIG. 15D). In contrast, the addition of sera from immunized mice reduced homotypic binding by ~60% (FIG. 15D). In summary, these findings demonstrate that the production of antibodies recognizing the rCEA N domain possess both cytotoxic and homophilic adhesion blocking properties.

Passive Immunization Experiments Support the Importance of the Vaccine-Engendered Anti-N-Domain Antibodies as the Key Effector Mechanism Against Tumour Colonization.

Adoptive transfer studies were carried out to define the effector mechanism responsible for conferring the protection observed in vaccinated CEA.Tg. Specifically, sera and B lymphocytes were collected from immunized CEA.Tg mice and adoptively transferred to naïve CEA.Tg recipient mice. Following the adoptive transfer step, animals were challenged with an i.p. infusion of 2×10$^5$ MC38.CEA$^{LUC}$ cells.

Recorded luminescence images of MC38.CEA$^{LUC}$ cells within the peritoneal cavity of naïve CEA.Tg mice indicated an expansion of tumour cells on days 1, 4 and 8 post tumor implantation (FIG. 16A). In contrast, spleen-derived leukocytes or purified B cells transferred by i.v. injection 3 days earlier into naïve CEA.Tg mice as well as animals passively immunized with immune serum displayed a time-dependent regression in bioluminescence signals within the peritoneal cavity (FIG. 16A). The loss of signal observed in all three animal groups subjected to an adoptive transfer step paralleled the reduction in signal observed for CEA.Tg mice pre-vaccinated with the rCEA N domain/poly I:C formulation within the 8-day time follow-up period (FIG. 17A). Mice were sacrificed at day 21 post-MC38.CEA$^{LUC}$ implantation and their peritoneal cavity examined for the early occurrence of tumour nodules. Small tumour masses were readily observed in all untreated naïve mice while only one animal displayed tumour nodules (in either the serum-treated or the B cell treated groups) within all actively and passively immunized naïve CEA.Tg groups (FIG. 17B). These results support the view that the i.v. expansion of B cells committed to the production of CEA N domain-specific antibodies is responsible for the observed protection against tumour implantation in the peritoneal cavity of immunized mice.

Figure 17:
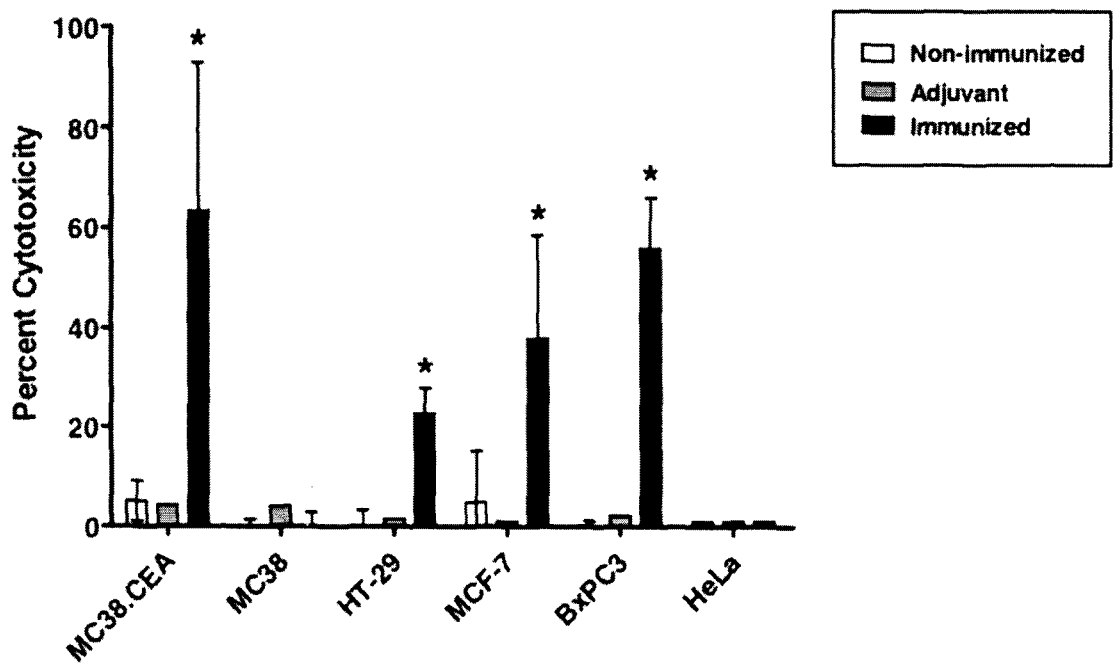
FIG. 17 shows sensitivity of CEA-expressing human adenocarcinoma cell lines to complement-dependent lysis. CEA$^+$ (MC38.CEA, HT-29, MCF-7 and BxPC3) and CEA$^-$ (MC38, HeLa) cells were suspended at a density of $1 \times 10^6$ cells per mL in a medium supplemented with rabbit complement (1:250 final dilution) and treated with sera derived from immunized or control mice (1:250 final dilution). The percentage of cell lysis was calculated from the surviving cell fraction measured by trypan blue dye exclusion. Each bar represents the average % cytotoxicity (±SEM) calculated from experiments performed in quadruplicates. Asterisk denotes statistical significance (P≤0.05; Student-t-test) when compared to cells treated with complement and sera from non-immunized CEA.Tg mice.

CEA-Expressing Human Adenocarcinoma Cell Lines are Sensitive to Complement-Dependent Cytotoxicity To validate the observed broad cytocidal property of serum antibodies specifically raised against the rCEA N domain, the capacity of sera derived from each of the 3 CEA.Tg mice groups was tested to kill a panel of CEA-expressing human tumour cells in a complement-dependent cell lysis assay. CEA$^+$ (MC38.CEA, HT-29, MCF-7 and BxPC3) and CEA$^-$ (MC38, HeLa) human cancer cell lines were treated with complement and sera derived from either immunized or control mice and the number of non-surviving cells quantified by Trypan blue dye exclusion. As depicted in FIG. 17, complement-dependent killing was only observed for CEA$^+$ MC38.CEA, BxPC-3, HT-29, and MCF-7 cells in the presence of serum derived from vaccinated animals, but not for CEA$^-$ HeLa or MC38 cells. The intensities of the complement-dependent killing qualitatively correlated with the degree of CEA expression on cell lines (FIG. 17; FIG. 20).

Discussion

The aberrant over-expression of the carcinoembryonic antigen (CEA) is associated with cancer progression and tumour metastasis [Berinstein, 2002; Samara et al., 2007; Benchimol et al., 1989; Taheri et al., 2000]. Consequently, this antigen serves as a useful clinical biomarker for monitoring recurrence and the management of metastatic cancers [Molina et al., 1998; Curigliano et al., 2006; Berinstein, 2002; Bast et al., 2001; Molina et al., 2005; Duffy, 2006]. One known function of CEA is its role in both homotypic and heterotypic interactions [Taheri, 2000; Singer et al., 2010; Zhou et al., 1993] which strongly correlates with the establishment and growth of tumour metastases in tissues such as the liver, lung and the peritoneal cavity [Berinstein, 2002; Samara et al., 2007; Zimmer and Thomas, 2001; Zhou et al., 1993]. The IgV-like N domain of CEA represents the common denominator in all CEA-dependent interactions. Mechanistically, CEA over-expression and its self-association correlate with the early inactivation of caspase-9, the activation of the PI3-K/Akt survival pathway as well as the inactivation of caspase-8 [Camacho-Leal P and Stanners, 2008] presumably by directly binding TRAIL-R2 (DR5) via its pentapeptide PELPK motif (residues 108-112 found in its N domain) [Samara et al., 2007]. In the case of colorectal cancer, the PELPK sequence was found to be required for the lodging of metastatic CEA-expressing cells onto the liver parenchyma [Samara et al., 2007; Zimmer and Thomas, 2001; Hostetter et al., 1990]. From a structural perspective, the IgV-like N domain of CEA strongly interacts with its IgC-like $A_3B_3$ domain, allowing adjacent CEA molecules to homotypically adhere to each other. Such homotypic adhesion events on CEA-positive cells yield networks of homophilic intercellular interactions that further contribute to lodging additional cells within the context of expanding nascent metastatic foci [Samara et al., 2007; Taheri et al., 2000; Zimmer and Thomas, 2001; Zhou et al., 1993; Hostetter et al., 1990]. It was hypothesized that an immune response focused on the CEA N domain would yield a polyclonal antibody response able to block homophilic cell adhesion events between CEA-positive cells that lead to tumour implantation and growth as well as producing antibodies capable of destroying CEA-bearing tumour cells through antibody-dependent cell-mediated cytotoxicity (ADCC) and complement-dependent cytotoxicity (CDC). Accordingly, a recombinant form of the N domain of CEA (residues 1-132) was expressed in E. coli and purified to serve as an immunogen in a formulation aimed at vaccinating CEA.Tg mice. The recombinant IgV-like N domain of CEA (rCEA N) is a bacterially produced protein that represents an altered form of a self-antigen by virtue of the fact that it lacks naturally-occurring N-linked glycans and displays an unnatural C-terminus. This feature addresses the key issue that the human immune system is normally tolerant of self-antigens such as CEA [Morse et al., 2008; Bos et al., 2008]. The generated rCEA N domain also includes the PELPK motif (residues 108-112) associated with the lodging of CEA-expressing metastasizing tumour cells into the liver. Finally, the use of a single domain of CEA as the immunogen will narrow the immune response to a focused and distinct set of determinants in relation to the full length antigen.

Figure 9:
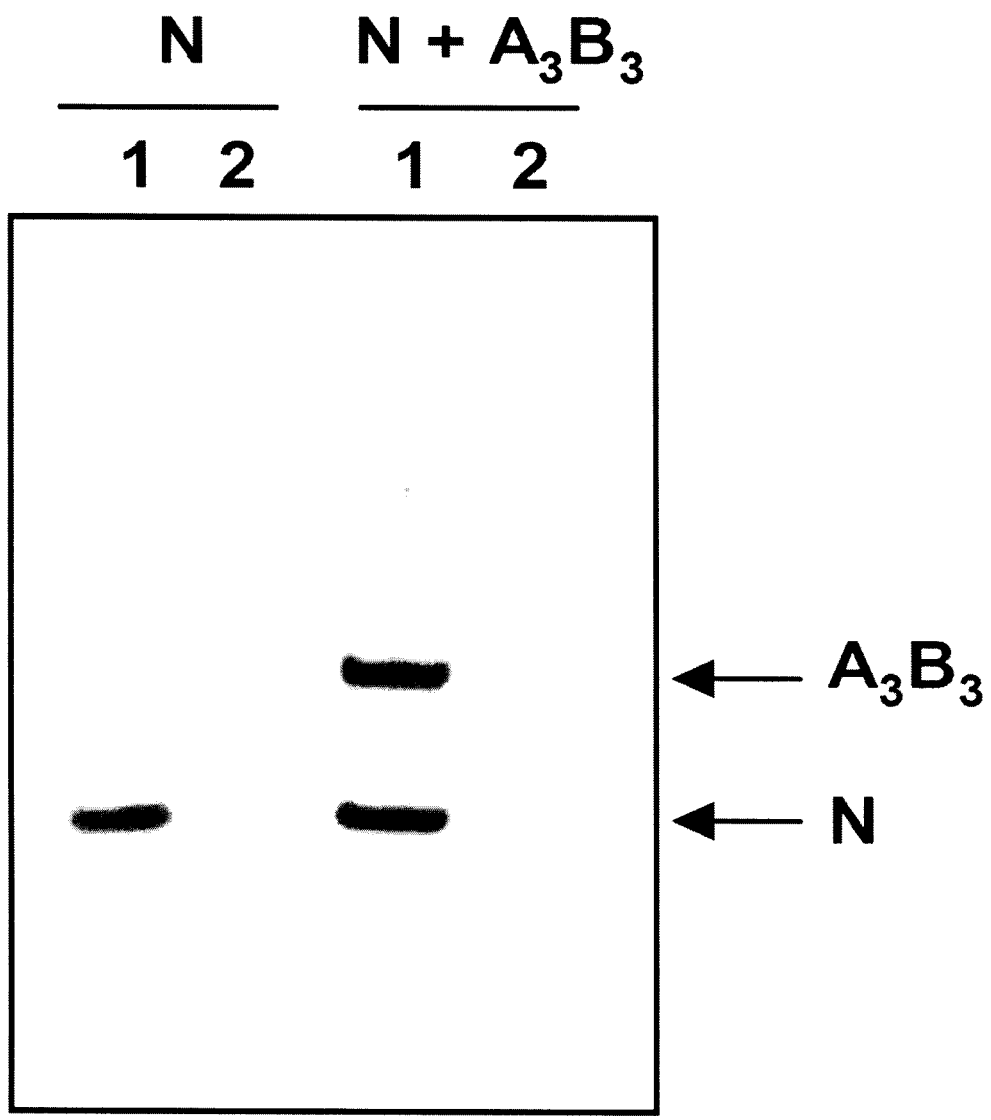
FIG. 9 shows the analysis of the folding and homotypic binding activity of the generated rCEA N modules. A. Co-immunoprecipitation of recombinant CEA N and $A_3B_3$ domains. Magnetic protein A beads pre-coated with either mAb Col1 (recognizing the N domain of CEA; lane 1) or an isotype control mAb (lane 2) were added to a suspension containing 1 μM of each recombinant protein. Recovered protein complexes were resolved by SDS-PAGE and protein bands visualized by Coomassie staining. B. Relative binding affinities of the rCEA N domain to either the full-length tumor glycoform of CEA (▲), rCEA N domain (●) or the rCEA $A_3B_3$ domain (■) as defined by ELISA. Each data point represents the average absorbance value (±SEM) from experiments performed in triplicates.
Figure 9:
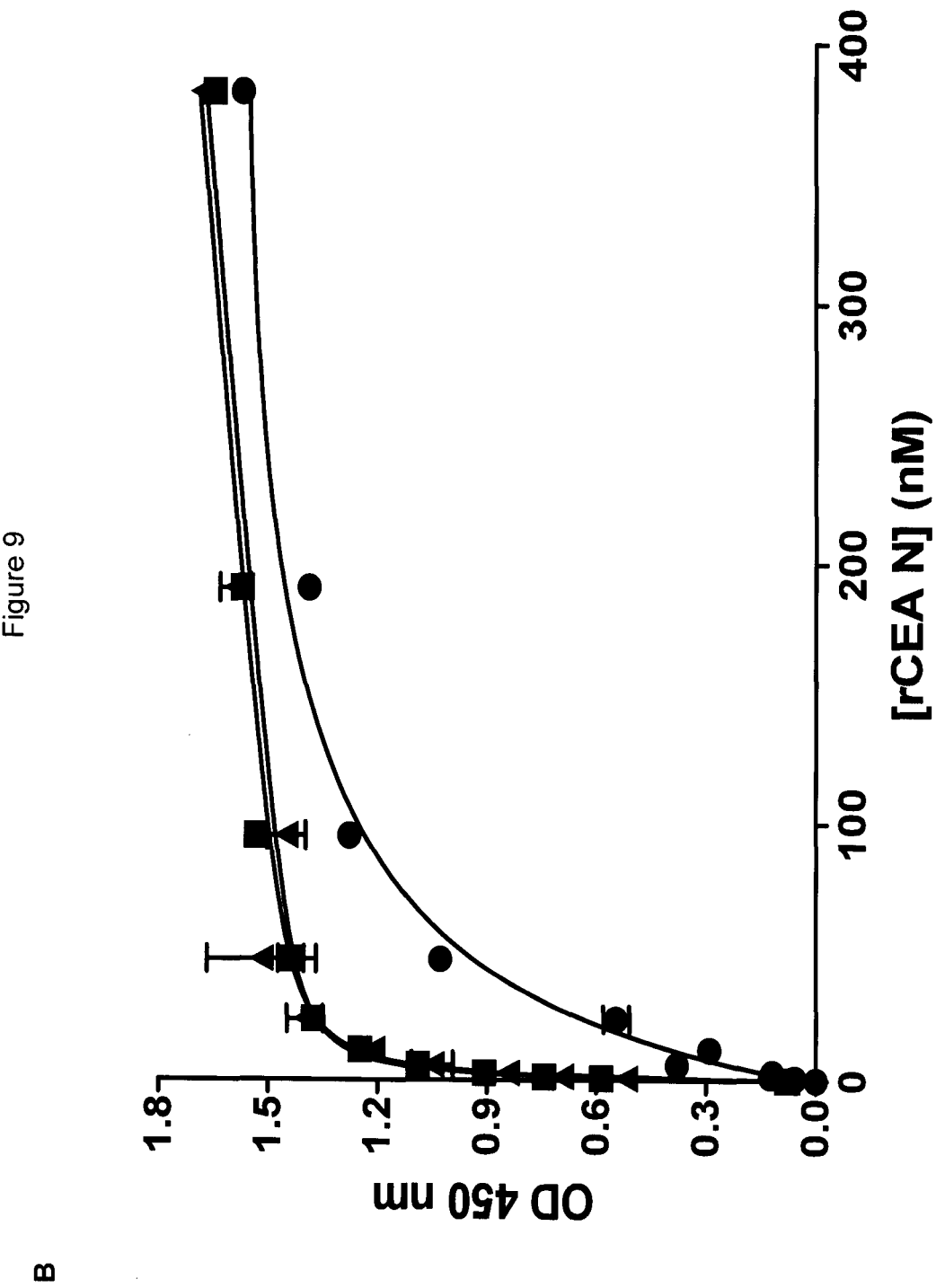

Experimentally, the expressed rCEA N domain retained its known binding properties to itself, the rCEA $A_3B_3$ module as well as the full length, tumour-derived glycosylated CEA (FIG. 9). The folded endotoxin-free rCEA N domain was then mixed with the adjuvant poly I:C and the mixture was administered i.p. into CEA.Tg mice with a view of eliciting a protective immune response against CEA$^+$ murine colonic MC38.CEA tumour cells. Poly I:C was chosen as the adjuvant in view of its capacity to stimulate both B cell activation [Scher et al., 1973] as well as type 1 responses through TLR-3/7 signalling [Barchet et al., 2008], a combination of immune responses that have been shown to positively influence the development of protective anti-tumor immune responses in both mice and patients [Barchet et al., 2008]. Additionally, the rCEA N domain/poly I:C formulation was administered i.p to gauge the immunogenicity of this altered-self antigen [Garvey et al., 1983].

Figure 10:
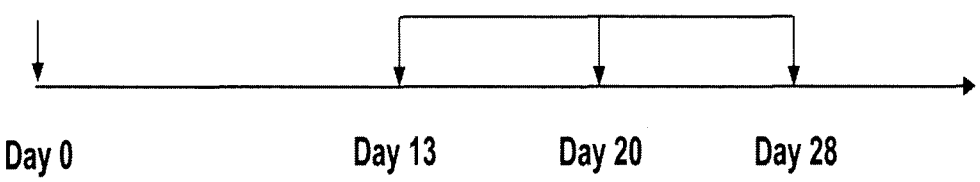
FIG. 10 shows vaccination of CEA.Tg mice i.p. with the rCEA N domain as an immunogen results in the stabilization of tumour growth in immunized mice. A. Experimental design and immunization schedule. B. Tumour growth kinetics of an established CEA-expressing, murine colonic carcinoma MC38.CEA implanted s.c. in the hind leg of non-immunized CEA.Tg mice (▲; n=12), mice who received the adjuvant poly I:C only (■; n=12) or mice immunized with rCEA N domain and adjuvant (●; n=12). C. Collection of individual tumour growth curves observed for every CEA.Tg mice within each experimental treatment group. Each line represents a single mouse.
Figure 10:
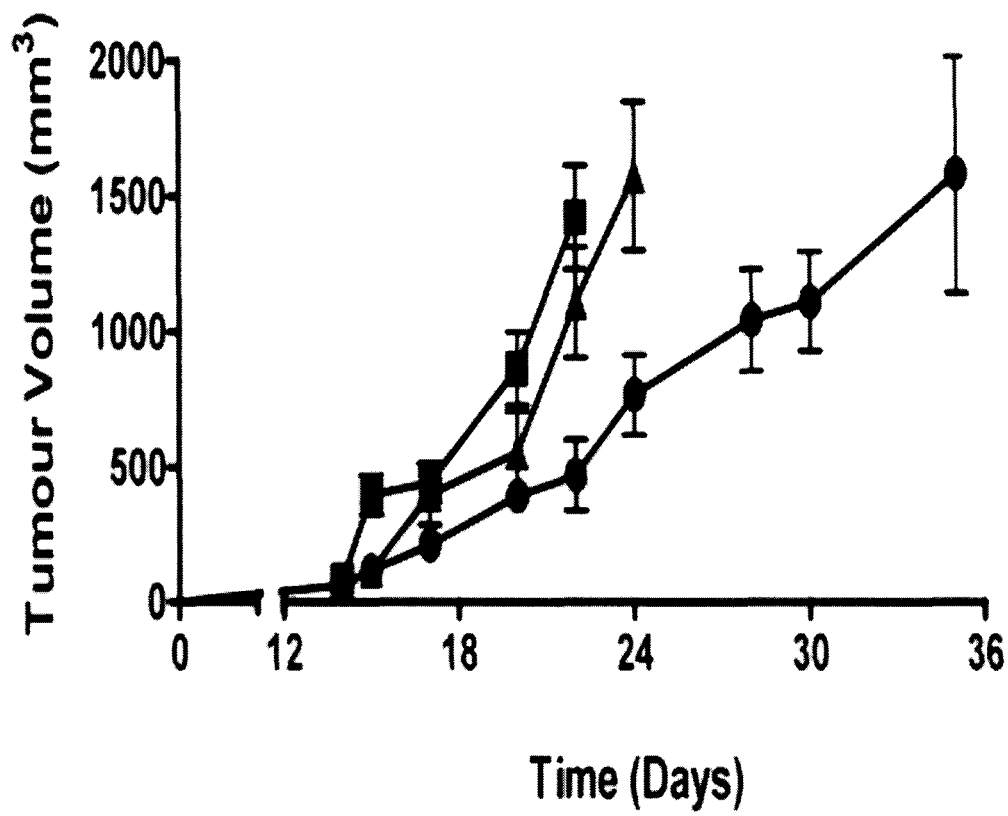

MC38.CEA cells were implanted into CEA.Tg mice using 3 distinct approaches. As a first implantation model, MC38.CEA cells were introduced subcutaneously into the hind leg of transgenic mice; an approach that led to the very rapid establishment and growth of localized large tumour masses. Vaccination of animals following tumour establishment provided a significant delay in tumour growth (FIG. 10). However, it was projected that a mounted immune response to the rCEA N domain would serve a more appropriate role in blocking the establishment of new tumour foci rather than in arresting the uncontrolled localized growth of a solid tumour mass. CEA.Tg mice were thus given an intravenous bolus of M38.CEA cells which led to the development of large tumour foci in the lungs within 60 days post-injection. Immunizing CEA.Tg mice with the N domain prior to the i.v. injection of tumour cells protected all vaccinated animals from developing pulmonary tumour nodules (FIG. 11A-E). In contrast, all non-immunized and adjuvant only-treated mice displayed numerous pulmonary tumour nodules within the same time period (FIG. 11A-E), suggesting that vaccination prevented the lodging and establishment of tumour foci in the lungs.

Figure 12:
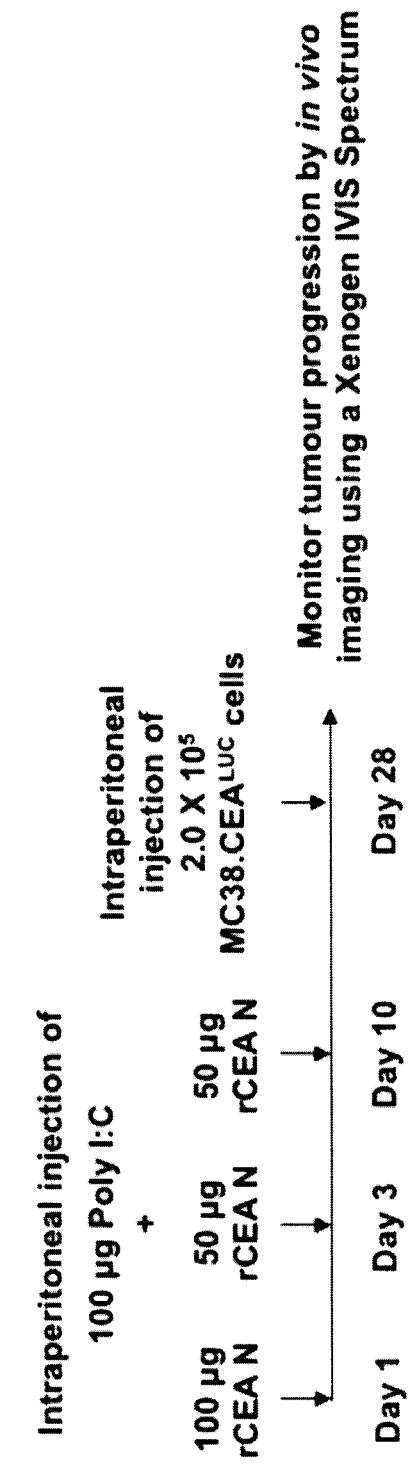
FIG. 12 shows vaccination of CEA.Tg mice i.p. with the rCEA N domain as an immunogen prevents the development of peritoneal tumour nodules. A. Experimental design and immunization schedule, Stably-transformed MC38.CEA$^{LUC}$ cells expressing luciferase were injected i.p. into non-immunized, adjuvant-treated or immunized CEA.Tg mice B. In situ monitoring of MC38.CEA$^{LUC}$ cell growth and expansion at day 1, 3 and 8 post-implantation. Recorded luminescence signals in animals (XENOGEN™ IVIS; i.p. injection of luciferin) after tumour implantation demonstrate a drop in signal with time for implanted MC38.CEA$^{LUC}$ cells in vaccinated animals. C. Photographs highlighting the absence and presence of tumour nodules in the viscera of immunized and control mice at day 35 post-tumour injection. The tumour nodules are indicated by green arrows, D. Number of tumour nodules present in the peritoneal cavity of immunized and control mice (n=5). Statistical significance was determined using Student-t-test.
Figure 12:
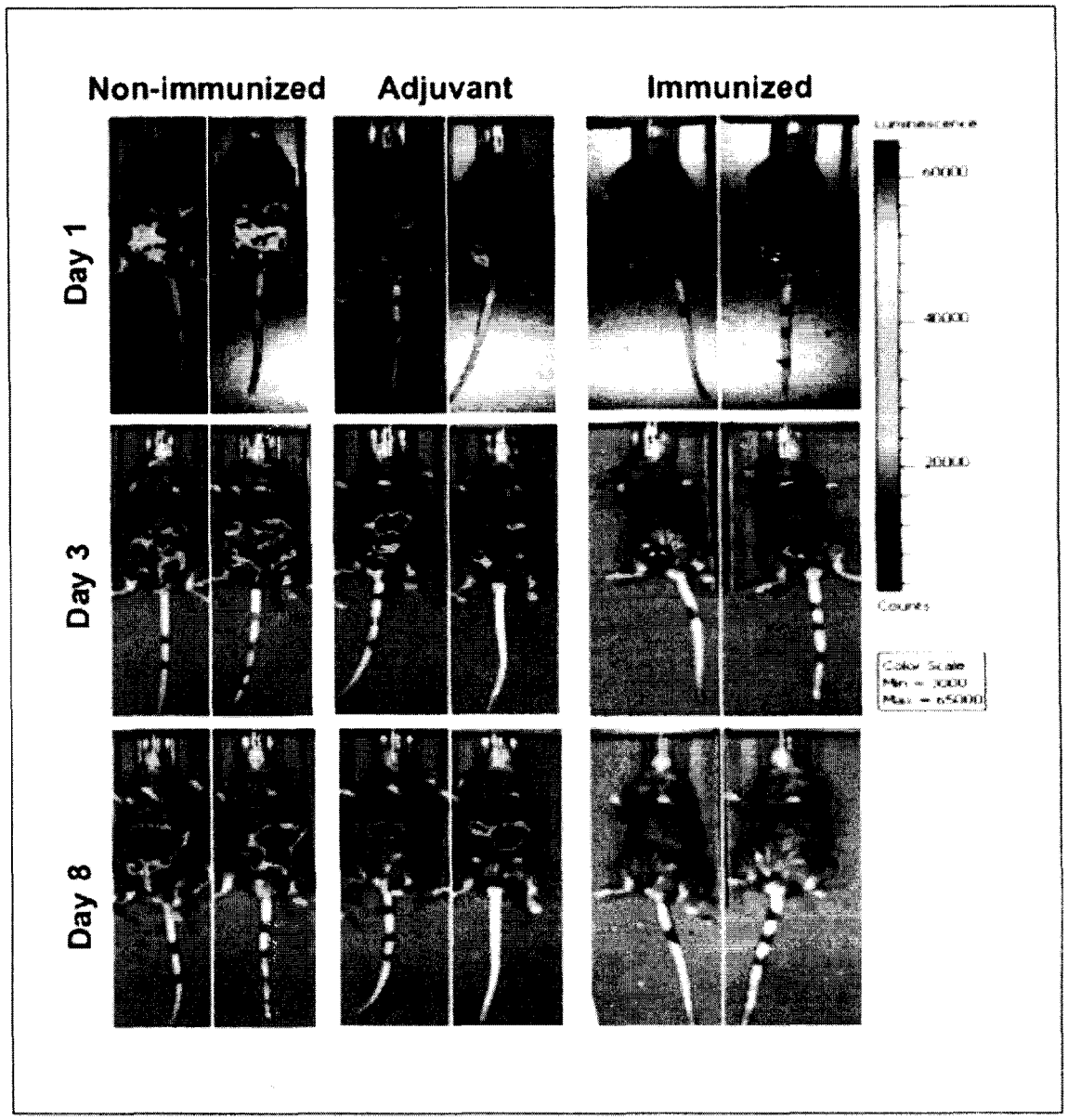
Figure 12:
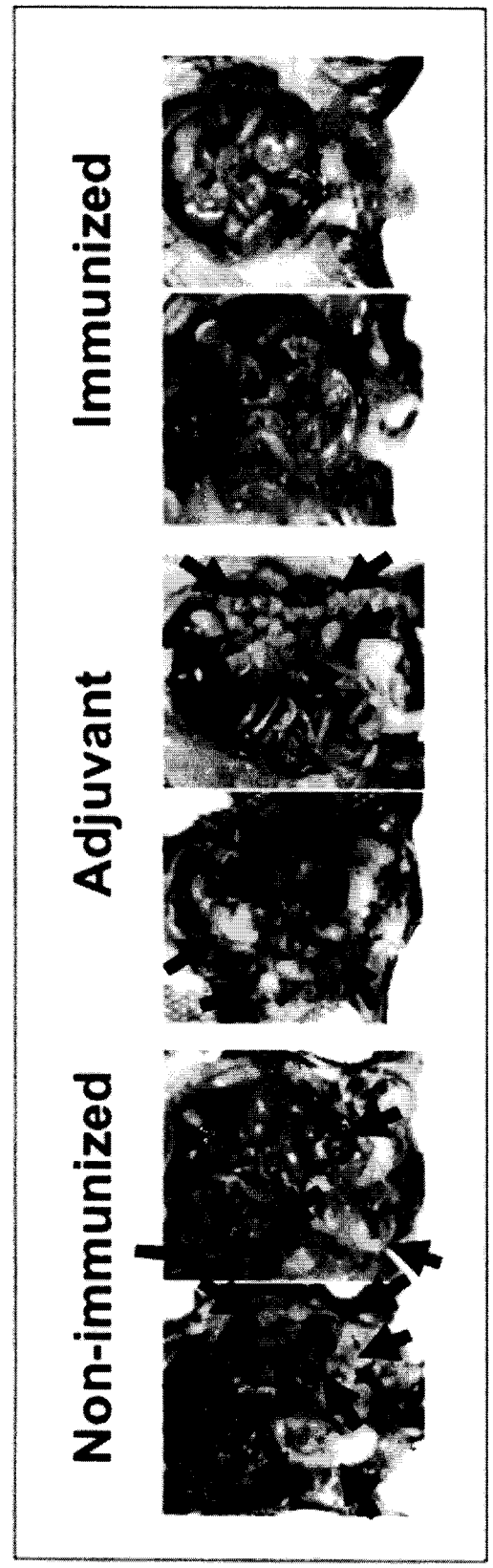
Figure 12:
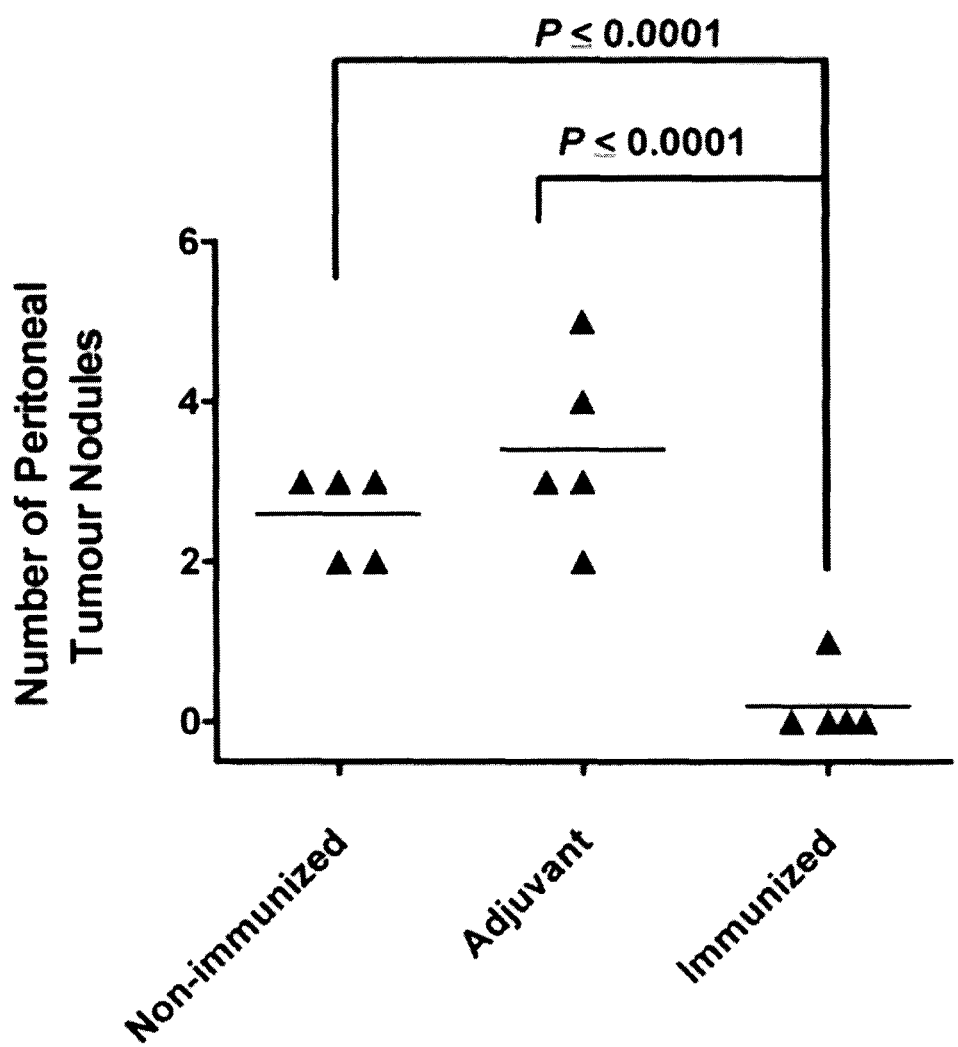

CEA+ tumour metastases are also observed in the peritoneal cavity [Asao et al., 1989]. MC38.CEA cells were thus directly implanted into the peritoneal cavity of CEA.Tg mice to observe the development of tumour nodules. In this implantation model, the luminescence signal generated by MC38.CEA$^{LUC}$ cells was used to monitor the rapid dissemination and expansion of these cells within the first 8 days post-implantation. The outcome of immunizing CEA.Tg mice with the N domain prior to the i.p. injection of tumour cells was identical to the i.v. implantation route, with the luminescent MC38.CEA$^{LUC}$ cells vanishing from the peritoneal cavity (FIG. 12B) resulting in the absence of tumour nodules being observed in the intraperitoneal space (and elsewhere) when animals were sacrificed at day 35 (FIGS. 12C and 12D). A different outcome occurred in all non-immunized and adjuvant-treated mice where MC38.CEA cells expended quickly post implantation resulting in the occurrence of numerous tumour foci by day 35 (FIG. 12 B-D). As predicted, pre-vaccinating CEA.Tg mice prevented the growth of MC38.CEA cells injected i.p. and the establishment of tumour masses in the peritoneal cavity.

The use of a recombinant rCEA N protein domain as an immunogen within the context of a simple vaccination procedure limits concerns for safety [Woo et al., 2008]. This vaccine is also appealing over previously published vaccination strategies since the engendered response will target a narrower range of potentially relevant epitopes, bypassing antigenic competition from irrelevant epitopes [Crosti et al., 2006; Shen et al., 2004; Kobayashi et al., 2002; Matsuda et al., 2004; Dai et al., 2008] present in full length CEA. Only one report describes the use of CEA-based subunit vaccine. Specifically, the rCEA A$_3$B$_3$ domain was mixed with CpG oligonucleotides and subcutaneously injected into C57BL/6 mice [Woo et al., 2008]. The authors reported that this strategy produced a weak CEA-specific immune response that failed to protect C57BL/6 mice against a lethal tumour implant (when compared to a TAT-fused construct) [Woo et al., 2008]. In contrast, the present study uses the CEA N domain mixed with poly I:C to produce an effective CEA-specific immune response in CEA.Tg mice against tumour implantation to the lungs and peritoneal cavity (FIG. 13-15).

Figure 16:
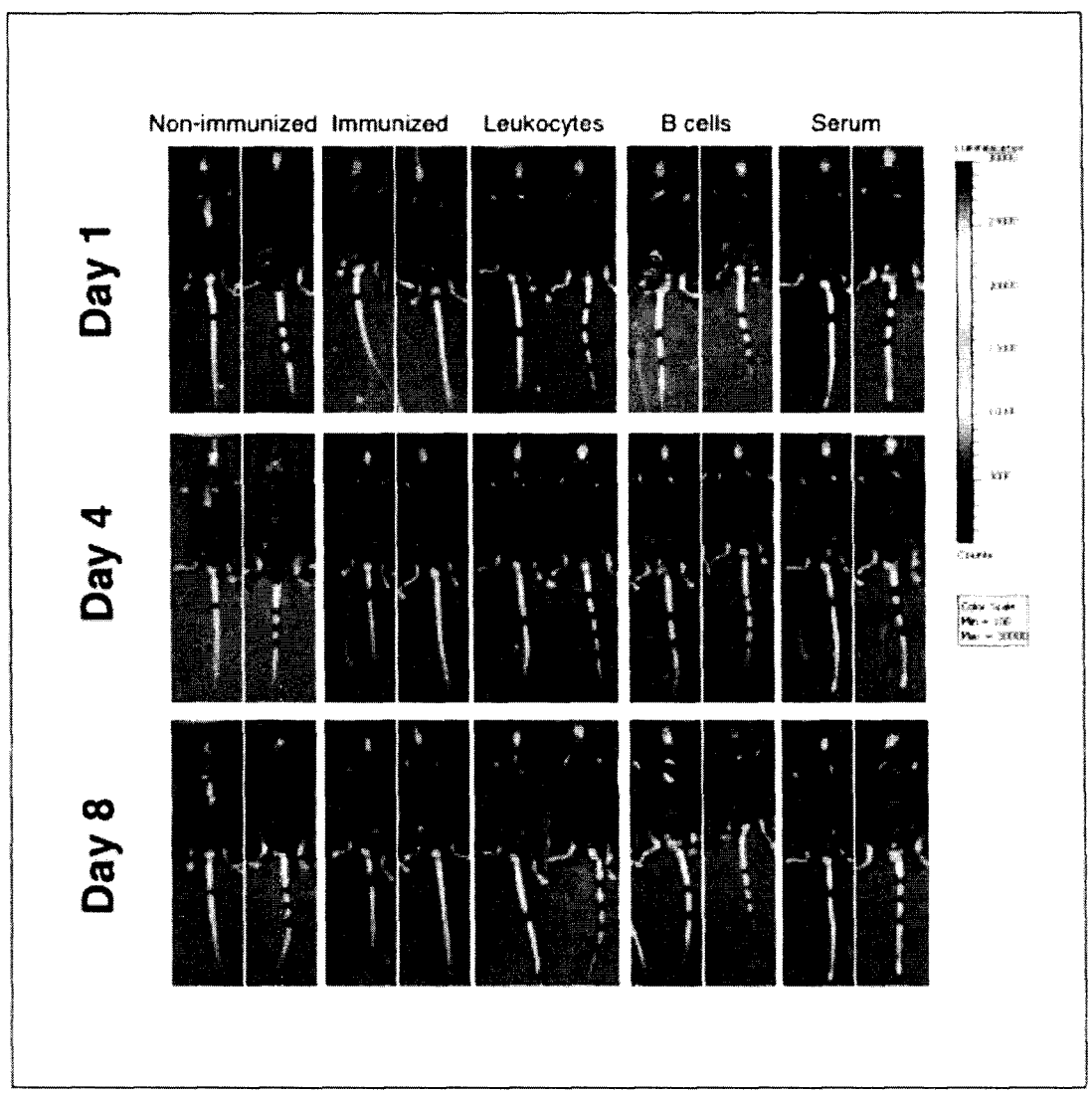
FIG. 16 shows adoptive transfer of CEA N-domain specific antibodies or B lymphocytes derived from vaccinated CEA.Tg mice into naive CEA.Tg recipients prevents the development of peritoneal tumour nodules. A. In situ monitoring of MC38.CEA$^{LUC}$ cell growth and expansion at day 1, 3 and 8 post-implantation. Recorded luminescence signals in animals (XENOGEN™ IVIS) after tumour implantation demonstrate a drop in signal with time for implanted MC38.CEA$^{LUC}$ cells into naive CEA.Tg animals pre-treated either with purified B cells (i.v.) or serum (i.p.) derived from vaccinated CEA.Tg mice. B. Cumulative tumour volumes at day 21 post-MC38.CEA$^{Luc}$ implantation into the peritoneal cavity of naïve CEA.Tg mice.
Figure 16:
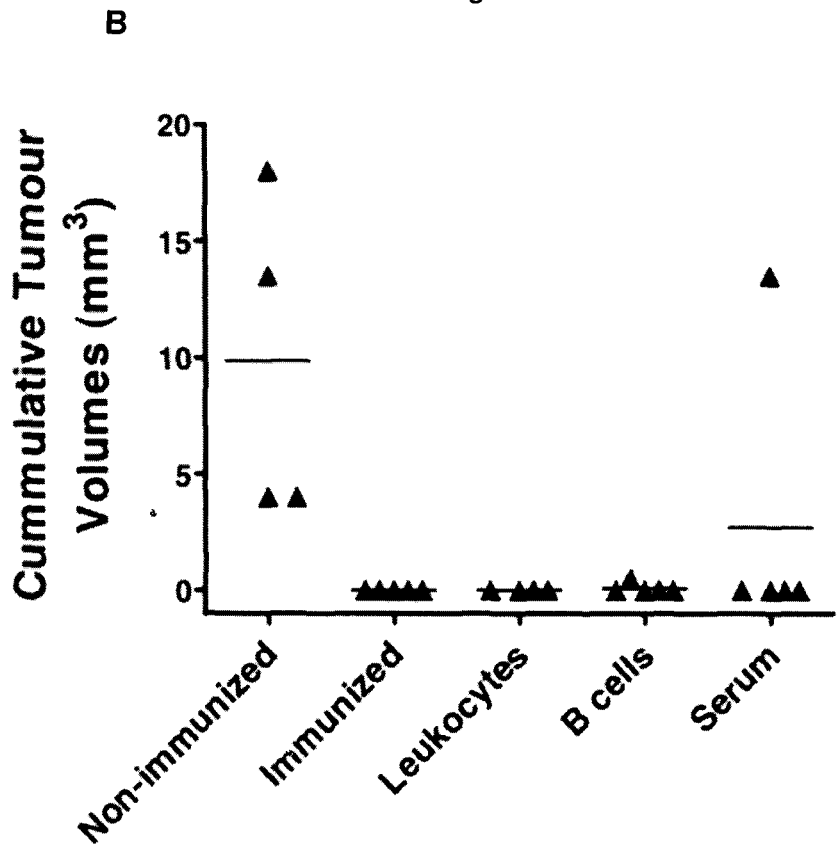

The engendered CEA-specific immune response in CEA.Tg mice is dominated by the production of IgG1 and IgG2a antibodies directed at the N domain of CEA (FIG. 13,14). In contrast, no proliferation of leukocytes was observed in vaccinated transgenic mice irrespective of the antigen used for stimulation (FIG. 19), a finding that suggests a modest level of T cell stimulation as a component of the immune response to rCEA N domain. The detection of antigen-specific cytokine (IL-4, IL-10 and IFN-γ) secreting cells by ELISPOT™ however indicated the presence of a balanced CEA-specific, T$_H$-cell responses (FIG. 13B). The overall response to the CEA N domain is thus distinct from most cancer vaccine strategies aimed at producing an Ag-specific cellular immune response [Berinstein, 2002]. The CEA N domain-specific IgG1 and IgG2a antibody response however has proven beneficial in modulating or blocking the growth of implanted tumours (FIG. 10-14), in inducing Ab-dependent tumour lysis (both by ADCC and CDC) and in interfering with CEA-mediated cellular adhesion (FIG. 15). The importance of B lymphocyte populations in vaccinated mice was confirmed by adoptively transferring CEA-specific B cells or sera from vaccinated animals into naive CEA.Tg mice; components of the immune response that rescue naive recipient mice from developing tumour nodules in their peritoneal cavity (FIG. 16). This outcome parallels the results reported in the study of Park and colleagues [Park et al., 2008], who showed that mounting a polyclonal antibody response targeting the extracellular portion of HER-2/neu led to the cure of large established subcutaneous as well as pulmonary ErbB-2-expressing tumours in mice, presumably by disrupting its biological functions [Park et al., 2008].

In summary, the simple i.p. injection of an altered-self form of the CEA N domain (residues 1-132) elicited CEA N domain-specific immune response in transgenic mice that express this antigen. The engendered antibody response prevented tumour colonization and the development of tumour nodules in either the lungs or the peritoneal cavity of CEA.Tg mice. This antibody-dominated (IgG1 and IgG2a) response led to the specific killing of CEA-expressing cells by Ab-dependent cell lysis mechanisms (ADCC and CDC) in addition to impeding CEA-dependent intercellular adhesion. Since high circulating levels of CEA in the serum of cancer patients frequently correlate with a higher incidence of metastatic relapse, a cancer vaccine formulation using this rCEA N domain as an immunogen may represent a safe and simple adjuvant therapy for cancer patients displaying elevated serum CEA levels prior to surgery.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

1) CEA WT N domain:

A. DNA:

(SEQ ID NO: 3)

AAG CTC ACT ATT GAA TCC ACG CCG TTC AAT GTC GCA

GAG GGG AAG GAG GTG CTT CTA CTT GTC CAC AAT CTG

CCC CAG CAT CTT TTT GGC TAC AGC TGG TAC AAA GGT

GAA AGA GTG GAT GGC AAC CGT CAA ATT ATA GGA TAT

GTA ATA GGA ACT CAA CAA GCT ACC CCA GGG CCC GCA

TAC AGT GGT CGA GAG ATA ATA TAC CCC AAT GCA TCC

CTG CTG ATC CAG AAC ATC ATC CAG AAT GAC ACA GGA

TTC TAC ACC CTA CAC GTC ATA AAG TCA GAT CTT GTG

AAT GAA GAA GCA ACT GGC CAG TTC CGG GTA TAC CCG

GAG CTG CCC AAG CCC TCC ATC TCC AGC AAC AAC TCC

AAA CCC GTG GAG GAC AAG GAT GCT GTG GCC TTC ACC

TABLE 1-continued

B. Protein:
(SEQ ID NO: 1)
KLTIESTPFNVAEGKEVLLLVHNLPQHLFGYSWYKGERVDGNRQIIG
YVIGTQQATPGPAYSGREIIYPNASLLIQNIIQNDTGFYTLHVIKSD
LVNEEATGQFRVYPELPKPSISSNNSKPVEDKDAVAFT 2) Tagged rCEA Mutant N domain nucleotide sequence:

A. DNA:
(SEQ ID NO: 4)
GCGATA catatg *CAT CAT CAC CAT CAC CAT* **GAA AAC
CTC TAT TTC CAA AAG CTC ACT AGC ACT TCC ACG CCG
TTC AAT GTC GCA GAG GGG AAG GAG GTG CTT CTA CTT
GTC CAC AAT CTG CCC CAG CAT CTT TTT GGC TAC AGC
TGG TAC AAA GGT GAA AGA GTG GAT GGC AAC CGT CAA
ATT ATA GGA TAT GTA ATA GGA ACT CAA CAA GCT ACC
CCA GGG CCC GCA TAC AGT GGT CGA GAG ATA ATA TAC
CCC AAT GCA TCC CTG CTG ATC CAG AAC ATC ATC CAG
AAT GAC ACA GGA TTC TAC ACC CTA CAC GTC ATA AAG
TCA GAT CTT GTG AAT GAA GAA GCA ACT GGC CAG TTC
CGG GTA TAC CCG GAG CTG CCC AAG CCC TCC ACC TCC
AGC ACG ACT TCC AAA CCC GTG GAG GAC AAG GAT GCT
GTG GCC TTC ACC** <u>TAG</u> CTCGAG GGA TCC ACT CAG GAC B. Cleaved Mutant rCEA N Protein:
(SEQ ID NO: 2)
KLTSTSTPFNVAEGKEVLLLVHNLPQHLFGYSWYKGERVDGNRQIIG
YVIGTQQATPGPAYSGREIIYPNASLLIQNIIQNDTGFYTLHVIKSD
LVNEEATGQFRVYPELPKPSTSSTTSKPVEDKDAVAFT 3) His-tagged rCEA N: Used as immunogen in Example 2 (Residues 1-132)

Tagged rCEA N domain nucleotide sequence:
(SEQ ID NO: 14)
ATG CAT CAT CAC CAT CAC CAT GAA AAC CTC TAT TTC
CAA AAG CTC ACT ATT GAA TCC ACG CCG TTC AAT GTC
GCA GAG GGG AAG GAG GTG CTT CTA CTT GTC CAC AAT
CTG CCC CAG CAT CTT TTT GGC TAC AGC TGG TAC AAA
GGT GAA AGA GTG GAT GGC AAC CGT CAA ATT ATA GGA
TAT GTA ATA GGA ACT CAA CAA GCT ACC CCA GGG CCC
GCA TAC AGT GGT CGA GAG ATA ATA TAC CCC AAT GCA
TCC CTG CTG ATC CAG AAC ATC ATC CAG AAT GAC ACA
GGA TTC TAC ACC CTA CAC GTC ATA AAG TCA GAT CTT
GTG AAT GAA GAA GCA ACT GGC CAG TTC CGG GTA TAC
CCG GAG CTG CCC AAG CCC TCC ATC TCC AGC AAC AAC
TCC AAA CCC GTG GAG GAC AAG GAT GCT GTG GCC TTC
ACC TAG

TABLE 1-continued

Tagged polypeptide:
(SEQ ID NO: 7)
*MHHHHHHHH*ENLYFQKLTIESTPFNVAEGKEVLLLVHNLPQHLFGYS
WYKGERVDGNRQIIGYVIGTQQATPGPAYSGREIIYPNASLLIQNII
QNDTGFYTLHVIKSDLVNEEATGQFRVYPELPKPSISSNNSKPVEDK
DAVAFT Cleaved rCEA N:
(SEQ ID NO: 1)
KLTIESTPFNVAEGKEVLLLVHNLPQHLFGYSVVYKGERVDGNRQII
GYVIGTQQATPGPAYSGREIIYPNASLLIQNIIQNDTGFYTLHVIKS
DLVNEEATGQFRVYPELPKPSISSNNSKPVEDKDAVAFT

TABLE 2

CEA A$_3$B$_3$:

A. DNA sequence (as cloned in pET30):
(SEQ ID NO: 5)
tatacc CATATG
GCC AAT AAC TCA GCC AGT GGC CAC AGC AGG ACT ACA
GTC AAG ACA ATC ACA GTC TCT GCG GAG CTG CCC AAG
CCC TCC ATC TCC AGC AAC AAC TCC AAA CCC GTG GAG
GAC AAG GAT GCT GTG GCC TTC ACC TGT GAA CCT GAG
GCT CAG AAC ACA ACC TAC CTG TGG TGG GTA AAT GGT
CAG AGC CTC CCA GTC AGT CCC AGG CTG CAG CTG TCC
AAT GGC AAC AGG ACC CTC ACT CTA TTC AAT GTC ACA
AGA AAT GAC GCA AGA GCC TAT GTA TGT GGA ATC CAG
AAC TCA GTG AGT GCA AAC CGC AGT GAC CCA GTC ACC
CTG GAT GTC CTC TAT GGG CCG GAC ACC CCC ATC ATT
TCC CCC CCA GAC TCG TCT TAC CTT TCG GGA GCG AAC
CTC AAC CTC TCC TGC CAC TCG GCC TCT AAC CCA TCC
CCG CAG TAT TCT TGG CGT ATC AAT GGG ATA CCG CAG
CAA CAC ACA CAA GTT CTC TTT ATC GCC AAA ATC ACG
CCA AAT AAT AAC GGG ACC TAT GCC TGT TTT GTC TCT
AAC TTG GCT ACT GGC CGC AAT AAT TCC ATA GTC AAG
AGC ATC ACA GTC TCT GCA TCT GGA ACT TCT CCT GGT
CTC TCA GCT GGG GCC ACT GTC GGC **CAC CAT CAC CAT
CAC CAT CAC CAT TGA** <u>CTCGAG</u> atatag B. Protein sequence (as expressed from pET30):
(SEQ ID NO: 6)
MANNSASGHSRTTVKTITVSAELPKPSISSNNSKPVEDKDAVAFTCE
PEAQNTTYLWWVNGQSLPVSPRLQLSNGNRTLTLFNVTRNDARAYVC
GIQNSVSANRSDPVTLDVLYGPDTPIISPPDSSYLSGANLNLSCHSA
SNPSPQYSWRINGIPQQHTQVLFIAKITPNNNGTYACFVSNLATGRN
NSIVKSITVSASGTSPGLSAGATVGHHHHHHHH

REFERENCES

Abdul-Wahid A, Faubert G. Mucosal delivery of a transmission-blocking DNA vaccine encoding *Giardia lamblia* CWP2 by *Salmonella typhimurium* bactofection vehicle. Vaccine. 2007. 25(50):8372-83.

Asao T, Fukuda T, Yazawa S, Nagamachi Y. CEA levels in peritoneal washings from gastric cancer patients as a prognostic guide. Cancer Lett. 1989. 47(1-2):79-81.

Barchet W, Wimmenauer V, Schlee M, Hartmann G. Accessing the therapeutic potential of immunostimulatory nucleic acids. Curr Opin Immunol. 2008. 20(4):389-95.

Bast R C Jr, Ravdin P, Hayes D F, Bates S, Fritsche H Jr, Jessup J M, Kemeny N, Locker G Y, Mennel R G, Somerfield M R; American Society of Clinical Oncology Tumor Markers Expert Panel. 2000 update of recommendations for the use of tumor markers in breast and colorectal cancer: clinical practice guidelines of the American Society of Clinical Oncology. J Clin Oncol. 2001. 19(6):1865-78.

Benchimol S, Fuks A, Jothy S, Beauchemin N, Shirota K, Stanners C P. Carcinoembryonic antigen, a human tumor marker, functions as an intercellular adhesion molecule. Cell. 1989. 57(2):327-34.

Berinstein N L. Carcinoembryonic antigen as a target for therapeutic anticancer vaccines: a review. J Clin Oncol. 2002. 20(8):2197-207.

Bhattacharya-Chatterjee M, Saha A, Foon K A, Chatterjee S K. Carcinoembryonic antigen transgenic mouse models for immunotherapy and development of cancer vaccines. Curr Protoc Immunol. 2008. Chapter 20:Unit 20.8.

Blumenthal R D, Hansen H J, Goldenberg D M. Inhibition of adhesion, invasion, and metastasis by antibodies targeting CEACAM6 (NCA-90) and CEACAM5 (Carcinoembryonic Antigen). Cancer Res. 2005. 65(19):8809-17.

Bos R, van Duikeren S, Morreau H, Franken K, Schumacher T N, Haanen J B, van der Burg S H, Melief C J, Offring a R. Balancing between antitumor efficacy and autoimmune pathology in T-cell-mediated targeting of carcinoembryonic antigen. Cancer Res. 2008. 68(20):8446-55.

Camacho-Leal P, Stanners C P. The human carcinoembryonic antigen (CEA) GPI anchor mediates anoikis inhibition by inactivation of the intrinsic death pathway. Oncogene. 2008. 27(11):1545-53.

Conaghan, P. J. et al. 2008. Brit J. Cancer. 98: 1217-1225.

Crosti M, Longhi R, Consogno G, Melloni G, Zannini P, Protti M P. Identification of novel subdominant epitopes on the carcinoembryonic antigen recognized by CD4+ T cells of lung cancer patients. J. Immunol. 2006. 176(8):5093-9.

Curigliano G, Spitaleri G, Pietri E, Rescigno M, de Braud F, Cardillo A, Munzone E, Rocca A, Bonizzi G, Brichard V, Orlando L, Goldhirsch A. Breast cancer vaccines: a clinical reality or fairy tale? Aim Oncol. 2006. 17(5):750-62.

Dai S, Wei D, Wu Z, Zhou X, Wei X, Huang H, Li G. Phase I clinical trial of autologous ascites-derived exosomes combined with GM-CSF for colorectal cancer. Mol. Ther. 2008. 16(4):782-90.

Duffy M J. Serum tumor markers in breast cancer: are they of clinical value? Clin Chem. 2006. 52(3):345-51.

Garvey J S, Cremer N E, Sussdorf D H. Methods in immunology, A laboratory text for instruction and research; 3rd ed. Benjamin Cummings Publishing Co. 1983. 189-193.

Gold P, Freedman S O. Specific carcinoembryonic antigens of the human digestive system. J Exp Med. 1965; 122:467-481.

Gold P, Goldenberg N A. The carcinoembryonic antigen (CEA): past present, and future. McGill J. Med. 1997; 3:46-66.

Goldenberg D M, Sharkey R M, Primus F J. Carcinoembryonic antigen in histopathology: immunoperoxidase staining of conventional tissue sections. J Natl Cancer Inst. 1976; 57:11-22.

Gulley J L, Arlen P M, Tsang K Y, Yokokawa J, Palena C, Poole D J, Remondo C, Cereda V, Jones J L, Pazdur M P, Higgins J P, Hodge J W, Steinberg S M, Kotz H, Dahut W L, Schlom J. Pilot study of vaccination with recombinant CEA-MUC-1-TRICOM poxyiral-based vaccines in patients with metastatic carcinoma. Clin Cancer Res. 2008. 14(10):3060-9.

Hammarstrom S. The carcinoembryonic antigen (CEA) family: structures, suggested functions and expression in normal and malignant tissues. Semin Cancer Biol. 1999; 9:67-81.

Hodge J W. Carcinoembryonic antigen as a target for cancer vaccines. Cancer Immunol Immunother. 1996 November; 43(3):127-34.

Hodge J W, Higgins J, Schlom J. Harnessing the unique local immunostimulatory properties of modified vaccinia Ankara (MVA) virus to generate superior tumor-specific immune responses and antitumor activity in a diversified prime and boost vaccine regimen. Vaccine. 2009. 27(33):4475-82.

Hostetter R B, Augustus L B, Mankarious R, Chi K F, Fan D, Toth C, Thomas P, Jessup J M. Carcinoembryonic antigen as a selective enhancer of colorectal cancer metastasis. J Natl Cancer Inst. 1990. 82(5):380-5.

Jessup J M, Kim J C, Thomas P, Ishii S, Ford R, Shively J E, Durbin H, Stanners C P, Fuks A, Zhou H, Hansen H J, Goldenberg D M, Steele Jr G. Adhesion to carcinoembryonic antigen by human colorectal carcinoma cells involves at least two epitopes. Int J. Cancer. 1993. 55(2):262-8.

Jessup J M, Thomas P. CEA and metastasis: a facilitator of site-specific metastasis. In: Stanners C P, editor. Cell Adhesion and Communication by the CEA Family. Vol. 5. Amsterdam, Harwood Academic Publishers; 1998. pp. 195-222.

Kobayashi H, Omiya R, Ruiz M, Huarte E, Sarobe P, Lasarte J J, Herraiz M, Sangro B, Prieto J, Borras-Cuesta F, Celis E. Identification of an antigenic epitope for helper T lymphocytes from carcinoembryonic antigen. Clin Cancer Res. 2002. 8(10):3219-25.

Madrid K P, De Crescenzo G, Wang S, Jardim A. Modulation of the *Leishmania donovani* peroxin 5 quaternary structure by peroxisomal targeting signal 1 ligands. Mol Cell Biol. 2004. 24(17):7331-44.

Matsuda K, Tsunoda T, Tanaka H, Umano Y, Tanimura H, Nukaya I, Takesako K, Yamaue H. Enhancement of cytotoxic T-lymphocyte responses in patients with gastrointestinal malignancies following vaccination with CEA peptide-pulsed dendritic cells. Cancer Immunol Immunother. 2004. 53(7):609-16.

McCluskey A J, Poon G M, Bolewska-Pedyczak E, Srikumar T, Jeram S M, Raught B, Gariépy J. The catalytic subunit of shiga-like toxin 1 interacts with ribosomal stalk proteins and is inhibited by their conserved C-terminal domain. J Mol. Biol. 2008. 378(2):375-86.

Molina R, Jo J, Filella X, Zanon G, Pahisa J, Mu noz M, Farrus B, Latre M L, Escriche C, Estape J, Ballesta A M.

c-erbB-2 oncoprotein, CEA, and CA 15.3 in patients with breast cancer: prognostic value. Breast Cancer Res Treat. 1998. 51(2):109-19.

Molina R, Barak V, van Dalen A, Duffy M J, Einarsson R, Gion M, Goike H, Lamerz R, Nap M, Sölétormos G, Stieber P. Tumor markers in breast cancer-European Group on Tumor Markers recommendations. Tumour Biol. 2005. 26(6):281-93.

Morse M A, Hobeika A C, Osada T, Serra D, Niedzwiecki D, Lyerly H K, Clay T M. Depletion of human regulatory T cells specifically enhances antigen-specific immune responses to cancer vaccines. Blood. 2008. 112(3):610-8.

Nishimura R, Baker J, Beilhack A, Zeiser R, Olson J A, Sega E I, Karimi M, Negrin R S. In vivo trafficking and survival of cytokine-induced killer cells resulting in minimal GVHD with retention of antitumor activity. Blood. 2008. 112(6):2563-74.

Nöckel J, van den Engel N K, Winter H, Hatz R A, Zimmermann W, Kammerer R. Characterization of gastric adenocarcinoma cell lines established from CEA424/SV40 T antigen-transgenic mice with or without a human CEA transgene. BMC Cancer. 2006. 6:57.

Park J M, Terabe M, Steel J C, Formi G, Sakai Y, Morris J C, Berzofsky J A. Therapy of advanced established murine breast cancer with a recombinant adenoviral ErbB-2/neu vaccine. Cancer Res. 2008. 68(6):1979-87.

Samara R N, Laguinge L M, Jessup J M. Carcinoembryonic antigen inhibits anoikis in colorectal carcinoma cells by interfering with TRAIL-R2 (DR5) signaling. Cancer Res. 2007. 67(10):4774-82.

Scher I, Strong D M, Ahmed A, Knudsen R C, Sell K W. Specific murine B-cell activation by synthetic single- and double-stranded polynucleotides. J Exp Med. 1973. 138 (6):1545-63.

Shen L, Schroers R, Hammer J, Huang X F, Chen S Y. Identification of a MHC class-II restricted epitope in carcinoembryonic antigen. Cancer Immunol Immunother. 2004. 53(5):391-403.

Shively J E, Beatty J D. CEA-related antigens: molecular biology and clinical significance. Crit. Rev Oncol Hematol. 1985; 2:355-399.

Singer B B, Scheffrahn I, Kammerer R, Suttorp N, Ergun S, Slevogt H. Deregulation of the CEACAM expression pattern causes undifferentiated cell growth in human lung adenocarcinoma cells. PLoS One. 2010. 5(1):e8747.

Taheri M, Saragovi U, Fuks A, Makkerh J, Mort J, Stanners C P. Self recognition in the Ig superfamily. Identification of precise subdomains in carcinoembryonic antigen required for intercellular adhesion. J Biol. Chem. 2000. 275(35):26935-43.

Thomas P, Gangopadhyay A, Steele G J, Andrews C, Nakazoto H, Oikawa S, Jessup J M. The effect of transfection of the CEA gene on the metastatic behavior of the human colorectal cancer cell line MIP-101. Cancer Lett. 1995; 92:59-66.

Thompson J A, Grunert F, Zimmermann W. Carcinoembryonic antigen gene family: molecular biology and clinical perspectives. J Clin Lab Anal. 1991; 5:344-366.

Tiscornia G, Singer O, Verma I M. Production and purification of lentiviral vectors. Nat. Protoc. 2006. 1(1):241-5.

von Mehren M. Colorectal cancer vaccines: what we know and what we don't yet know. Semin Oncol. 2005. 32(1): 76-84.

Woo S J, Kim C H, Park M Y, Kim H S, Sohn H J, Park J S, Kim H J, Oh S T, Kim T G. Co-administration of carcinoembryonic antigen and HIV TAT fusion protein with CpG-oligodeoxynucleotide induces potent antitumor immunity. Cancer Sci. 2008. 99(5):1034-9.

Yamanka T, Kuroki M, Matsuo Y, Matsuoka Y. Analysis of heterophilic cell adhesion mediated by CD66b and CD66c using their soluble recombinant proteins. Biochem Biophys Res Commun. 1996. 219(3):842-7.

Yoshioka T, Masuko T, Kotanagi H, Aizawa O, Saito Y, Nakazato H, Koyama K, Hashimoto Y. Homotypic adhesion through carcinoembryonic antigen plays a role in hepatic metastasis development. Jpn J Cancer Res. 1998; 89:177-185.

Zhou H, Fuks A, Alcaraz G, Bolling T J, Stanners C P. Homophilic adhesion between Ig superfamily carcinoembryonic antigen molecules involves double reciprocal bonds. J. Cell Biol. 1993. 122(4):951-60.

Zimmer R, Thomas P. Mutations in the carcinoembryonic antigen gene in colorectal cancer patients: implications on liver metastasis. Cancer Res. 2001. 61(7):2822-6.

---

The invention claimed is:

1. A method of inducing an immune response against human carcinoembryonic antigen (CEA) In an animal in need thereof comprising administering an immunogenic composition comprising a peptide consisting of an N-domain of human carcinoembryonic antigen (CEA) which generates CEA N-domain specific sera, to the animal in need thereof; wherein the human N-domain consists of the immunoglobulin variable-like N-terminal region of human CEA and a spacer sequence.

2. The method of claim 1, wherein the N-domain is non-glycosylated or wherein the N-domain has altered glycosylation compared to wild type CEA protein.

3. The method of claim 1, wherein the N-domain of CEA consists of the amino acid sequence as shown in SEQ ID NO: 1 or 2.

4. The method of claim 1, further comprising administering a second peptide consisting of a second isolated CEA domain.

5. The method of claim 4, wherein the second isolated CEA domain is an $A_3B_3$ domain.

6. The method of claim 5, wherein the $A_3B_3$ domain comprises the amino acid sequence as shown in SEQ ID NO:5.

7. The method of claim 1, wherein the spacer sequence consists of the sequence that separates the N and A1 immunoglobulin constant-like domains of human CEA.

8. A method of enhancing an immune response against human carcinoembryonic antigen (CEA) in a subject in need thereof, comprising administering sera to the subject, wherein the sera is generated by administration of an immunogenic composition to an animal, wherein the immunogenic composition comprises a peptide consisting of an N-domain of human carcinoembryonic antigen (CEA); wherein the human N-domain consists of the immunoglobulin variable-like N-terminal region of human CEA and a spacer sequence.

9. The method of claim 8, wherein the N-domain is non-glycosylated or wherein the N-domain has altered glycosylation compared to wild type CEA protein.

10. The method of claim 8, wherein the N-domain of CEA consists of the amino acid sequence as shown in SEQ ID NO: 1 or 2.

11. The method of claim 8, wherein the immunogenic composition further comprises a second peptide consisting of a second isolated CEA domain.

12. The method of claim 11, wherein the second isolated CEA domain is an $A_3B_3$ domain.

13. The method of claim 12, wherein the $A_3B_3$ domain comprises the amino acid sequence as shown in SEQ ID NO:5.

14. The method of claim 8, wherein the spacer sequence consists of the sequence that separates the N and A1 immunoglobulin constant-like domains of human CEA.

* * * * *

UNITED STATES PATENT AND TRADEMARK OFFICE
CERTIFICATE OF CORRECTION

PATENT NO. : 9,636,387 B2
APPLICATION NO. : 14/461585
DATED : May 2, 2017
INVENTOR(S) : Aws Abdul-Wahid et al.

Page 1 of 1

It is certified that error appears in the above-identified patent and that said Letters Patent is hereby corrected as shown below:

In the Claims

In Claim 1 at Column 51, Line 15, "human carcinoembryonic antigen (CEA) In an animal in" should read -- human carcinoembryonic antigen (CEA) in an animal in --.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*